(12) United States Patent
Goo

(10) Patent No.: US 12,667,182 B2
(45) Date of Patent: Jun. 30, 2026

(54) SKIN WHITENING MASK, SKIN WHITENING DEVICE, AND SKIN WHITENING METHOD USING SAME

(71) Applicant: SKINSHIP INC., Seoul (KR)

(72) Inventor: Boncheol Goo, Seoul (KR)

(73) Assignee: SKINSHIP INC., Seoul (KR)

( * ) Notice: Subject to any disclaimer, the term of this patent is extended or adjusted under 35 U.S.C. 154(b) by 1026 days.

(21) Appl. No.: 17/631,405

(22) PCT Filed: Jul. 8, 2020

(86) PCT No.: PCT/KR2020/009937
§ 371 (c)(1),
(2) Date: Jan. 28, 2022

(87) PCT Pub. No.: WO2021/020863
PCT Pub. Date: Feb. 4, 2021

(65) Prior Publication Data
US 2022/0273088 A1      Sep. 1, 2022

Related U.S. Application Data

(60) Provisional application No. 62/880,541, filed on Jul. 30, 2019.

(30) Foreign Application Priority Data

Jan. 3, 2020    (KR) ........................ 10-2020-0001054
Jan. 3, 2020    (KR) ........................ 10-2020-0001055
(Continued)

(51) Int. Cl.
*A45D 44/00*      (2006.01)
*A61F 7/00*       (2006.01)
*A61F 7/02*       (2006.01)

(52) U.S. Cl.
CPC .......... *A45D 44/002* (2013.01); *A61F 7/0053* (2013.01); *A61F 7/007* (2013.01);
(Continued)

(58) Field of Classification Search
CPC ........... A45D 44/002; A61F 2007/0003; A61F 2007/0004; A61F 2007/0056;
(Continued)

(56) References Cited

U.S. PATENT DOCUMENTS 6,004,662 A      12/1999  Buckley
2003/0097845 A1*  5/2003  Saunders ................ F25B 21/04
                                                      62/235.1
(Continued)

FOREIGN PATENT DOCUMENTS

JP        2004-131388 A      4/2004
JP        2015-142605 A      8/2015
(Continued)

OTHER PUBLICATIONS

KR Notice of Allowance in Application No. 10-2020-0001054 dated Dec. 16, 2020.
(Continued)

*Primary Examiner* — Bradford C. Blaise
(74) *Attorney, Agent, or Firm* — Maschoff Brennan

(57)                    ABSTRACT

Provided are a skin whitening mask and device, and a skin whitening method using the same. The mask includes a contact layer having a lower portion in contact with a face surface of a user and provided as a flexible material and at least one thermoelectric module applying cold to a user's face. A heat dissipation layer above the thermoelectric module contacts the second main surface of the thermoelectric module and heat-radiating by receiving heat generated during cooling of the first main surface through the second main surface. A controller controls the thermoelectric mod-
(Continued)

ule such that the first main surface is cooled to a temperature lower than the target temperature so that the user's skin reaches a target temperature at which pigmentation by melanocytes is suppressed, during a time between 5 seconds required to suppress the pigmentation and 300 seconds in which damage to the skin occurs.

11 Claims, 41 Drawing Sheets

(30)  Foreign Application Priority Data

| | | |
|---|---|---|
| Jan. 3, 2020 | (KR) | ......................... 10-2020-0001056 |
| Jan. 3, 2020 | (KR) | ......................... 10-2020-0001057 |

(52) U.S. Cl.
CPC .................... *A45D 2200/155* (2013.01); *A61F 2007/0003* (2013.01); *A61F 2007/0004* (2013.01); *A61F 2007/0052* (2013.01); *A61F 2007/0075* (2013.01); *A61F 2007/0086* (2013.01); *A61F 2007/0244* (2013.01)

(58) Field of Classification Search
CPC ...... A61F 2007/0093; A61F 2007/0095; A61F 7/02; A61F 7/0241; A61F 2007/0225; A61F 2007/0244; A61F 2007/0246; A61F 2007/0282; A61F 2007/0292; A61F 2007/0295; A61F 2007/0075; A61B 18/02; A61B 2018/00011; A61B 2018/0019; A61B 2018/00452; A61B 2018/00791; A61B 2018/0237
See application file for complete search history.

(56) References Cited

U.S. PATENT DOCUMENTS

| | | | | |
|---|---|---|---|---|
| 2013/0331914 | A1* | 12/2013 | Lee | ......................... A61F 7/007 607/96 |
| 2014/0352325 | A1* | 12/2014 | Brown | .................... F25B 21/04 62/3.2 |
| 2017/0348143 | A1* | 12/2017 | Rosen | .................. A61H 23/008 |
| 2018/0098903 | A1* | 4/2018 | Vergara | ................. A61F 7/0085 |
| 2021/0030141 | A1* | 2/2021 | Goo | ....................... A61B 90/98 |

FOREIGN PATENT DOCUMENTS

| | | | |
|---|---|---|---|
| JP | 2019-531176 | A | 10/2019 |
| KR | 2004-31503 | Y1 | 11/2006 |
| KR | 10-2006-0097684 | A | 4/2007 |
| KR | 10-2010-0137697 | A | 12/2010 |
| KR | 10-2012-0012861 | A | 2/2012 |
| KR | 10-2012-0054357 | A | 5/2012 |
| KR | 10-2013-0055737 | A | 5/2013 |
| KR | 10-2016-0100681 | A | 8/2016 |
| KR | 10-2017-0041793 | A | 4/2017 |
| KR | 10-2017-0114672 | A | 10/2017 |
| KR | 10-1914251 | B1 | 10/2017 |
| KR | 10-1840279 | B1 | 11/2017 |
| KR | 10-2018-0024882 | A | 2/2018 |
| KR | 10-2018-0028271 | A | 3/2018 |
| KR | 10-2018-0105886 | A | 10/2018 |
| KR | 10-2018-0133800 | A | 12/2018 |
| KR | 10-2018-0134019 | A | 12/2018 |
| KR | 10-1939805 | B1 | 1/2019 |
| KR | 10-2019-0015757 | A | 2/2019 |
| KR | 10-2019-0015727 | A | 8/2019 |
| KR | 10-2019-0142086 | A | 12/2019 |
| WO | 2018-071933 | A1 | 4/2018 |

OTHER PUBLICATIONS

KR Office Action in Application No. 10-2020-0001055 dated Apr. 26, 2021.
KR Notice of Allowance in Application No. 10-2020-0001055 dated Oct. 12, 2021.
KR Office Action in Application No. 10-2020-0001056 dated Apr. 26, 2021.
KR Notice of Allowance in Application No. 10-2020-0001056 dated Oct. 12, 2021.
KR Office Action in Application No. 10-2020-0001057 dated Apr. 26, 2021.
KR Notice of Allowance in Application No. 10-2020-0001057 dated Oct. 12, 2021.

* cited by examiner

20

21

22

10

<u>50</u>

51   COMMUNICATION MODULE

52   INPUT MODULE

53   OUTPUT MODULE

54   MEMORY

55   CONTROL MODULE

60

11

110

110

110

110

140

130b

130a

120

130

110

110

110

140

130

120

111

111

111

SKIN WHITENING MASK, SKIN WHITENING DEVICE, AND SKIN WHITENING METHOD USING SAME

BACKGROUND

Technical Field

The present invention relates to a mask, a device, and a method for whitening skin, and more particularly, to a mask, a device, and a method for whitening skin that are capable of whitening the skin using cryotherapy.

Background Technology

In recent years, with the improvement in the quality of life, interest in skin care has been increased. In skin care, there are demands for mole removal, pore size reduction, scar removal, wrinkle reduction, and the like, but there is a great demand for skin whitening that lightens the overall skin tone.

To this end, conventionally, skin whitening has been performed by absorbing functional materials, which act to inhibit melanin-producing enzymes in order to lighten the skin tone, into the skin. However, the functional materials have problems in that, due to safety problems such as causing irritation or rash when applied to skin, a use amount is limited, or, due to an insignificant effect, it is substantially difficult to expect the skin whitening effect to occur.

Therefore, there is a need to develop a technology that substantially performs skin whitening.

DETAILED DESCRIPTION OF THE INVENTION

Technical Problem

The present invention is directed to providing a mask, a device, and a method for whitening skin capable of transferring negative heat, which is generated according to an endothermic reaction of a thermoelectric module, without change to a face, thereby conveniently and effectively cooling facial skin of a user and obtaining a whitening effect.

The present invention is also directed to providing a mask, a device, and a method for whitening skin capable of controlling a temperature of a cooling surface of a thermoelectric module and an interval during which the skin is cooled by the thermoelectric module, thereby obtaining an effect of preventing damage to the skin.

The present invention is also directed to providing a mask, a device, and a method for whitening skin capable of maintaining a heat generating surface of a thermoelectric module at a predetermined temperature, thereby obtaining an effect of allowing smooth operation of the thermoelectric module.

The present invention is also directed to providing a mask, a device, and a method for whitening skin capable of controlling a temperature of a thermoelectric module to be within a temperature range in which a functional material is active, thereby obtaining an effect of activating the functional material.

The present invention is also directed to providing a mask, a device, and a method for whitening skin capable of controlling a temperature of a thermoelectric module to a temperature for obtaining additional skin improvement effects such as lipolysis and reduction of swelling, thereby obtaining the additional skin improvement effects.

The present invention is also directed to providing a skin whitening mask, a skin whitening device, and a skin whitening method that are capable of enabling the skin to be maintained at a low temperature for a certain period of time by using a phase change material maintained at a low temperature, thereby obtaining a whitening effect.

The present invention is also directed to providing a skin whitening mask, a skin whitening device, and a skin whitening method that are capable of controlling the cooling time of the skin by controlling the dose of a phase change material, thereby obtaining the effect of preventing skin damage.

Objectives of the present invention are not limited to those described above, and other unmentioned objectives should be clearly understood by those of ordinary skill in the art to which the present invention pertains from the present specification and the accompanying drawings.

Technical Solution

According to one aspect of the present specification, there is provided a mask for whitening skin, the mask comprising a contact layer having a lower portion being contacted with a face surface of a user, and provided as a flexible material for a tight-contact between the lower portion and the face surface, at least one thermoelectric module having two major surfaces including a first major surface disposed in contact with an upper portion of the contact layer and a second major surface positioned opposite to the first major surface, wherein the thermoelectric module cools the first major surface and applies, via the contact layer, a negative heat to a skin of the user, a heat dissipation layer being disposed in contact with the second major surface of the thermoelectric module, wherein the heat dissipation layer receives, via the second major surface, a heat generated upon the cooling of the first major surface and dissipates the generated heat and a controller for controlling the thermoelectric module to: cool the first major surface at a cooling temperature such that the skin of the user reaches a target temperature at which a pigmentation by melanocytes on the user's skin is suppressed, wherein the target temperature is in the range of 4° C. to 27° C. and the cooling temperature is in the range of −15° C. to 15° C. and lower than the target temperature, and maintain the cooling of the first major surface for a cooling interval, wherein the cooling interval is in range of a minimum interval necessary for suppressing the pigmentation and a maximum interval for preventing a skin damage, the minimum interval being greater than 5 second and the maximum interval being smaller than 300 second.

According to another aspect of the present specification, there is provided a mask for whitening skin, the mask comprising a contact layer having a lower portion being contacted with a face surface of a user, and provided as a flexible material for a tight-contact between the lower portion and the face surface, at least one thermoelectric module having two major surfaces including a first major surface disposed in contact with an upper portion of the contact layer and a second major surface positioned opposite to the first major surface, wherein the thermoelectric module cools the first major surface and applies, via the contact layer, a negative heat to a skin of the user, a fluid circulation unit for receiving, via the second major surface, a heat generated upon the cooling of the first major surface and exchanging heat which is received, the fluid circulation unit including: a fluid chamber being disposed in contact with on the thermoelectric module to contact the second major surface of the thermoelectric module and being connected to a fluid inlet passage and a fluid outlet passage, a fluid tank for storing a fluid supplied, via the fluid inlet passage, to the fluid chamber, a pump for supplying, via the fluid inlet passage, the fluid stored in the fluid tank to the fluid chamber and retrieving, via the fluid outlet passage, the fluid to the fluid tank by pumping, and a cooler for cooling the fluid retrieved from the fluid outlet passage, and, a controller for controlling the thermoelectric module to: cool the first major surface at a cooling temperature such that the skin of the user reaches a target temperature at which a pigmentation by melanocytes on the user's skin is suppressed, wherein the target temperature is in the range of 4° C. to 27° C. and the cooling temperature is in the range of –15° C. to 15° C. and lower than the target temperature, and maintain the cooling of the first major surface for a cooling interval, wherein the cooling interval is in range of a minimum interval necessary for suppressing the pigmentation and a maximum interval for preventing a skin damage, the minimum interval being greater than 5 second and the maximum interval being smaller than 300 second.

According to another aspect of the present specification, there is provided a device for whitening skin, the device comprising a contact layer having a lower portion being contacted with a body surface of a user, and provided as a flexible material for a tight-contact between the lower portion and the body surface, at least one thermoelectric module having two major surfaces including a first major surface disposed in contact with an upper portion of the contact layer and a second major surface positioned opposite to the first major surface, wherein the thermoelectric module cools the first major surface and applies, via the contact layer, a negative heat to a skin of the user, a heat dissipation layer being disposed in contact with the second major surface of the thermoelectric module, wherein the heat dissipation layer receives, via the second major surface, a heat generated upon the cooling of the first major surface and dissipates the generated heat and a controller for controlling the thermoelectric module to: cool the first major surface at a cooling temperature such that the skin of the user reaches a target temperature at which a pigmentation by melanocytes on the user's skin is suppressed, wherein the target temperature is in the range of 4° C. to 27° C. and the cooling temperature is in the range of –15° C. to 15° C. and lower than the target temperature, and maintain the cooling of the first major surface for a cooling interval, wherein the cooling interval is in range of a minimum interval necessary for suppressing the pigmentation and a maximum interval for preventing a skin damage, the minimum interval being greater than 5 second and the maximum interval being smaller than 300 second.

According to another aspect of the present specification, there is provided a method for whitening skin, the method comprising, providing a mask onto a face surface of a user so that the mask is contacted with the face surface tightly, wherein the mask comprises a contact layer having a lower portion configured to be contacted with the face surface of the user, and provided as a flexible material for a tight-contact between the lower portion and the face surface, at least one thermoelectric module having two major surfaces including a first major surface disposed in contact with an upper portion of the contact layer and a second major surface positioned opposite to the first major surface, a heat dissipation layer being disposed in contact with the second major surface of the thermoelectric module, and a controller for controlling the thermoelectric module, wherein the thermoelectric module cools the first major surface and applies, via the contact layer, a negative heat to a skin of the user, and wherein the heat dissipation layer receives, via the second major surface, a heat generated upon the cooling of the first major surface and dissipates the generated heat, applying the negative heat, via the contact layer, to the skin of the user by cooling the first major surface, suppressing a pigmentation by melanocytes on the user's skin by cooling the first major surface at a cooling temperature such that the skin of the user reaches a target temperature, wherein the target temperature is in the range of 4° C. to 27° C. and the cooling temperature is in the range of –15° C. to 15° C. and lower than the target temperature and preventing a skin damage by maintaining the cooling of the first major surface for a cooling interval, wherein the cooling interval is in range of a minimum interval necessary for suppressing the pigmentation and a maximum interval for preventing the skin damage, the minimum interval being greater than 5 second and the maximum interval being smaller than 300 second.

According to another aspect of the present specification, there is provided a mask for whitening skin, the mask comprising a contact layer having a lower portion in contact with a face surface of a user, and provided as a flexible material for a tight-contact between the lower portion and the face surface, a cooling layer disposed on an upper portion of the contact layer and including a phase change material that prepared in a state of being cooled to a melting point or less and applying negative heat to the user's skin using latent heat at the melting point for a duration of time when the melting point is maintained through the contact layer—the phase change material has a melting point below a target temperature at which pigmentation by melanocyte is suppressed, and has a mass that maintains the duration longer than a first time required for suppressing pigmentation and shorter than a second time during which damage to the skin occurs, and an outer cover disposed on the upper part of the cooling layer, provided in a shape corresponding to the user's face, and provided as an insulating material so that negative heat of the cooling layer does not leak to the outside.

According to another aspect of the present specification, there is provided a device for whitening skin, the device comprising a contact layer having a lower portion in contact with a body surface of a user, and provided as a flexible material for a tight-contact between the lower portion and the body surface, a cooling layer disposed on an upper portion of the contact layer and including a phase change material that prepared in a state of being cooled to a melting point or less and applying negative heat to the user's skin using latent heat at the melting point for a duration of time when the melting point is maintained through the contact layer—the phase change material has a melting point below a target temperature at which pigmentation by melanocyte is suppressed, and has a mass that maintains the duration longer than a first time required for suppressing pigmentation and shorter than a second time during which damage to the skin occurs, and an outer cover disposed on the upper part of the cooling layer, and provided as an insulating material so that negative heat of the cooling layer does not leak to the outside.

According to another aspect of the present specification, there is provided a method for whitening skin, the method comprising a mask for whitening skin, wherein the mask includes a contact layer having a lower portion in contact with a face surface of a user, and provided as a flexible material, a cooling layer including a phase change material disposed on an upper part of the contact layer and prepared in a state of being cooled to a melting point or less, provided in shape corresponding to the user's face, and an outer cover provided as an insulating material. The method comprises: cooling the cooling layer below the melting point of the phase change material; placing the skin whitening mask on the user's face so that the lower part of the contact layer is in close contact with the face; suppressing the pigmentation of the face adhered to the lower part of the contact layer closely, wherein negative heat is applied to the user's skin by using latent heat at the melting point of the phase change material for at least a period of time when the melting point is maintained longer than a first time required to suppress the pigmentation through the contact layer; and preventing damage to the face as the phase change of the phase change material ends before a second time in which damage to the skin occurs elapses.

Means for achieving the objectives of the present invention are not limited to those described above, and other unmentioned means should be clearly understood by those of ordinary skill in the art to which the present invention pertains from the present specification and the accompanying drawings.

Effects of the Invention

According to an embodiment of the present specification, by transferring negative heat, which is generated according to an endothermic reaction of a thermoelectric module, without change to a face, it is possible to conveniently and effectively cool facial skin of a user and obtain a whitening effect.

According to another embodiment of the present specification, by controlling a cooling temperature of a cooling surface of a thermoelectric module and an interval during which cooling occurs, it is possible to obtain an effect of preventing damage to the skin.

According to another embodiment of the present specification, by maintaining a heat generating surface of a thermoelectric module at a predetermined temperature, it is possible to obtain an effect of allowing smooth operation of the thermoelectric module.

According to another embodiment of the present specification, by controlling a temperature of a thermoelectric module to be within a temperature range in which a functional material is active, it is possible to obtain an effect of activating the functional material.

According to another embodiment of the present specification, by controlling a temperature of a thermoelectric module, it is possible to obtain additional skin improvement effects such as lipolysis and reduction of swelling.

According to another embodiment of the present specification, it is possible to obtain a whitening effect by suppressing pigmentation caused by melanocytes by maintaining the skin at a low temperature for a certain period of time using a phase change material maintained at a low temperature.

According to another embodiment of the present specification, it is possible to obtain an effect of preventing skin damage due to excessive cooling by controlling the time for skin cooling through adjusting the capacity of the phase change material.

Advantageous effects of the present invention are not limited to those described above, and other unmentioned advantageous effects should be clearly understood by those of ordinary skill in the art to which the present invention pertains from the present specification and the accompanying drawings.

6

BEST MODE FOR IMPLEMENTATION OF THE INVENTION

Figure 1:
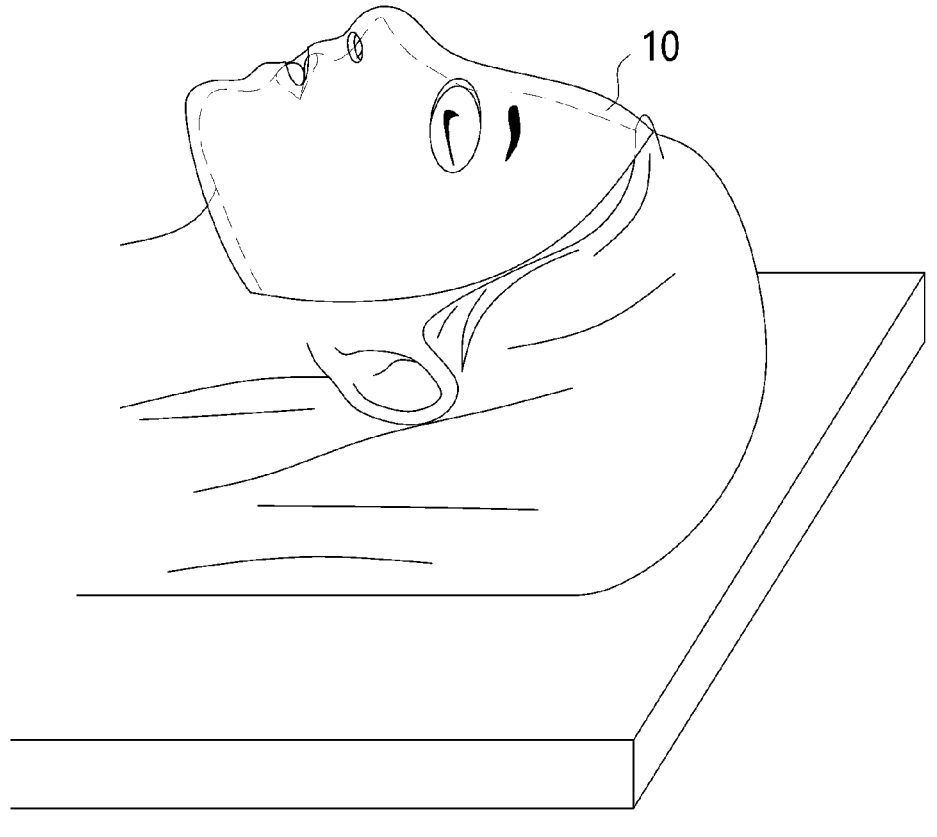
FIG. 1 is a view illustrating a state in which a user uses a skin whitening mask according to an embodiment of the present specification.

The above-mentioned objectives, features, and advantages of the present invention will become more apparent from the following detailed description related to the accompanying drawings. However, the present invention may be modified in various ways and have various embodiments. Hereinafter, specific embodiments which are illustrated in the drawings will be described in detail.

In the drawings, the thicknesses of layers and regions are exaggerated for clarity. Also, when an element or layer is described as being "on" or "above" another element or layer, this includes both a case in which the element or layer is directly on the other element or layer and a case in which still another element or layer is interposed therebetween. In principle, like reference numerals refer to like elements throughout. Also, elements having the same function within the scope of the same idea shown in the drawings of each embodiment will be described using the same reference numerals.

When detailed description of known functions or configurations related to the present invention is deemed as having the possibility of unnecessarily blurring the gist of the present invention, the detailed description thereof will be omitted. Also, ordinals (e.g., first and second) used in the description process of the present specification are merely identification symbols for distinguishing one element from another element.

In addition, the terms "module" and "part" which are used to refer to elements in the following description have been given or used in combination with other terms only in consideration of ease of writing the specification and thus do not have meanings or roles that are distinguished from each other.

When a heat exchange occurs between objects with different temperatures, it may be assumed that an object with a relatively higher temperature generates heat and an object with a relatively lower temperature absorbs the heat. Therefore, when an arbitrary object is adjacent to the human skin, the arbitrary object may generate thermal energy when a temperature of the arbitrary object is higher than a temperature of the human skin, and the arbitrary object may absorb thermal energy when the temperature of the arbitrary object is lower than the temperature of the human skin. Thus, in the present specification, absorbing thermal energy from the human skin by the arbitrary object may refer to "applying negative heat to the human skin." Also, the term "cooling" used herein may refer to lowering a temperature of an object to be cooled to a temperature lower than that before cooling the object.

In the present specification, "whitening skin" refers to any action that inhibits melanin synthesis and suppresses or prevents pigmentation due to melanin. For example, skin whitening may include lightening a skin tone as a result of cooling the skin and suppressing pigmentation of the skin, removing a mole on the skin, and the like.

In the present specification, an operation mode may refer to cooling a cooling surface of a thermoelectric module according to predetermined cooling temperature and cooling interval.

In the present specification, a whitening mode may refer to cooling the cooling surface of the thermoelectric module according to a predetermined cooling condition for causing a whitening effect of skin.

In the present specification, a functional material activation mode may refer to cooling the cooling surface of the thermoelectric module according to a predetermined cooling condition for causing an effect of activating a functional material.

In the present specification, a lipolysis mode may refer to cooling the cooling surface of the thermoelectric module according to a predetermined cooling condition for causing a lipolytic effect.

In the present specification, a swelling reduction mode may refer to cooling the cooling surface of the thermoelectric module according to a predetermined cooling condition for causing an effect of reducing swelling.

One aspect of the present specification may provide a mask for whitening skin, the mask comprising a contact layer having a lower portion being contacted with a face surface of a user, and provided as a flexible material for a tight-contact between the lower portion and the face surface, at least one thermoelectric module having two major surfaces including a first major surface disposed in contact with an upper portion of the contact layer and a second major surface positioned opposite to the first major surface, wherein the thermoelectric module cools the first major surface and applies, via the contact layer, a negative heat to a skin of the user, a heat dissipation layer being disposed in contact with the second major surface of the thermoelectric module, wherein the heat dissipation layer receives, via the second major surface, a heat generated upon the cooling of the first major surface and dissipates the generated heat and a controller for controlling the thermoelectric module to: cool the first major surface at a cooling temperature such that the skin of the user reaches a target temperature at which a pigmentation by melanocytes on the user's skin is suppressed, wherein the target temperature is in the range of 4° C. to 27° C. and the cooling temperature is in the range of −15° C. to 15° C. and lower than the target temperature, and maintain the cooling of the first major surface for a cooling interval, wherein the cooling interval is in range of a minimum interval necessary for suppressing the pigmentation and a maximum interval for preventing a skin damage, the minimum interval being greater than 5 second and the maximum interval being smaller than 300 second.

In addition, the mask may further comprise a skin temperature sensor for measuring a skin temperature of the skin and wherein the controller controls the thermoelectric module based on the skin temperature measured from the skin temperature sensor.

In addition, the controller may control the thermoelectric module to maintain the measured temperature at the target temperature for 4 seconds to 120 seconds.

In addition, the mask may further comprise a vibration generating module for outputting vibration applied to the face surface; and wherein the controller controls the vibration generating module to output a vibration during or after the cooling of the first major surface.

In addition, the mask may further comprise a touch sensing module for sensing a contact of the skin with the mask and wherein the controller controls the thermoelectric module to start the cooling of the first major surface when the contact of the skin is detected by the touch sensing module.

In addition, the controller may control the thermoelectric module to slowly increase a temperature of the first major surface after the cooling of the first major surface.

In addition, the thermoelectric module may include a plurality of thermoelectric module groups, and each of the plurality of thermoelectric module groups is controlled separately by the controller.

In addition, the plurality of thermoelectric module groups may correspond to a plurality of face surface sections being defined based on a skin temperature profile.

In addition, the plurality of thermoelectric module groups may include a first thermoelectric group corresponding to a first section and a second thermoelectric group corresponding to a second section of which the skin temperature is lower than that of the first section, and the controller controls the first thermoelectric group to perform the cooling of the first major surface corresponding to the first section for a first cooling interval and the second thermoelectric group to perform the cooling of the first major surface corresponding to the second section for a second cooling interval, the first cooling interval being greater than the second cooling interval.

In addition, the plurality of thermoelectric module groups may include a first thermoelectric group corresponding to a first section and a second thermoelectric group corresponding to a second section of which the skin temperature is lower than that of the first section, and the controller controls the first thermoelectric group to perform the cooling of the first major surface corresponding to the first section at a first cooling temperature and the second thermoelectric group to perform the cooling of the first major surface corresponding to the second section at a second cooling temperature, the first cooling temperature being higher than the second cooling temperature.

In addition, the controller may further include an input module for obtaining a cooling condition of the first major surface, and control the thermoelectric module to cool the first major surface according to the cooling condition inputted from the input module.

In addition, the controller may further include a communication module for communicating with an external device, and control the thermoelectric module to cool the first major surface according to the cooling condition obtained from the communication module.

In addition, the controller may control the thermoelectric module to cool the first surface according to a first cooling condition related to a swelling reduction effect of the skin or a second cooling condition related to lipolysis effect of the skin during at least a portion of the cooling interval of the first major surface.

In addition, the thermoelectric module may have flexibility.

In addition, the heat dissipation layer may include a fluid chamber which receives fluid from a fluid supply module storing the fluid, and exchanges heat by receiving the heat generated upon the cooling of the first major surface.

In addition, the fluid chamber may include a plurality of chambers, the plurality of chambers being connected in series and/or in parallel between the chambers.

In addition, another aspect of the present specification may provide a mask for whitening skin, the mask comprising a contact layer having a lower portion being contacted with a face surface of a user, and provided as a flexible material for a tight-contact between the lower portion and the face surface, at least one thermoelectric module having two major surfaces including a first major surface disposed in contact with an upper portion of the contact layer and a second major surface positioned opposite to the first major surface, wherein the thermoelectric module cools the first major surface and applies, via the contact layer, a negative heat to a skin of the user, a fluid circulation unit for receiving, via the second major surface, a heat generated upon the cooling of the first major surface and exchanging heat which is received, the fluid circulation unit including: a fluid chamber being disposed in contact with on the thermoelectric module to contact the second major surface of the thermoelectric module and being connected to a fluid inlet passage and a fluid outlet passage, a fluid tank for storing a fluid supplied, via the fluid inlet passage, to the fluid chamber, a pump for supplying, via the fluid inlet passage, the fluid stored in the fluid tank to the fluid chamber and retrieving, via the fluid outlet passage, the fluid to the fluid tank by pumping, and a cooler for cooling the fluid retrieved from the fluid outlet passage, and, a controller for controlling the thermoelectric module to: cool the first major surface at a cooling temperature such that the skin of the user reaches a target temperature at which a pigmentation by melanocytes on the user's skin is suppressed, wherein the target temperature is in the range of 4° C. to 27° C. and the cooling temperature is in the range of –15° C. to 15° C. and lower than the target temperature, and maintain the cooling of the first major surface for a cooling interval, wherein the cooling interval is in range of a minimum interval necessary for suppressing the pigmentation and a maximum interval for preventing a skin damage, the minimum interval being greater than 5 second and the maximum interval being smaller than 300 second.

In addition, another aspect of the present specification may provide a device for whitening skin, the device comprising a contact layer having a lower portion being contacted with a body surface of a user, and provided as a flexible material for a tight-contact between the lower portion and the body surface, at least one thermoelectric module having two major surfaces including a first major surface disposed in contact with an upper portion of the contact layer and a second major surface positioned opposite to the first major surface, wherein the thermoelectric module cools the first major surface and applies, via the contact layer, a negative heat to a skin of the user, a heat dissipation layer being disposed in contact with the second major surface of the thermoelectric module, wherein the heat dissipation layer receives, via the second major surface, a heat generated upon the cooling of the first major surface and dissipates the generated heat and a controller for controlling the thermoelectric module to: cool the first major surface at a cooling temperature such that the skin of the user reaches a target temperature at which a pigmentation by melanocytes on the user's skin is suppressed, wherein the target temperature is in the range of 4° C. to 27° C. and the cooling temperature is in the range of –15° C. to 15° C. and lower than the target temperature, and maintain the cooling of the first major surface for a cooling interval, wherein the cooling interval is in range of a minimum interval necessary for suppressing the pigmentation and a maximum interval for preventing a skin damage, the minimum interval being greater than 5 second and the maximum interval being smaller than 300 second.

In addition, another aspect of the present specification may provide a method for whitening skin, the method comprising, providing a mask onto a face surface of a user so that the mask is contacted with the face surface tightly, wherein the mask comprises a contact layer having a lower portion configured to be contacted with the face surface of the user, and provided as a flexible material for a tight-contact between the lower portion and the face surface, at least one thermoelectric module having two major surfaces including a first major surface disposed in contact with an upper portion of the contact layer and a second major surface positioned opposite to the first major surface, a heat dissipation layer being disposed in contact with the second major surface of the thermoelectric module, and a controller for controlling the thermoelectric module, wherein the thermoelectric module cools the first major surface and applies, via the contact layer, a negative heat to a skin of the user, and wherein the heat dissipation layer receives, via the second major surface, a heat generated upon the cooling of the first major surface and dissipates the generated heat, applying the negative heat, via the contact layer, to the skin of the user by cooling the first major surface, suppressing a pigmentation by melanocytes on the user's skin by cooling the first major surface at a cooling temperature such that the skin of the user reaches a target temperature, wherein the target temperature is in the range of 4° C. to 27° C. and the cooling temperature is in the range of –15° C. to 15° C. and lower than the target temperature and preventing a skin damage by maintaining the cooling of the first major surface for a cooling interval, wherein the cooling interval is in range of a minimum interval necessary for suppressing the pigmentation and a maximum interval for preventing the skin damage, the minimum interval being greater than 5 second and the maximum interval being smaller than 300 second.

In addition, another aspect of the present specification may provide a mask that for whitening skin, the mask including, a contact layer having a lower portion being contacted with a face surface of a user, and provided as a flexible material for a tight-contact between the lower portion and the face surface, at least one thermoelectric module having two major surfaces including a first major surface disposed in contact with an upper portion of the contact layer and a second major surface positioned opposite to the first major surface, wherein the thermoelectric module cools the first major surface and applies, via the contact layer, a negative heat to a skin of the user, a heat dissipation layer disposed at an upper portion of the thermoelectric module so as to come in contact with the second major surface of the thermoelectric module and configured to receive, via the second major surface, heat generated upon cooling of the first major surface and dissipate the received heat, and a controller configured to control the thermoelectric module to cool the first major surface within a whitening temperature range in which pigmentation by melanocytes is suppressed and control the thermoelectric module to cause the whitening temperature range and the activation temperature range of the functional material to overlap during at least a portion of a whitening interval, during which the cooling of the first major surface occurs within the whitening temperature range.

In addition, the functional material may be formed of at least one of an ingredient that helps protect against UV rays, an ingredient that prevents oxidation, an ingredient that conditions the skin, an ingredient that inhibits the action of bacteria, an ingredient that whitens the skin, an ingredient that reduces the size of pores, an ingredient that reduces wrinkles, an ingredient that revitalizes the skin, an ingredient that prevents burning sensation, and an ingredient that relieves pain or a mixture of two or more thereof.

In addition, the functional material may include a material whose skin improving function is further activated at low temperature.

In addition, the functional material may be a material whose whitening effect is further enhanced at low temperature and may be formed of at least one of resorcinol and similar derivatives (hexyl resorcinol, butyl resorcinol, phenylethyl resorcinol, resorcinol acetate, and other similar derivatives) or a mixture of two or more thereof.

In addition, the functional material may be a material that further reduces irritation at low temperature and may be formed of at least one of, or a mixture of two or more of, niacinamide and a composition containing the same, magnesium ascorbylphosphate and a composition containing the same, ascorbyl glucoside and a composition containing the same, ascorbyl tetraisopalmitate/dipalmitate and a composition containing the same, arbutin and a composition containing the same, α-bisabolol and a composition containing the same, ethyl ascorbyl ether and a composition containing the same, polyphenol derivatives and a composition containing the same, L-glutathione and a composition containing the same, tranexamic acid and a composition containing the same, 4-methoxysalicylic acid potassium salt (KCl) derivatives and a composition containing the same, glycyrrhizin and a composition containing the same, azelaic acid, azelaic acid derivatives (e.g., azeloyl diglycine) and a composition containing the same, nicotinamide, nicotinamide derivatives and a composition containing the same, resveratrol, resveratrol derivatives and a composition containing the same, glycyrrhiza flavonoids, ellagic acid and a composition containing the same, papain and a composition containing the same, mandelic acid, mandelic acid derivatives and a composition containing the same, heptapeptide-1 and a composition containing the same, kojic acid, kojic acid derivatives and a composition containing the same, and plant extracts and a composition containing the same that contain all or some of the following ingredients: jasmine extract, mulberry extract, paper mulberry extract, licorice extract, ginseng extract, salvia miltiorrhiza extract, corn extract, chrysanthemum extract, bark root extract, thyme extract, white fresh root extract, polygon extract, magnolia tree extract, angelica root extract, *Phyllanthus emblica* (fruit) extract, and citrus extract.

In addition, the controller may control the thermoelectric module to cool the first major surface at a temperature at which the activity of the functional material is maximized.

In addition, when the functional material is provided as a plurality of functional materials, the controller may control the thermoelectric module to cause the whitening temperature range and the activation temperature range of at least one of the plurality of functional materials to overlap.

In addition, the whitening temperature range may be a range of −15° C. to 15° C.

In addition, the whitening interval may be maintained between 5 seconds, which is necessary for suppressing the pigmentation, and less than 300 seconds, at which damage to the skin begins.

In addition, the contact layer may be separable from the mask.

In addition, the mask may further include an identification tag which is disposed at the contact layer and has identification data corresponding to the functional material and a tag recognition module configured to recognize the identification tag, and the controller may identify the functional material from the identification data obtained by the tag recognition module recognizing the identification tag.

In addition, the identification tag may have data relating to a cooling condition of the first major surface that corresponds to the identification data, and the controller may control the thermoelectric module to cool the first major surface according to the cooling condition of the first major surface corresponding to the identification data that is obtained by the tag recognition module recognizing the identification tag.

Another aspect of the present specification may provide a mask for whitening skin, the mask comprising, a contact layer having a lower portion in contact with a face surface of a user, and provided as a flexible material for a tight-contact between the lower portion and the face surface, at least one thermoelectric module having two major surfaces including a first major surface disposed in contact with an upper portion of the contact layer and a second major surface positioned opposite to the first major surface, wherein the thermoelectric module cools the first major surface and applies, via the contact layer, a negative heat to a skin of the user, a heat dissipation layer disposed at an upper portion of the thermoelectric module so as to come in contact with the second major surface of the thermoelectric module and configured to receive, via the second major surface, heat generated upon cooling of the first major surface and dissipate the received heat, and a controller configured to control the thermoelectric module to perform a first mode in which the first major surface is cooled at a temperature at which pigmentation by melanocytes is suppressed in order to whiten the skin or a second mode in which the first major surface is cooled within an activation temperature range of the functional material in order to improve the activity of the functional material.

In addition, the functional material may be formed of at least one of an ingredient that helps protect against UV rays, an ingredient that prevents oxidation, an ingredient that conditions the skin, an ingredient that inhibits the action of bacteria, an ingredient that whitens the skin, an ingredient that reduces the size of pores, an ingredient that reduces wrinkles, an ingredient that revitalizes the skin, an ingredient that prevents burning sensation, and an ingredient that relieves pain or a mixture of two or more thereof.

In addition, the functional material may include a material whose skin improving function is further activated at low temperature.

In addition, the functional material may be a material whose whitening effect is further enhanced at low temperature and may be formed of at least one of resorcinol and similar derivatives (hexyl resorcinol, butyl resorcinol, phenylethyl resorcinol, resorcinol acetate, and other similar derivatives) or a mixture of two or more thereof.

In addition, the functional material may be a material that further reduces irritation at low temperature and may be formed of at least one of, or a mixture of two or more of, niacinamide and a composition containing the same, magnesium ascorbylphosphate and a composition containing the same, ascorbyl glucoside and a composition containing the same, ascorbyl tetraisopalmitate/dipalmitate and a composition containing the same, arbutin and a composition containing the same, α-bisabolol and a composition containing the same, ethyl ascorbyl ether and a composition containing the same, polyphenol derivatives and a composition containing the same, L-glutathione and a composition containing the same, tranexamic acid and a composition containing the same, 4-methoxysalicylic acid potassium salt (KCl) derivatives and a composition containing the same, glycyrrhizin and a composition containing the same, azelaic acid, azelaic acid derivatives (e.g., azeloyl diglycine) and a composition containing the same, nicotinamide, nicotinamide derivatives and a composition containing the same, resveratrol, resveratrol derivatives and a composition containing the same, glycyrrhiza flavonoids, ellagic acid and a composition containing the same, papain and a composition containing the same, mandelic acid, mandelic acid derivatives and a composition containing the same, heptapeptide-1 and a composition containing the same, kojic acid, kojic acid derivatives and a composition containing the same, and plant extracts and a composition containing the same that contain all or some of the following ingredients: jasmine extract, mulberry extract, paper mulberry extract, licorice extract, ginseng extract, salvia miltiorrhiza extract, corn extract, chrysanthemum extract, bark root extract, thyme extract, white fresh root extract, polygon extract, magnolia tree extract, angelica root extract, *Phyllanthus emblica* (fruit) extract, and citrus extract. In addition, the controller may control the thermoelectric module to maintain an interval during which the first mode is performed to be shorter than an interval during which the second mode is performed.

In addition, the controller may control the thermoelectric module to cool the first major surface at a higher temperature when performing the second mode as compared to when performing the first mode.

In addition, when the functional material is provided as a plurality of functional materials, the controller may control the thermoelectric module to cool the first major surface within the activation temperature range of at least one of the plurality of functional materials while performing the second mode.

In addition, the controller may control the thermoelectric module to perform the second mode simultaneously with the first mode during at least a portion of the interval during which the first mode is performed.

In addition, the first mode may be a mode in which the first major surface is cooled within a temperature range of −15° C. to 15° C.

In addition, the first mode may be a mode in which the cooling of the first major surface is maintained between 5 seconds, which is necessary for suppressing the pigmentation, and less than 300 seconds, at which damage to the skin begins.

In addition, the second mode may be a mode in which the first major surface is cooled at a temperature at which the activity of the functional material is maximized.

In addition, another aspect of the present specification may provide a method for whitening skin, the method comprising, positioning onto a face of a user, a mask, which includes a contact layer having a lower portion being contacted with a face surface of a user, and provided as a flexible material for a tight-contact between the lower portion and the face surface, at least one thermoelectric module having two major surfaces including a first major surface disposed in contact with an upper portion of the contact layer and a second major surface positioned opposite to the first major surface, wherein the thermoelectric module cools the first major surface and applies, via the contact layer, a negative heat to a skin of the user, a heat dissipation layer disposed at an upper portion of the thermoelectric module so as to come in contact with the second major surface of the thermoelectric module and configured to receive, via the second major surface, heat generated upon cooling of the first major surface and dissipate the received heat, and a controller configured to control the thermoelectric module, so that the lower portion of the contact layer adheres to the face, as the power is applied to the thermoelectric module, cooling the first major surface and applying negative heat to the skin of the user via the contact layer, by the controller, performing whitening of the skin by cooling the first major surface within a whitening temperature range in which pigmentation by melanocytes is suppressed, and by the controller, activating the functional material by causing the whitening temperature range and the activation temperature range of the functional material to overlap during at least a portion of a whitening interval, during which the cooling of the first major surface occurs within the whitening temperature range.

In addition, another aspect of the present specification may provide a mask for whitening skin, the mask comprising, a contact layer having a lower portion being contacted with a face surface of a user, and provided as a flexible material for a tight-contact between the lower portion and the face surface, at least one thermoelectric module having two major surfaces including a first major surface disposed in contact with an upper portion of the contact layer and a second major surface positioned opposite to the first major surface, wherein the thermoelectric module cools the first major surface and applies, via the contact layer, a negative heat to a skin of the user, a phase-change material heat dissipation layer which is disposed at an upper portion of the thermoelectric module so as to come in contact with the second major surface of the thermoelectric module and includes a phase-change material which receives, via the second major surface, heat generated upon cooling of the first major surface and absorbs the received heat and maintains the temperature of the second major surface constant using latent heat at a melting point in order to maintain a difference between a temperature of the first major surface and a temperature of the second major surface to be less than a predetermined temperature, and a controller configured to control the thermoelectric module to cool the first major surface at a temperature at which pigmentation by melanocytes is suppressed in order to whiten the skin.

In addition, the predetermined temperature may be selected from a range of 30° C. to less than 55° C.

In addition, the phase-change material may have a melting point in a range of −15° C. to 40° C.

In addition, a mass of the phase-change material may be determined on the basis of input power and use time of the thermoelectric module, an amount of heat absorbed by the first major surface, and the latent heat at the melting point of the phase-change material.

In addition, a mass G of the phase-change material may be determined by Equation 1 below.

$$G = \frac{(Q_c + P) \cdot t}{(\Delta H)} \qquad \text{(Equation 1)}$$

Here, $Q_c$ represents the amount of heat absorbed by the first major surface, P represents the input power of the thermoelectric module, t represents the use time of the thermoelectric module, and $\Delta H$ represents the latent heat at the melting point of the phase-change material.

In addition, the phase-change material heat dissipation layer may include therein a heat transfer member formed of a material with high thermal conductivity.

In addition, the mask may further include a metal heat dissipation layer which is formed of a metal material with high thermal conductivity and is disposed between the phase-change material heat dissipation layer and the thermoelectric module so that one surface comes in contact with the thermoelectric module and the other surface comes in contact with the phase-change material heat dissipation layer.

In addition, the surface of the metal heat dissipation layer that comes in contact with the phase-change material heat dissipation layer may be formed of a concavo-convex structure.

In addition, the mask may further include a housing for positioning the phase-change material heat dissipation layer, and the phase-change material heat dissipation layer may be mountable on or separable from the housing.

In addition, the mask may further include an outer cover disposed at an upper portion of the phase-change material heat dissipation layer, and, in the outer cover, a fan configured to introduce outside air, exchange heat, and discharge heat generated at the second major surface to the outside may be installed.

In addition, the controller may control the thermoelectric module to cool the first major surface within a temperature range of −15° C. to 15° C.

In addition, the controller may control the thermoelectric module to maintain the cooling of the first major surface between 5 seconds, which is necessary for suppressing the pigmentation, and less than 300 seconds, at which damage to the skin begins.

In addition, another aspect of the present specification may provide a device for whitening skin, the device comprising, a contact layer having a lower portion being contacted with a face surface of a user, and provided as a flexible material for a tight-contact between the lower portion and the face surface, at least one thermoelectric module having two major surfaces including a first major surface disposed in contact with an upper portion of the contact layer and a second major surface positioned opposite to the first major surface, wherein the thermoelectric module cools the first major surface and applies, via the contact layer, a negative heat to a skin of the user, a phase-change material heat dissipation layer which is disposed at an upper portion of the thermoelectric module so as to come in contact with the second major surface of the thermoelectric module and includes a phase-change material which receives, via the second major surface, heat generated upon cooling of the first major surface and absorbs the received heat and maintains the temperature of the second major surface constant using latent heat at a melting point in order to maintain a difference between a temperature of the first major surface and a temperature of the second major surface to be less than a predetermined temperature, and a controller configured to control the thermoelectric module to cool the first major surface at a temperature at which pigmentation by melanocytes is suppressed in order to whiten the skin.

In addition, another aspect of the present specification may provide a mask for whitening skin, the mask comprising a contact layer having a lower portion in contact with a face surface of a user, and provided as a flexible material for a tight-contact between the lower portion and the face surface, a cooling layer disposed on an upper part of the contact layer and including a phase change material that prepared in a state of being cooled to a melting point or less and applying negative heat to the user's skin using latent heat at the melting point for a duration of time when the melting point is maintained through the contact layer—the phase change material has a melting point below a target temperature at which pigmentation by melanocyte is suppressed, and has a mass that maintains the duration longer than a first time required for suppressing pigmentation and shorter than a second time during which damage to the skin occurs, and an outer cover disposed on the upper part of the cooling layer, provided in a shape corresponding to the user's face, and provided as an insulating material so that negative heat of the cooling layer does not leak to the outside.

Also, the mass of the phase change material may be determined based on the target temperature, the melting point of the phase change material, latent heat at the melting point of the phase change material, and the area of the mask.

In addition, the mass (G) of the phase change material may be determined by Equations 1 and 2 below.

$$G = \frac{(QHC)\cdot(A)}{(\Delta H)} \quad \text{(Equation 1)}$$

$$QHC = \int_{\tau=0}^{\tau=max} qHC\partial\tau \quad \text{(Equation 2)}$$

18

—Here, A is the area of the mask, ΔH is the latent heat at the melting point of the phase change material, τ is the duration time, qHC is the heat flux on the skin surface, $Q_{HC}$ is the amount of heat emitted from the skin—

In addition, the phase change material may have a melting point in the range of −15° C. to 15° C.

In addition, the target temperature may be in the range of 4° C. to 27° C.

In addition, the first time period may be at least 30 seconds, and the second time period may be up to 300 seconds.

In addition, the first time may be a time required for the skin to maintain the target temperature for at least 29 seconds, and the second time may be a time required for the skin to maintain the target temperature for up to 120 seconds.

In addition, the phase change material may be composed of phase change material microcapsules containing the phase change material.

In addition, the cooling layer may include a thermochromic pigment that has a specific color at a temperature lower than the melting point and becomes transparent when the temperature of the cooling layer reaches the melting point.

In addition, the cooling layer may include a first cooling layer disposed on the contact layer and including a first phase change material having a first melting point, and a second cooling layer disposed on the first cooling layer and having a second phase change material having a different melting point.

In addition, the first melting point may be a temperature lower than the second melting point.

In addition, the duration time for which the first melting point is maintained may be different from the duration time for which the second melting point is maintained.

In addition, a duration time for which the first melting point is maintained may be shorter than a duration time for which the second melting point is maintained.

In addition, the cooling layer may include a plurality of cooling regions, including a phase change material having a different melting point, and the plurality of cooling regions may be arranged to respectively correspond to parts having similar temperatures among a plurality of parts forming a face part.

In addition, the plurality of cooling regions may include a phase change material having a lower melting point as the cooling part corresponding to a part having a higher temperature among the plurality of parts forming the face part.

In addition, the plurality of cooling regions may have a longer duration time in which melting points are maintained as a cooling region corresponding to a part having a higher temperature among the plurality of parts forming the face part is increased.

In addition, the contact layer may be coated with a coating solution containing a functional material for an incidental skin improvement effect.

The mask for whitening skin further comprises a temperature indicating device disposed of in contact with the cooling layer to measure the temperature of the cooling layer, wherein the temperature indicating device may include a temperature sensor for measuring the temperature of the cooling layer, a communication unit that communicates with the terminal of the user and a control unit that controls the terminal of the user to notify the terminal of attachment/detachment of the mask based on the temperature measured by the temperature sensor.

According to another aspect of the present specification, there may be provided a device for whitening skin, the device comprising a contact layer having a lower portion in contact with a body surface of a user, and provided as a flexible material for a tight-contact between the lower portion and the body surface, a cooling layer disposed on an upper part of the contact layer and including a phase change material that prepared in a state of being cooled to a melting point or less and applying negative heat to the user's skin using latent heat at the melting point for a duration of time when the melting point is maintained through the contact layer—the phase change material has a melting point below a target temperature at which pigmentation by melanocyte is suppressed, and has a mass that maintains the duration longer than a first time required for suppressing pigmentation and shorter than a second time during which damage to the skin occurs, and an outer cover disposed on the upper part of the cooling layer, and provided as an insulating material so that negative heat of the cooling layer does not leak to the outside.

According to another aspect of the present specification, there may be provided a method for whitening skin, the method comprising a mask for whitening skin, wherein the mask includes a contact layer having a lower portion in contact with a face surface of a user, and provided as a flexible material, a cooling layer including a phase change material disposed on an upper part of the contact layer and prepared in a state of being cooled to a melting point or less, provided in a shape corresponding to the user's face, and an outer cover provided as an insulating material. The method comprises: cooling the cooling layer below the melting point of the phase change material; placing the skin whitening mask on the user's face so that the lower part of the contact layer is in close contact with the face; suppressing the pigmentation of the face adhered to the lower part of the contact layer closely, wherein negative heat is applied to the user's skin by using latent heat at the melting point of the phase change material for at least a period of time when the melting point is maintained longer than a first time required to suppress the pigmentation through the contact layer; and preventing damage to the face as the phase change of the phase change material ends before a second time in which damage to the skin occurs elapses.

Hereinafter, a mask for whitening skin 10 according to an embodiment of the present specification will be described.

FIG. 1 is a view illustrating a state in which a user uses a mask for whitening skin according to an embodiment of the present specification.

Referring to FIG. 1, the mask for whitening skin 10 may have various effects on the skin of a user by cooling the skin of the user through a thermoelectric module 30 positioned therein.

For example, by cooling the skin of the user at a temperature for suppressing pigmentation by melanocytes during a predetermined interval through the thermoelectric module 30 positioned therein, the mask for whitening skin 10 may reduce the amount of melanin produced from the melanocytes, reduce the amount of melanin transferred onto the skin, and whiten the skin of the user.

In addition, by cooling the skin of the user at a temperature at which it is possible to obtain additional effects during a predetermined interval through the thermoelectric module 30 positioned therein, the mask for whitening skin 10 may have additional effects, such as reduction of swelling and lipolysis, on the skin of the user.

In addition, by cooling the skin of the user within an activation temperature range of a functional material 21 during a predetermined interval through the thermoelectric module 30 positioned therein, the mask for whitening skin 10 may increase the activity of the functional material 21 that improves the facial skin of the user.

In addition, the mask for whitening skin 10 may have a shape corresponding to a facial region in order to be adhered to the facial region and evenly cool the skin of the user and may be provided in a form in which holes are formed around the eyes and lips because the eye and lip areas of the user are vulnerable to low temperature. For reasons such as improving adhesiveness, for convenience, the mask for whitening skin 10 may be provided in a form in which a hole is also formed around the nose area.

In addition, when a weight of the mask for whitening skin 10 is heavy due to a heat dissipation layer 40, the mask for whitening skin 10 may be used while the user is lying down. However, the present specification is not limited thereto.

Figure 2:
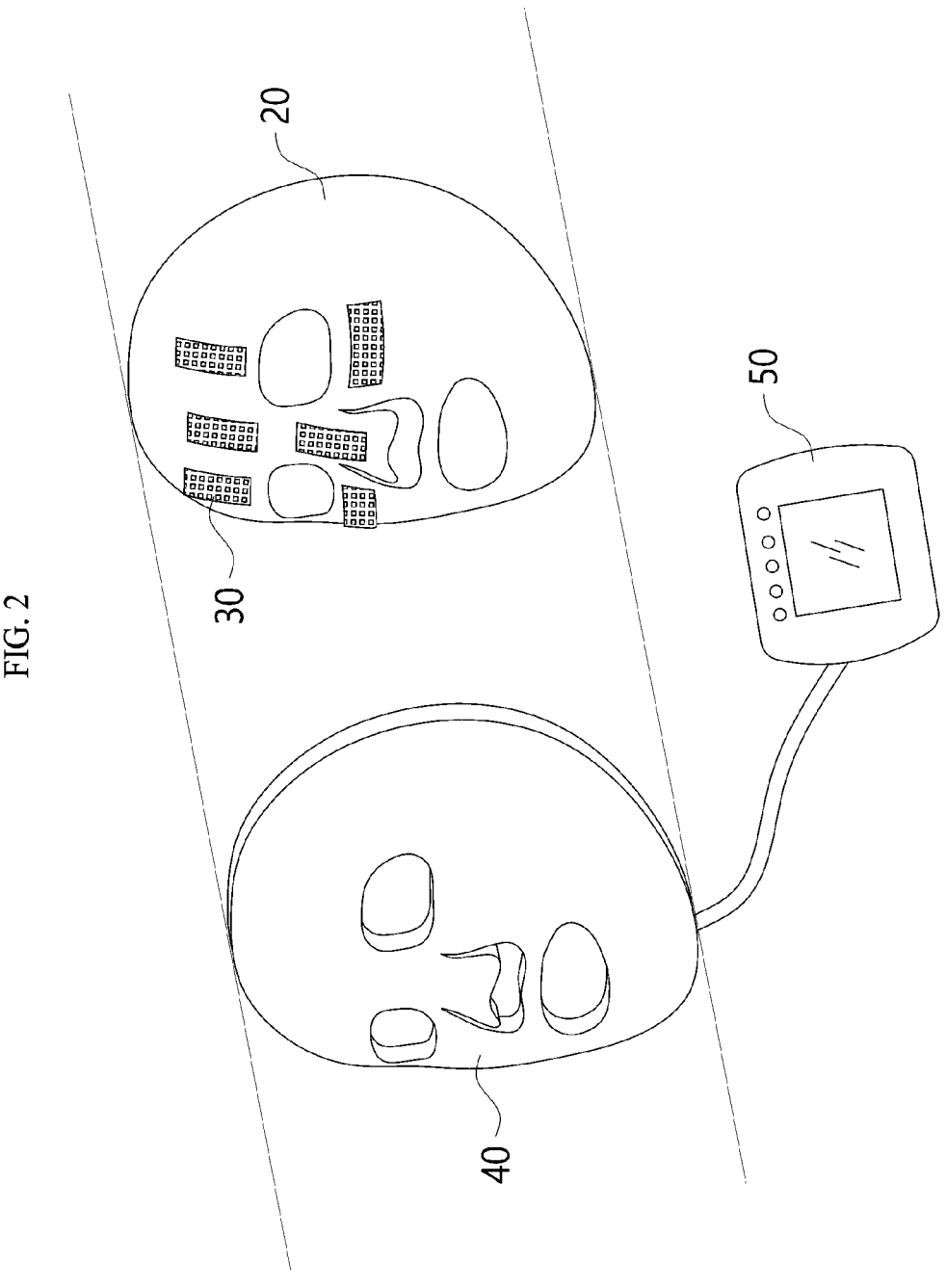
FIG. 2 is an exploded perspective view of the skin whitening mask according to an embodiment of the present specification.

FIG. 2 is an exploded perspective view of the mask for whitening skin according to an embodiment of the present specification.

Referring to FIG. 2, the mask for whitening skin 10 may include a contact layer 20, at least one thermoelectric module 30, a heat dissipation layer 40, and a controller 50.

The contact layer 20 may have a lower portion coming in contact with a face of a user and be provided with a flexible material so as to be tightly contacted to the face. Also, the contact layer 20 may be provided with a material with high thermal conductivity in order to increase efficiency of cooling the skin of the user through the thermoelectric module 30. For example, the contact layer 20 may be provided with a material such as cotton, bio cellulose, and hydrogel.

In addition, the contact layer 20 may be provided with a small thickness so that negative heat is easily applied from the thermoelectric module 30 to the skin of the user. For example, the contact layer 20 may be provided with a thickness within 1 cm.

In addition, the contact layer 20 may be provided in a shape corresponding to the face of the user. Because the eye and lip areas of the user are vulnerable to low temperature, the contact layer 20 may be provided in a form in which holes are formed around the eyes and lips. For reasons such as improving adhesiveness, for convenience, the contact layer 20 may be provided in a form in which a hole is also formed around the nose area.

In addition, in order to improve the adhesiveness with the skin, the contact layer 20 may be provided together with a liquid that has viscosity. For example, the contact layer 20 may be provided in a state in which it is soaked with emulsion that has viscosity.

In addition, in order to obtain additional skin improvement effects, various functional materials 21 may be accommodated in the contact layer 20. For example, the contact layer 20 may be coated with a coating liquid that contains the functional material 21.

The functional material 21 is a material that has an effect of improving skin, and, for example, the functional material 21 may include an ingredient that helps protect against UV rays, an ingredient that prevents oxidation, an ingredient that conditions the skin, an ingredient that inhibits the action of bacteria, an ingredient that whitens the skin (arbutin, niacinamide, ascorbyl glucoside, or the like), an ingredient that reduces the size of pores, an ingredient that reduces wrinkles (retinol, adenosine, or the like), an ingredient that revitalizes the skin, an ingredient that prevents burning sensation, an ingredient that relieves pain, and the like. In addition, the functional material 21 may be formed of at least one of an ingredient that helps protect against UV rays, an ingredient that prevents oxidation, an ingredient that conditions the skin, an ingredient that inhibits the action of bacteria, an ingredient that whitens the skin, an ingredient that reduces the size of pores, an ingredient that reduces wrinkles, an ingredient that revitalizes the skin, an ingredient that prevents burning sensation, and an ingredient that relieves pain or a mixture of two or more thereof.

In addition, the contact layer 20 may be provided in various forms. The contact layer 20 may be provided so as to be fixed at the mask for whitening skin 10. Alternatively, the contact layer 20 may be provided so as to be temporarily disposed between the thermoelectric module 30 and the skin of the user when the mask for whitening skin 10 is worn. That is, the contact layer 20 may be independently configured with a structure that is attachable to or detachable from the mask 10 and may be separable from the mask 10.

For example, the contact layer 20 may be provided as an independent sheet that is disposed between the thermoelectric module 30 and the skin of the user when the mask for whitening skin 10 is worn. As another example, the contact layer 20 may be provided in the form of independent gel that is coated between the thermoelectric module 30 and the skin of the user when the mask for whitening skin 10 is worn.

When the contact layer 20 of the mask 10 is arbitrarily replaced by the user with another contact layer 20 which accommodates a functional material 21 that has side effects at low temperatures, irritation, damage, and the like may occur to the skin of the user as the skin of the user is cooled by the mask 10.

Therefore, according to an embodiment of the present specification, an identification tag 22 may be disposed at the contact layer 20 as a means for identifying the contact layer 20.

Figure 3:
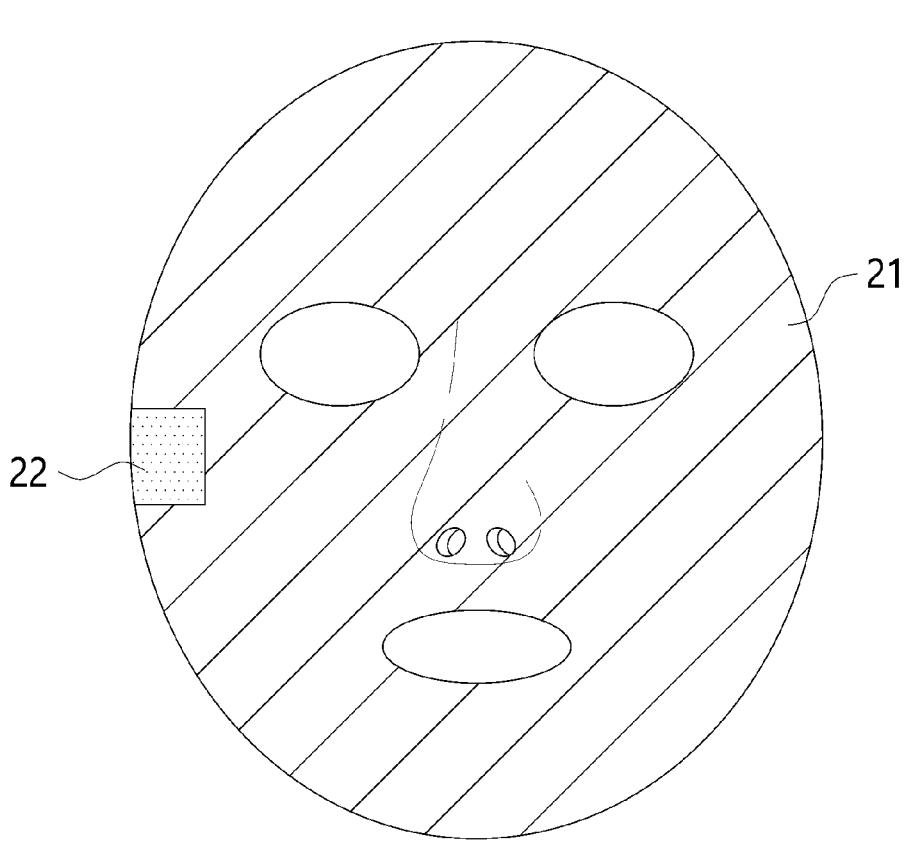
FIG. 3 is a view illustrating a contact layer at which an identification tag is disposed according to an embodiment of the present specification.

FIG. 3 is a view illustrating a contact layer at which an identification tag is disposed according to an embodiment of the present specification.

Referring to FIG. 3, the identification tag 22 may be disposed at the contact layer 20 as a means for identifying the contact layer 20.

The identification tag 22 may be disposed at any position on the contact layer 20 or may be disposed at a position corresponding to a site where a tag recognition module 74 configured to recognize the identification tag 22 is installed.

For example, the identification tag 22 may be provided as an electrically erasable programmable read-only memory (EEPROM), a radio-frequency identification (RFID) tag, or the like.

The identification tag 22 may have data relating to the contact layer 20 on which the identification tag 22 is disposed.

The identification tag 22 may have identification data relating to the contact layer 20 on which the identification tag 22 is disposed. For example, the controller 50 may control the thermoelectric module 30 so that power is applied to the thermoelectric module 30 only when the identification tag 22 is recognized by the tag recognition module 74 and the contact layer 20 is identifiable. That is, when the identification tag 22 is not recognized by the tag recognition module 74, the controller 50 may control so that power is not applied to the thermoelectric module 30.

The identification tag 22 may have identification data relating to the functional material 21 accommodated in the contact layer 20 on which the identification tag 22 is disposed. For example, when the identification tag 22 is recognized by the tag recognition module 74, the controller 50 may identify the functional material 21 accommodated in the contact layer 20 through the identification data that the identification tag 22 has.

The identification tag 22 may have data relating to a cooling condition of the thermoelectric module 30 (a cooling condition of a first major surface 31) that corresponds to the identification data relating to the functional material 21 accommodated in the contact layer 20 on which the identification tag 22 is disposed. For example, when the identification tag 22 is recognized by the tag recognition module 74, the controller 50 may obtain the data relating to the cooling condition of the thermoelectric module 30 (the cooling condition of the first major surface 31) that corresponds to the identification data that the identification tag 22 has and control the thermoelectric module 30 according to the obtained cooling condition.

The at least one thermoelectric module 30 may be formed to generate heat or absorb heat as power is applied thereto. For example, as power is applied thereto, the at least one thermoelectric module 30 may apply negative heat to the skin of the user via the contact layer 20.

A thermoelectric module may refer to a module that performs a thermoelectric operation, such as a power generating operation using a temperature difference or a heating/cooling operation using electrical energy, by using thermoelectric effects such as the Seebeck effect and the Peltier effect. Generally, most thermoelectric modules are provided in the form in which thermoelectric elements formed of n-type and p-type semiconductors are electrically connected on a flat substrate formed of ceramic material. However, in the present specification, the thermoelectric module 30 may include a thermoelectric module having flexibility. A thermoelectric element may be an element that causes thermoelectric effects such as the Seebeck effect and the Peltier effect.

Fundamentally, the thermoelectric element may include dissimilar materials constituting a thermoelectric couple that causes the thermoelectric effects. The thermoelectric couple may generate a temperature difference when electrical energy is applied thereto and, conversely, produce electrical energy when a temperature difference is applied thereto. Examples of the thermoelectric element may include a bismuth-antimony couple. Also, a pair of n-type semiconductor and p-type semiconductor may be mainly used as the thermoelectric element.

The at least one thermoelectric module 30 may have two major surfaces including the first major surface 31 disposed in contact with an upper portion of the contact layer 20 and a second major surface 32 positioned opposite to the first major surface 31. For example, the at least one thermoelectric module 30 may have two major surfaces 31 and 32 including the first major surface 31 disposed in contact with the upper portion of the contact layer 20 and the second major surface 32 positioned opposite to the first major surface 31 and, as power is applied, cool the first major surface 31 and apply negative heat to the skin of the user via the contact layer 20.

The pair of major surfaces 31 and 32 may include the first major surface 31 and the second major surface 32 which are disposed to be spaced apart to face each other. The first major surface 31 and the second major surface 32 may support a thermoelectric element or an electrode disposed therebetween. Also, the first major surface 31 and the second major surface 32 may perform a function of protecting a thermoelectric element or an electrode therein from the outside.

Also, the pair of major surfaces 31 and 32 may be provided with a material that facilitates heat conduction. For example, the pair of major surfaces 31 and 32 may be substrates formed of a copper material.

In addition, the at least one thermoelectric module according to an embodiment of the present specification may be provided as a flexible thermoelectric module 30 that has flexibility. In order to be adhered well to the face of the user, the mask 10 may be manufactured in a complex shape that is curved or the like (e.g., a shape corresponding to the face). When the flexible thermoelectric module 30 is used, it is possible to reduce difficulties in manufacturing and provide the mask 10 having a shape that allows it to be adhered better to the face.

To this end, the pair of major surfaces 31 and 32 and the inside thereof of the thermoelectric module 30 may be provided with a material having flexibility. For example, the pair of major surfaces 31 and 32 may be polyimide (PI) films. Although thermal conductivity thereof is not that high, the PI film may be advantageous for heat conduction because it has high flexibility and may be manufactured with a small thickness.

Because a plurality of areas constituting a human body part have different skin characteristics, it is necessary to cool the respective areas of the body part differently. For example, conditions under which skin damage or suppression of pigmentation occurs may be different in a plurality of areas constituting the facial region. Therefore, according to an embodiment of the present specification, the plurality of thermoelectric modules 30 may be classified into a plurality of thermoelectric module groups 33, and the plurality of thermoelectric module groups 33 may be controlled by the controller 50 separately of other thermoelectric module groups 33. The thermoelectric module groups 33 may be formed of at least one thermoelectric module 30. Here, the plurality of thermoelectric module groups 33 may be divided corresponding to areas of the face of the user.

Figure 4:
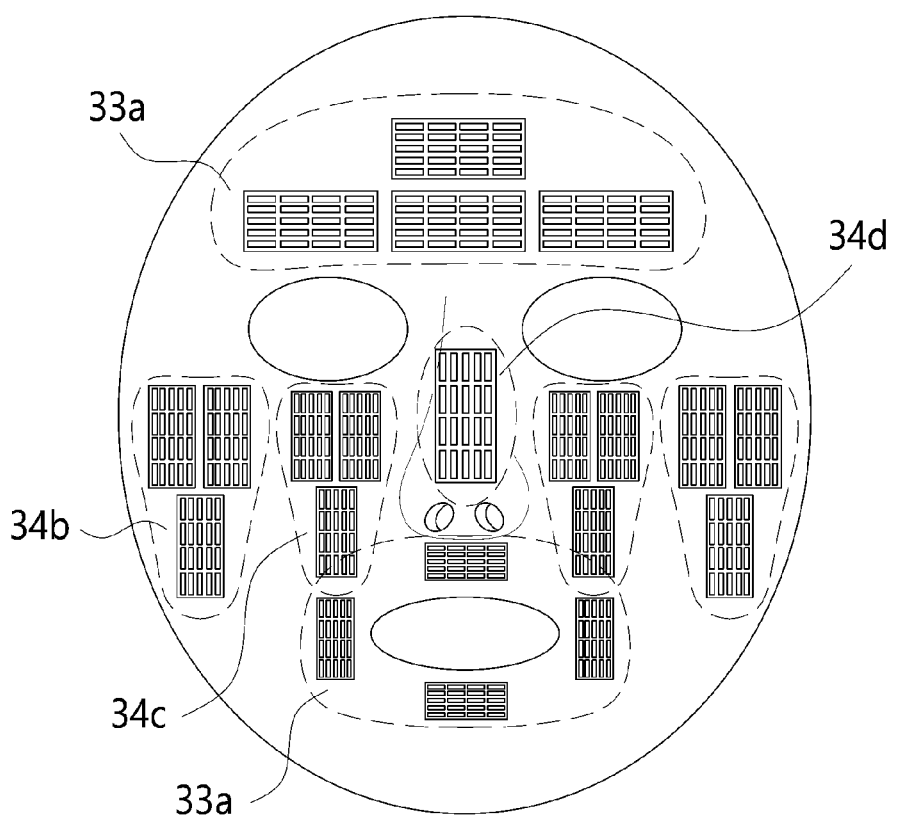
FIG. 4 is a view illustrating thermoelectric modules disposed inside a mask according to an embodiment of the present specification.

FIG. 4 is a view illustrating thermoelectric modules disposed inside a mask according to an embodiment of the present specification.

Referring to FIG. 4, a plurality of thermoelectric modules 30 may be classified into a plurality of thermoelectric module groups 33*a*, 33*b*, 33*c*, and 33*d*, corresponding to areas of the face of the user.

The thermoelectric module groups 33*a*, 33*b*, 33*c*, and 33*d* may be divided according to areas of the face of the user in which the thermoelectric module groups 33*a*, 33*b*, 33*c*, and 33*d* are disposed. For example, the thermoelectric module groups 33*a*, 33*b*, 33*c*, and 33*d* may be divided corresponding to areas with similar temperatures among areas constituting the face of the user.

Unlike the internal temperature of the human body which is in a range of 36° C. to 37° C., temperatures in a range of about 32° C. to 34° C. are distributed on the human skin. The temperature distribution on each area constituting the facial region of a person may vary among individuals. However, generally, the temperature distribution on the facial region is vertically symmetrical according to the shape in which blood vessels are distributed, and the facial region may be divided into a few regions with similar temperatures according to whether the temperature is high or low. The forehead area has a high temperature because there are many blood vessels and heat is unable to escape due to hair, and the jaw area has a high temperature because many blood vessels are distributed therearound. The areas at both sides of the nose have a relatively high temperature because relatively many blood vessels are distributed, and both cheek areas have a relatively low temperature because there are not many blood vessels distributed. The nose area has a lower temperature than other facial areas due to breathing in outside air. That is, generally, in the facial region of a person, the skin temperature is measured to be higher in the order of the forehead area, jaw area, areas at both sides of the nose, both cheek areas, and nose area. The facial region may be divided into the forehead area, jaw area, areas at both sides of the nose, both cheek areas, and nose area according to whether the temperature is high or low.

Therefore, according to an embodiment of the present specification, the plurality of thermoelectric modules 30 may be divided into a first thermoelectric module group 33*a* disposed in the forehead area and jaw area, a second thermoelectric module group 33*b* disposed in the areas at both sides of the nose, a third thermoelectric module group 33*c* disposed in both cheek areas, and a fourth thermoelectric module group 33*d* disposed in the nose area.

The plurality of thermoelectric module groups 33*a*, 33*b*, 33*c*, and 33*d* may be controlled by the controller 50 separately of other thermoelectric module groups 33*a*, 33*b*, 33*c*, and 33*d*. For example, the controller 50 may control the plurality of thermoelectric modules 30 such that the on/off, cooling interval, cooling temperature, operation mode, and the like of the plurality of thermoelectric module groups 33*a*, 33*b*, 33*c*, and 33*d* are controlled independently of those of other thermoelectric module group 33*a*, 33*b*, 33*c*, and 33*d*.

Regarding the plurality of thermoelectric module groups 33*a*, 33*b*, 33*c*, and 33*d*, a temperature at which the thermoelectric module group 33 is cooled may be lower in the thermoelectric module group 33 disposed in an area with a higher temperature in the facial region. That is, the controller 50 may control the plurality of thermoelectric module groups 33*a*, 33*b*, 33*c*, and 33*d* such that the temperature at which the first major surface 31 is cooled is lower in the thermoelectric module group 33 disposed in an area with a higher temperature in the facial region.

For example, the first major surface 31 of the first thermoelectric module group 33*a* disposed in the forehead and jaw areas which have high temperatures may be cooled at −15° C., and the first major surface 31 of the fourth thermoelectric module group 33*d* disposed in the nose area which has a low temperature may be cooled at 0° C.

Also, regarding the plurality of thermoelectric module groups 33*a*, 33*b*, 33*c*, and 33*d*, a cooling interval may be longer in the thermoelectric module group 33 disposed in an area with a higher temperature in the facial region. That is, the controller 50 may control the plurality of thermoelectric module groups 33*a*, 33*b*, 33*c*, and 33*d* such that the first major surface 31 is cooled for a longer interval in the thermoelectric module group 33 disposed in an area with a higher temperature in the facial region.

For example, the first thermoelectric module group 33*a* disposed in the forehead and jaw areas which have high temperatures may be cooled for a cooling interval of 120 seconds, and the fourth thermoelectric module group 33*d* disposed in the nose area which has a low temperature may be cooled for a cooling interval of 60 seconds.

However, the above-described thermoelectric module groups 33 are not limited thereto. There may be more or less thermoelectric module groups 33 than the above-described thermoelectric module groups 33, and each thermoelectric module group 33 is not limited by the above description.

Also, according to an embodiment of the present specification, one or more thermoelectric modules 30 may be disposed inside the mask 10 such that a separation distance therebetween is adjusted.

Figure 5:
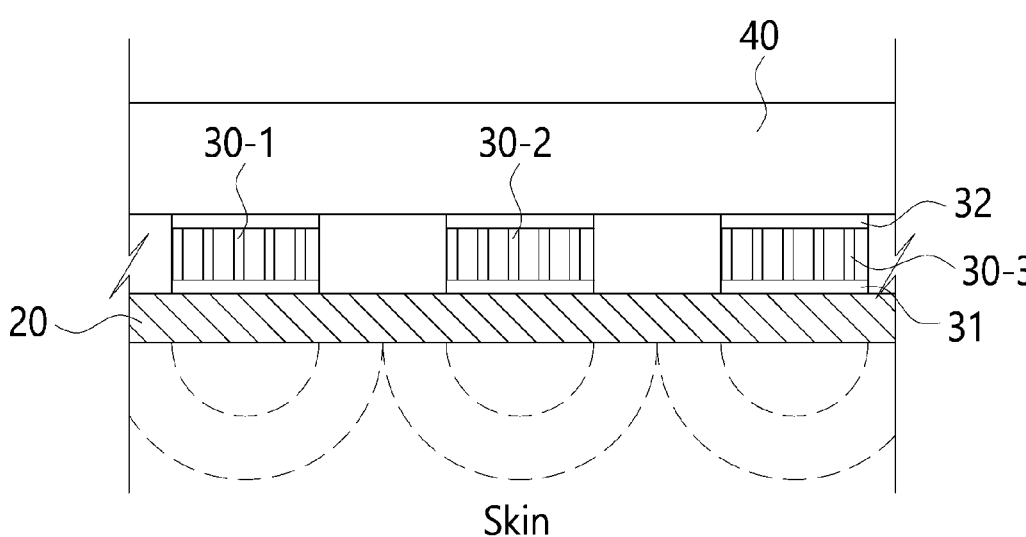
FIG. 5 illustrates a state in which negative heat of the mask is transferred to the skin according to an embodiment of the present specification.

FIG. 5 illustrates a state in which negative heat of the mask is transferred to the skin according to an embodiment of the present specification.

The negative heat of the first major surface 31 of the thermoelectric module 30 is applied to the skin of the user via the contact layer 20. When the negative heat applied to the skin is transferred within the skin, the negative heat is transferred in a spherical shape.

Referring to FIG. 5, it can be seen that the negative heat is transferred in a semi-spherical shape to the skin from the thermoelectric module 30. That is, the skin temperature at a site at which the thermoelectric module 30 is disposed becomes different from the skin temperature at a site at which the thermoelectric module 30 is not disposed.

In a case in which a plurality of thermoelectric modules 30-1, 30-2, and 30-3 are disposed in the mask 10, when a separation distance between the thermoelectric modules 30-1, 30-2, and 30-3 is too long, the negative heat may not be properly transferred to some portions between the thermoelectric modules 30-1, 30-2, and 30-3, and whitening may occur partially, causing uneven skin tone. In order to prevent whitening from occurring partially, in the case in which the plurality of thermoelectric modules 30-1, 30-2, and 30-3 are disposed, the separation distance between the thermoelectric modules 30-1, 30-2, and 30-3 may be adjusted.

The plurality of thermoelectric modules 30-1, 30-2, and 30-3 may be disposed to be spaced apart at a separation distance that allows the negative heat to be applied to sites in between the thermoelectric modules 30-1, 30-2, and 30-3. For example, the plurality of thermoelectric modules 30-1, 30-2, and 30-3 may be disposed such that a separation distance between the thermoelectric modules 30-1, 30-2, and 30-3 is in a range of 1 mm to 50 mm.

The plurality of thermoelectric modules 30-1, 30-2, and 30-3 may be disposed on the basis of the skin temperatures at the sites in between the thermoelectric modules 30-1, 30-2, and 30-3 upon cooling and the skin temperatures at the sites at which the thermoelectric modules 30-1, 30-2, and 30-3 are disposed upon cooling.

The plurality of thermoelectric modules 30-1, 30-2, and 30-3 may be disposed to be spaced apart at a separation distance that allows a difference between the skin temperatures at the sites in between the thermoelectric modules 30-1, 30-2, and 30-3 upon cooling and the skin temperatures at the sites at which the thermoelectric modules 30-1, 30-2, and 30-3 are disposed upon cooling to be a predetermined temperature or less. For example, the first thermoelectric module 30-1 and the second thermoelectric module 30-2 may be disposed to be spaced apart at a separation distance that allows a difference between the skin temperature at a site in between the first thermoelectric module 30-1 and the second thermoelectric module 30-2 and the skin temperature at any one of a site at which the first thermoelectric module 30-1 is disposed and a site at which the second thermoelectric module 30-2 is disposed to be 10° C. or less.

As is well-known, when heat absorption occurs on one side of a thermoelectric element, heat generation occurs on the other side, and vice versa. For example, when heat absorption occurs on the first major surface 31 of the thermoelectric module 30 in order to cool the skin of the user, heat generation occurs on the second major surface 32 side of the thermoelectric module 30. When dissipation of the heat generated on the second major surface 32 side is not performed properly, the amount of power applied to the mask 10 may increase, and the cooling efficiency at the first major surface 31 may decrease. Therefore, the mask 10 may include the heat dissipation layer 40 configured to receive heat generated upon cooling of the first major surface 31 and dissipate the received heat.

The heat dissipation layer 40 may be disposed at an upper portion of the thermoelectric module 30 so as to come in contact with the second major surface 32 of the thermoelectric module 30 and may receive, via the second major surface 32, the heat generated upon the cooling of the first major surface 31 and dissipate the received heat. For example, the heat dissipation layer 40 may be formed of a material with high specific heat or thermal conductivity, or a fluid circulator, a fan, or the like that exchanges heat through a circulating fluid may be installed in the heat dissipation layer 40. Various heat dissipation means may be configured or installed in combination in the heat dissipation layer 40.

Also, in order to increase an area coming in contact with the outside so that heat dissipation is enhanced, the heat dissipation layer 40 may be provided in the shape protruding in a concavo-convex structure in which sides of the heat dissipation layer 40 coming in contact with the outside alternately protrude and indent.

Also, the heat dissipation layer 40 may be formed of a structure that is configured independently and is replaceable or detachable.

Generally, a temperature difference between a heat absorbing surface and a heat generating surface of a thermoelectric module has a characteristic of converging within a range of about 30° C. to less than 55° C. as power is applied. That is, when power is continuously applied to a thermoelectric module, a temperature difference between a heat absorbing surface and a heat generating surface of the thermoelectric module is maintained within the range of about 30° C. to less than 55° C. Therefore, when the temperature of the heat generating surface of the thermoelectric module is excessively high, the temperature of the heat absorbing surface of the thermoelectric module also increases, and a problem may occur in which the mask 10 is unable to cool the skin of the user at a target cooling temperature. In order to maintain the temperature difference between the heat absorbing surface and the heat generating surface within the range of about 30° C. to less than 55° C. and allow the thermoelectric module to be continuously used for cooling the skin of the user, the mask 10 may include the heat dissipation layer 40 configured to maintain the temperature difference between the first major surface 31 and the second major surface 32 to be a predetermined temperature or less (e.g., within the range of about 30° C. to less than 55° C.).

Therefore, according to an embodiment of the present specification, the heat dissipation layer 40 may be provided as a phase-change material heat dissipation layer 40a which is disposed at an upper portion of the thermoelectric module 30 so as to come in contact with the second major surface 32 of the thermoelectric module and includes a phase-change material (PCM) which receives, via the second major surface 32, heat generated upon cooling of the first major surface 31 and absorbs the received heat and maintains the temperature of the second major surface 32 constant using latent heat at a melting point in order to maintain a difference between a temperature of the first major surface 31 and a temperature of the second major surface 32 to be less than a predetermined temperature.

A phase-change material is a material that has a large amount of latent heat, thus being capable of storing and releasing a large amount of energy upon a phase change. The phase-change material is a material that accumulates or releases heat through a process of changing from one phase to another, e.g., from solid to liquid, from liquid to solid, and the like. When the outside temperature drops below a melting point of the phase-change material, the phase-change material releases a large amount of latent heat as a phase change occurs. When the outside temperature rises to above the melting point of the phase-change material, the phase-change material absorbs a large amount of latent heat as a phase change occurs. Therefore, because the phase-change material absorbs or releases a large amount of heat as a phase change of the material occurs, the phase-change material is able to maintain a temperature corresponding to the melting point constant for a long period as compared with other materials. By using the phase-change material, the phase-change material heat dissipation layer 40a may maintain the temperature of the second major surface 32 constant and maintain the difference between the temperature of the first major surface 31 and the temperature of the second major surface 32 to be less than a predetermined temperature. Here, an appropriate value within the range of 30° C. to less than 55° C. may be selected as the predetermined temperature.

The phase-change material heat dissipation layer 40a may include a phase-change material that has a melting point within a specific range in order to maintain the difference between the temperature of the first major surface 31 and the temperature of the second major surface 32 to be less than a predetermined temperature. For example, the phase-change material heat dissipation layer 40a may include a phase-change material that has a melting point in a range of −15° C. to 40° C., such as $C_{12}H_{26}$, $C_{16}H_{34}$, and $C_{20}H_{42}$.

Also, the phase-change material heat dissipation layer 40a may include a phase-change material that has a mass determined on the basis of input power and use time of the thermoelectric module 30, an amount of heat absorbed by the first major surface 31, and the latent heat at the melting point of the phase-change material.

For example, a mass G of a phase-change material included in the phase-change material heat dissipation layer 40a may be determined by Equation 1 below.

$$G = \frac{(Q_c + P) \cdot t}{(\Delta H)} \qquad \text{(Equation 1)}$$

Here, $Q_c$ represents the amount of heat absorbed by the first major surface 31, P represents the input power of the thermoelectric module 30, t represents the use time of the thermoelectric module 30, and ΔH represents the latent heat at the melting point of the phase-change material.

The amount of heat $Q_c$ absorbed by the first major surface 31 may be defined as a size of the quantity of heat absorbed per unit time by the first major surface 31 of the thermoelectric module 30.

For example, when the quantity of heat $Q_c$ absorbed by the first major surface 31 is 3000 J/sec, the input power P of the thermoelectric module 30 is 2.3 W, the use time t of the thermoelectric module 30 is 40 seconds, and the latent heat ΔH at the melting point of the phase-change material is 230 J/g, according to Equation 1 above, the mass G of the phase-change material included in the phase-change material heat dissipation layer 40a is obtained as follows: G=(3000 2.3)×40/230=522.14 g.

Note that a method of determining the mass of the phase-change material included in the phase-change material heat dissipation layer 40a is not limited to the above-described method, and the mass may be determined using various other methods.

Also, the phase-change material heat dissipation layer 40a may be formed of a structure that is configured independently and is replaceable or detachable. For example, the phase-change material heat dissipation layer 40a may be configured in a block shape and connected to or separated from the mask 10.

Also, the phase-change material heat dissipation layer 40a may be disposed on an upper portion of the at least one thermoelectric module 30 and disposed in a housing (not illustrated), which is provided to position the phase-change material heat dissipation layer 40a, so that the phase-change material heat dissipation layer 40a is detachable or replaceable. In this way, the phase-change material heat dissipation layer 40a may be separated from the mask 10, cooled separately, and then re-mounted on the mask 10.

Figure 6:
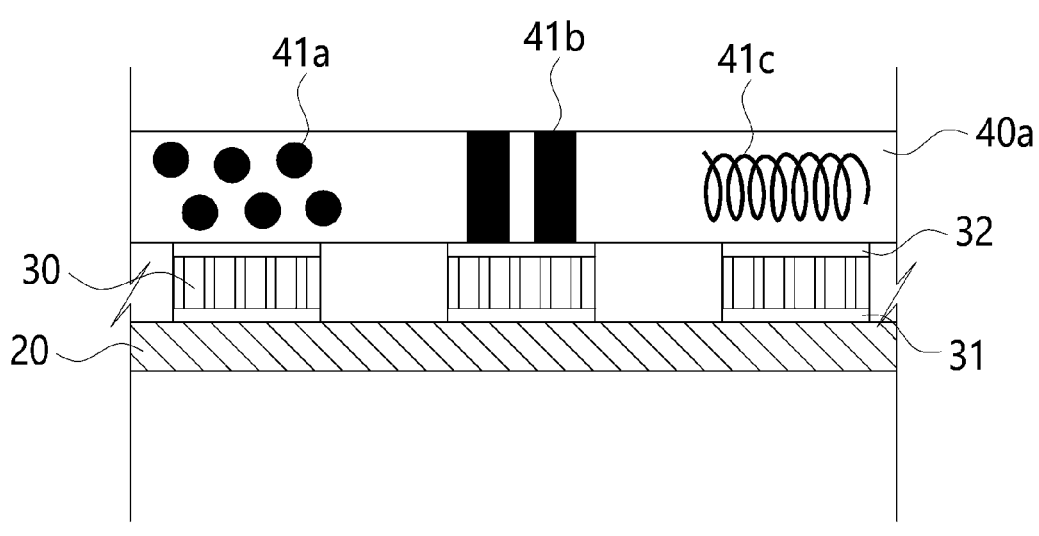
FIG. 6 illustrates a cross-sectional view of a mask including a phase-change material heat dissipation layer that has a heat transfer member according to an embodiment of the present specification.

FIG. 6 illustrates a cross-sectional view of the mask 10 including a phase-change material heat dissipation layer that has a heat transfer member according to an embodiment of the present specification.

Referring to FIG. 6, the phase-change material heat dissipation layer 40a may include a heat transfer member 41 formed of a material with high thermal conductivity so that a heat exchange is facilitated inside the phase-change material heat dissipation layer 40a.

The heat transfer member 41 may be formed of a material with high thermal conductivity, e.g., a metal material such as aluminum and copper.

Also, the heat transfer member 41 may be provided in various forms. For example, the heat transfer member 41 may be provided in the form of a bead 41a, the form of a bar 41b that passes through the heat dissipation layer 40, or the form of a coil 41c.

Figure 7:
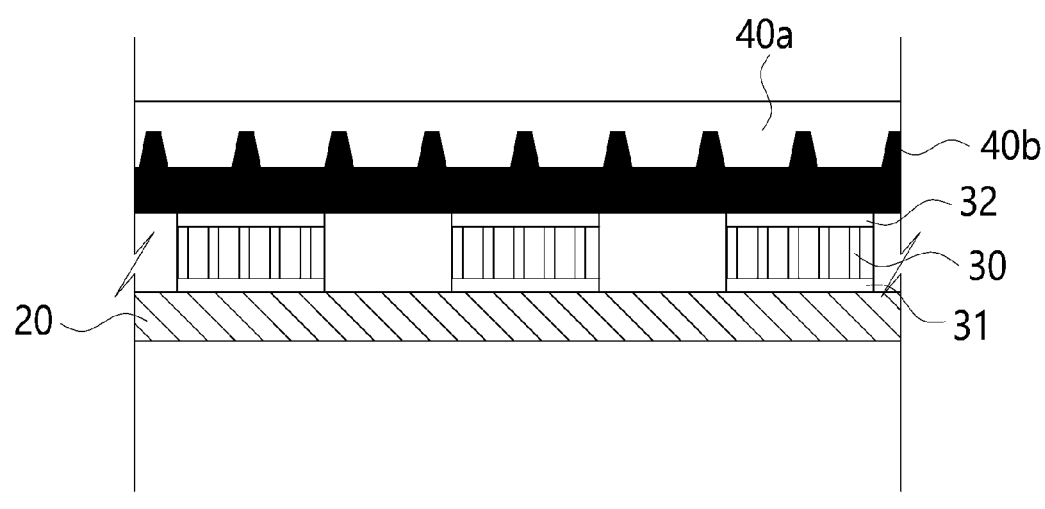
FIG. 7 illustrates a cross-sectional view of a mask including a metal heat dissipation layer according to an embodiment of the present specification.

FIG. 7 illustrates a cross-sectional view of a mask including a metal heat dissipation layer according to an embodiment of the present specification.

Referring to FIG. 7, in order to improve a heat dissipation ability of the heat dissipation layer 40, a metal heat dissipation layer 40b may be disposed between the phase-change material heat dissipation layer 40a and the thermoelectric module 30 so that one surface comes in contact with the thermoelectric module 30 and the other surface comes in contact with the phase-change material heat dissipation layer 40a.

The metal heat dissipation layer 40b may be formed of a metal material with high thermal conductivity. For example, the metal heat dissipation layer 40b may be formed of a metal material such as aluminum and copper.

Also, the surface of the metal heat dissipation layer 40b that comes in contact with the phase-change material heat dissipation layer 40a may be formed of a concavo-convex structure. For example, the metal heat dissipation layer 40b may protrude in a concavo-convex structure in which sides of the metal heat dissipation layer 40b coming in contact with the phase-change material heat dissipation layer 40a alternately protrude and indent, and the metal heat dissipation layer 40b may protrude in various shapes.

Figure 8:
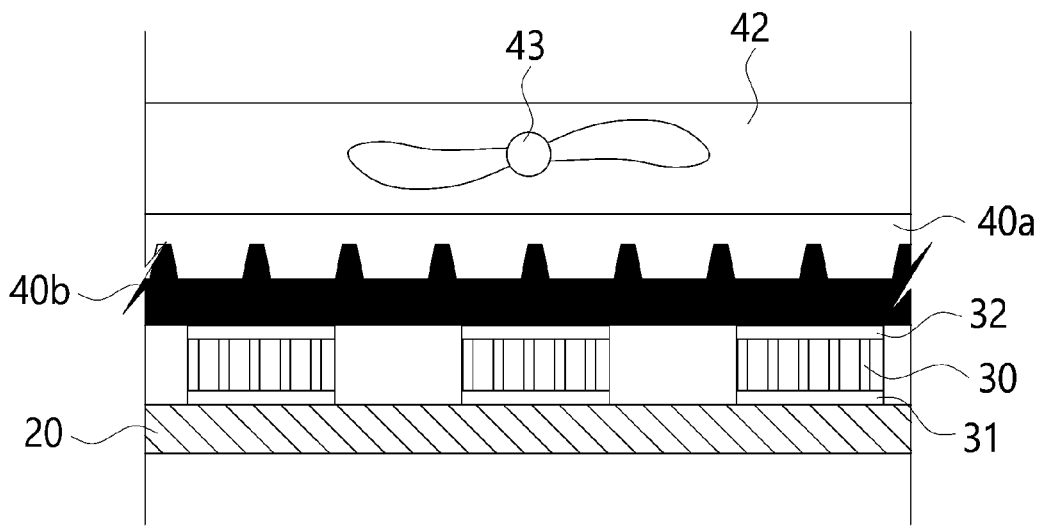
FIG. 8 illustrates a cross-sectional view of a mask including a fan according to an embodiment of the present specification.

FIG. 8 illustrates a cross-sectional view of a mask including a fan according to an embodiment of the present specification.

Referring to FIG. 8, in order to improve the heat dissipation ability of the heat dissipation layer 40, an outer cover 42 may be disposed at an upper portion of the heat dissipation layer 40, and a fan 43 may be installed in the outer cover 42.

The outer cover 42 may be formed of a material with high thermal conductivity. For example, the outer cover 42 may be formed of a metal material such as aluminum and copper.

In order to enhance heat dissipation, the fan 43 may introduce outside air, exchange heat, and discharge heat generated at the second major surface 32 to the outside. The fan 43 may be installed not only in the outer cover 42 but also in other elements of the mask 10 such as the heat dissipation layer 40.

Also, a means for heat dissipation other than the fan 43 may be additionally provided in the outer cover 42. For example, a fluid circulator (not illustrated) configured to exchange heat through a fluid may be provided in the outer cover 42.

Also, a handle (not illustrated) that allows the mask 10 to be picked up may be provided in the outer cover 42. The handle may be provided with a material with low thermal conductivity in order to prevent the user from feeling uncomfortable due to hotness when the outer cover 42 becomes hot due to heat generated from the second major surface 32. For example, the handle may be provided with a material with low thermal conductivity such as rubber. Also, the handle may be provided to be disposed in other elements of the mask 10 such as the heat dissipation layer 40 instead of being disposed in the outer cover 42.

The controller 50 may be provided in a small size that is easy for the user to carry and may be connected to the mask 10 by wire or wirelessly to control the operation of the mask 10.

Also, the controller 50 may compare a measured temperature of the first major surface 31 of the thermoelectric module 30 with a predetermined temperature and measure a difference therebetween and may control the current or voltage supplied to the thermoelectric module using various control methods including a proportional-integral-derivative (PID) control method in order to adjust a surface temperature of the first major surface 31 of the thermoelectric module 30.

For example, the controller 50 may control supply of power to at least one thermoelectric module 30 to adjust an operation mode in which a cooling temperature, a cooling interval, and the like of the first major surface 31 are set. Hereinafter, the operation mode refers to a mode in which the controller 50 controls the thermoelectric module 30 to cool the first major surface 31 according to predetermined temperature and interval.

The power supplied from the controller 50 to the thermoelectric module 30 or the like may be supplied by wire or wireless from the outside or supplied from a battery (not illustrated) separately accommodated in the mask 10.

Also, the controller 50 may be disposed inside the mask 10 or disposed at other places. Various modifications are possible.

Meanwhile, although not illustrated in the drawings, the mask for whitening skin 10 according to an embodiment of the present specification may further include additional elements.

The mask for whitening skin 10 may further include a skin temperature sensor 70 configured to measure a temperature of the skin of the user. The skin temperature sensor 70 may be disposed in any place, e.g., the contact layer 20, the thermoelectric module 30, the heat dissipation layer 40, the outer cover 42, or the like, which comes in contact with the skin of the user and at which it is possible to measure the temperature of the skin of the user. For example, the skin temperature sensor 70 may be disposed in the contact layer 20.

For example, the skin temperature sensor 70 may be a sensor such as a liquid expansion temperature sensor, a state change temperature sensor, a thermocouple, and a resistance temperature detector (RTD).

Also, the mask for whitening skin 10 may further include a second major surface temperature sensor 71 configured to measure a temperature of the second major surface 32 of the thermoelectric module 30. The second major surface temperature sensor 71 may be disposed in any place, e.g., the contact layer 20, the thermoelectric module 30, the heat dissipation layer 40, the outer cover 42, or the like, which comes in contact with the second major surface 32 and at which it is possible to measure the temperature of the second major surface 32. For example, the second major surface temperature sensor 71 may be disposed in the second major surface 32.

The second major surface temperature sensor 71 may be a sensor such as a liquid expansion temperature sensor, a state change temperature sensor, a thermocouple, and an RTD.

Also, the mask for whitening skin 10 may further include a vibration generating module 72 configured to output vibration. The vibration generating module 72 may be disposed in any place, e.g., the contact layer 20, the thermoelectric module 30, the heat dissipation layer 40, the outer cover 42, or the like, at which it is possible to apply vibration to the face of the user. For example, the vibration generating module 72 may be installed to be attached to the thermoelectric module 30. For example, the vibration generating module 72 may be provided as an oscillator, a vibration motor, a haptic device, or the like.

The vibration generating module 72 may output vibration for notifying the user. For example, when the cooling of the first major surface 31 is completed (e.g., when the operation mode is ended), the vibration generating module 72 may output vibration for notifying that the cooling is ended.

Also, the vibration generating module 72 may output vibration for alleviating pain of the user while the skin of the user is being cooled. For example, the vibration generating module 72 may output vibration (e.g., a vibration massage) and apply the vibration to the skin of the user while the thermoelectric module 30 applies negative heat to the skin of the user.

The vibration generating module 72 may output stronger vibration as the intensity of negative heat that the thermoelectric module 30 applies to the skin of the user is higher (i.e., the cooling temperature of the first major surface 31 is lower or the cooling interval of the first major surface 31 is longer).

Also, the vibration generating module 72 may output the vibration for notifying the user and the vibration for alleviating the pain of the user in different manners.

Also, the mask for whitening skin 10 may further include a touch sensing module 73 configured to detect contact of the skin of the user with the mask 10.

The touch sensing module 73 may be disposed in any place, e.g., the contact layer 20, the thermoelectric module 30, the heat dissipation layer 40, the outer cover 42, or the like, at which it is possible to come in contact with the skin of the user. For example, the touch sensing module 73 may be disposed in the contact layer 20.

The touch sensing module 73 may generate a skin detection signal when the skin of the user is detected. Alternatively, the touch sensing module 73 may generate a skin non-detection signal when the skin of the user is not detected.

The touch sensing module 73 may be used as a means for determining a point in time at which cooling of the first major surface 31 starts. For example, the touch sensing module 73 may generate a skin detection signal upon detecting the skin of the user and transmit the corresponding signal to the controller 50, and, when the skin detection signal is received, the controller 50 may control the thermoelectric module 30 to start the cooling of the first major surface 31.

For example, the touch sensing module 73 may be formed of at least one touch sensor configured to detect contact using electrical characteristics that occur upon contact with the skin of the user or formed of a heat sensor configured to detect human heat.

Also, the mask for whitening skin 10 may further include the tag recognition module 74 configured to recognize the identification tag 22.

The tag recognition module 74 may be disposed in any place, i.e., the thermoelectric module 30, the heat dissipation layer 40, the controller 50, or the like, at which it is possible to recognize the identification tag 22. For example, the tag recognition module 74 may be installed in an inner space of the mask 10 that corresponds to a place where the identification tag 22 is positioned on the contact layer 20.

The tag recognition module 74 may recognize the identification tag 22. For example, the tag recognition module 74 may read data of the identification tag 22 disposed at the contact layer 20 and identify the identification tag 22.

The tag recognition module 74 may read or write data of the identification tag 22 disposed at the contact layer 20. For example, the tag recognition module 74 may recognize the identification tag 22 and read identification data that the identification tag 22 has, and the controller 50 may, from the identification data, identify the functional material 21 accommodated in the contact layer 20. As another example, the tag recognition module 74 may read data relating to a cooling condition of the thermoelectric module 30 (a cooling condition of a first major surface 31) that corresponds to the identification data that the identification tag 22 has, and the controller 50 may control the thermoelectric module 30 according to the cooling condition data.

The tag recognition module 74 may be provided as an RFID reader, an RFID reader writer, an EEPROM, or the like.

Also, although not illustrated in the drawings, the mask for whitening skin 10 according to an embodiment of the present specification may further include a strap, a band, or the like that provides tension so that, upon use of the mask for whitening skin 10 by the user, the mask for whitening skin 10 is adhered to the skin of the user.

Also, the mask for whitening skin 10 is not limited by the above-described configuration. The mask for whitening skin 10 may include elements more or less than those described above, and each element is not limited by the above description.

Hereinafter, the controller 50 will be described in detail.

Figure 9:
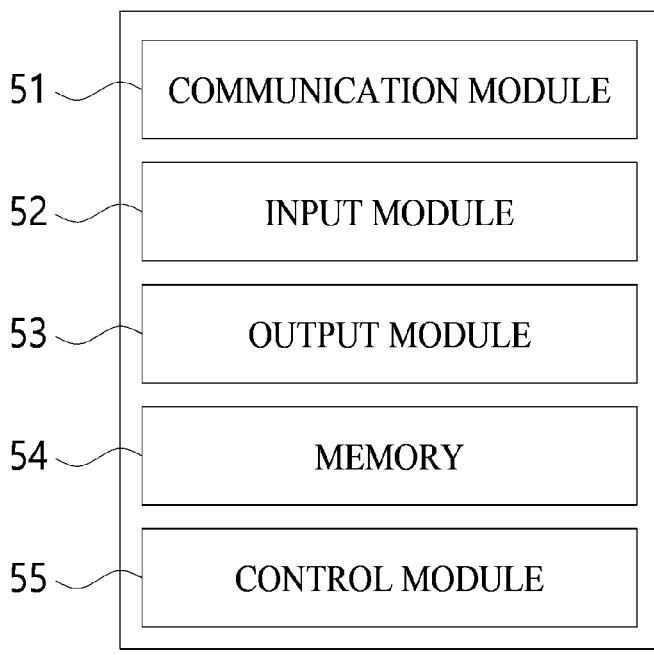
FIG. 9 is a block diagram of a controller according to an embodiment of the present specification.

FIG. 9 is a block diagram of a controller according to an embodiment of the present specification.

Referring to FIG. 9, the controller 50 according to an embodiment of the present specification may include a communication module 51, an input module 52, an output module 53, a memory 54, and a control module 55.

The communication module 51 may perform communication with an external device. For example, the controller 50 may exchange predetermined data with an external device via the communication module 51.

Specifically, the communication module 51 may exchange data relating to the operation mode with an external device.

The communication module 51 may send data relating to the operation mode that is received from the input module 52 to an external device (e.g., a server) or may obtain data relating to the operation mode from an external device (e.g., a server).

For example, the communication module 51 may obtain, from an external device, data that provides an operation mode for improving the skin of each user on the basis of results of monitoring skin conditions of the user. As another example, the communication module 51 may obtain, from an external device, data relating to an operation mode that causes the temperature to be sequentially maintained at 0° C. for 30 seconds, 5° C. for 40 seconds, and 10° C. for 60 seconds.

The communication module 51 may communicate with an external device such as another local device and/or a server. The communication module 51 may include one or more modules that allow the communication. The communication module 51 may communicate with an external device by wire or wirelessly. To this end, the communication module 51 may be formed as a wired communication module that accesses the Internet through a local area network (LAN), a mobile communication module such as a long term evolution (LTE) communication module that transmits and receives data by connecting to a mobile communication network via a mobile communication base station, a short-range communication module using a wireless local area network (WLAN)-based communication method such as Wi-Fi or a wireless personal area network (WPAN)-based communication method such as Bluetooth or ZigBee, a satellite communication module using a global navigation satellite system (GNSS) such as a global positioning system (GPS), or a combination thereof.

The input module 52 may receive a user input from a user. The user input may be in various forms such as a key input, a touch input, and a voice input. For example, the input module 52 may receive, via a key input button, a user's input on a selection of image resolution.

Also, the input module 52 may receive, from a user, data relating to a user settings operation mode. Specifically, the input module 52 may receive data relating to a cooling interval, a cooling temperature, a cooling order, a cooling area, and the like of the user settings operation mode.

For example, the input module 52 may receive, from a user, data that provides an operation mode for improving the skin of each user on the basis of results of monitoring skin conditions of the user. As another example, the input module 52 may receive data relating to an operation mode that causes the temperature to be sequentially maintained at 0° C. for 30 seconds, 5° C. for 40 seconds, and 10° C. for 60 seconds.

Typical examples of the input module 52 not only include a keypad, a keyboard, and a mouse in conventional forms, but also include a touch sensor that detects a user's touch, a microphone that receives a voice signal, a camera that recognizes a gesture or the like through image recognition, a proximity sensor formed of an illuminance sensor, an infrared sensor, or the like that detects a user's approach, a motion sensor that recognizes a user's motion through an acceleration sensor, a gyro sensor, or the like, and various other input means that detect or receive various forms of user input. Here, the touch sensor may be implemented as a piezoelectric or capacitive touch sensor that senses a touch through a touch panel or a touch film attached to a display panel, an optical touch sensor that senses a touch by an optical method, or the like.

The output module 53 may include a display that outputs an image, a speaker that outputs sound, a haptic device that generates vibration, and various other output means.

The display is a concept that encompasses image display devices in a broad sense that include a liquid crystal display (LCD), a light emitting diode (LED) display, an organic light emitting diode (OLED) display, a flat panel display (FPD), a transparent display, a curved display, a flexible display, a 3D display, a holographic display, a projector, and various other devices capable of performing an image output function. The display may also be in the form of a touch display that is integrally formed with the touch sensor of the input module 52. In addition, instead of being implemented in the form of a device that outputs information to the outside by itself, the output module 53 may be implemented in the form of an output interface (a universal serial bus (USB) port, a Personal System (PS)/2 port, or the like) that connects an external output device to an image processing device.

The memory 54 may store information relating to operation of the controller 50.

Specifically, the memory 54 may store data relating to an operation mode obtained from an external device. Also, the memory 54 may store data relating to an operation mode input from the input module 52.

For example, the memory 54 may store data that provides an operation mode for improving the skin of each user on the basis of results of monitoring skin conditions of the user. As another example, the memory may store data relating to an operation mode that causes the temperature to be sequentially maintained at 0° C. for 30 seconds, 5° C. for 40 seconds, and 10° C. for 60 seconds.

Also, the memory 54 may store an operating system (OS), firmware, middleware, and various programs that support the same for driving the controller 50 or store data or the like received from other external devices such as a user terminal.

The control module 55 may be involved in the overall operation of the elements of the controller 50. Therefore, unless otherwise stated, the operation of the controller 50 may be interpreted as being caused by the control module 55.

The control module 55 may be implemented as a computer or a similar device according to hardware, software, or a combination thereof. The hardware of the controller may be provided in the form of an electronic circuit such as a central processing unit (CPU), a micro control unit (MCU), and a chip that processes an electrical signal and performs a control function. The software of the controller may be provided in the form of a program that drives the hardware of the controller.

However, the controller 50 is not limited by the above-described configuration. The controller 50 may include elements more or less than those described above, and each element is not limited by the above description.

Hereinafter, a first embodiment in which the controller 50 controls the temperature of the first major surface 31 of the thermoelectric module 30 will be described.

First Embodiment

Figure 10:
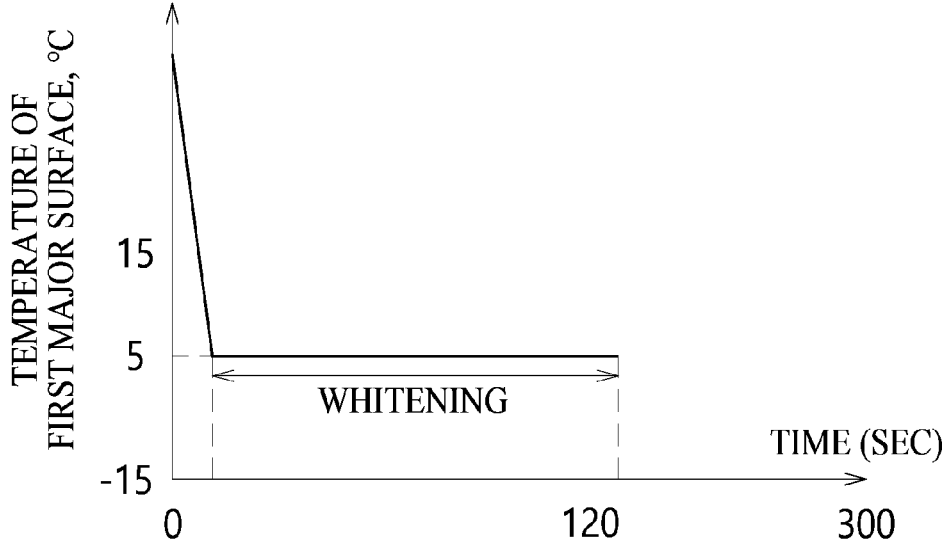
FIG. 10 is a graph showing temperature changes over time of a first major surface of a thermoelectric module according to a first embodiment of the present specification.

FIG. 10 is a graph showing temperature changes over time of a first major surface of a thermoelectric module according to a first embodiment of the present specification.

When the user's skin is cooled too much, skin damage may occur due to skin freezing or the like. When the user's skin is cooled too lightly, pigmentation by melanocytes may not be suppressed by the cooling.

Therefore, the controller 50 according to an embodiment of the present specification may control the thermoelectric module 30 in a whitening mode in which the first major surface 31 is cooled under cooling conditions for preventing skin damage while suppressing pigmentation by melanocytes. Referring to FIG. 10, it can be seen that the thermoelectric module 30 is controlled by the controller 50 and the whitening mode is performed in which the first major surface 31 is cooled for 120 seconds at a cooling temperature of 5° C.

Hereinafter, an interval during which the first major surface 31 is cooled in the whitening mode will be referred to as "whitening interval", a temperature of the first major surface 31 while the whitening mode is performed will be referred to as "whitening temperature," and a temperature range of the first major surface 31 while the whitening mode is performed will be referred to as "whitening temperature range."

The controller 50 may control the thermoelectric module 30 to cool the first major surface 31 within a specific temperature range in order to prevent skin damage due to cooling while suppressing pigmentation by melanocytes on the user's skin. For example, the controller 50 may control the thermoelectric module 30 to cool the first major surface 31 at a cooling temperature such that the skin of the user reaches a target temperature at which pigmentation by melanocytes is suppressed, wherein the cooling temperature is in a range of −15° C. to 15° C., which is a whitening temperature range, and lower than the target temperature. This is because skin damage may occur due to freezing of skin tissues when the temperature of the first major surface 31 is too low, and the effect of suppressing pigmentation by melanocytes may be small when the temperature of the first major surface 31 is too high.

Here, the target temperature may be in a range of ° C. to 27° C. Because the skin whitening effect by cooling of the skin increases as the temperature of the skin is maintained low, the target temperature may be a temperature in a range of 27° C. or lower in order for the skin whitening effect by the cooling of the skin to occur substantially. Also, although the actual freezing of human skin tissues does not occur before the skin temperature reaches a temperature in a range of −4° C. to −10° C., tissue damage may occur due to ischemia and blood clots in small blood vessels when the skin temperature drops below 4° C. Thus, the target temperature may be a temperature in a range of 4° C. or higher in order to prevent skin damage due to the cooling of the skin.

However, the cooling temperature of the first major surface 31 that is controlled by the controller 50 does not have to be limited by the above description and may vary according to circumstances. For example, the cooling temperature of the first major surface 31 may be maintained within a temperature range of −30° C. to 35° C. Also, the target temperature does not have to be limited by the above description and may vary according to circumstances. For example, the target temperature may be maintained within a temperature range of −10° C. to 35° C.

Also, in order to suppress pigmentation by melanocytes while preventing skin damage due to cooling, the controller 50 may control the thermoelectric module to maintain a whitening interval, during which the cooling of the first major surface 31 occurs, to be longer than a first interval, which is necessary for suppressing the pigmentation, and shorter than a second interval, during which skin damage begins. For example, in order to prevent skin damage while suppressing pigmentation by melanocytes, the controller 50 may control the thermoelectric module 30 to maintain a cooling interval of the first major surface 31 between 5 seconds, which is necessary for suppressing the pigmentation, and less than 300 seconds, at which damage to the skin begins. As another example, the controller 50 may control the thermoelectric module 30 to maintain the cooling interval of the first major surface 31 between 5 seconds, which is necessary for suppressing the pigmentation, and less than 900 seconds, at which microscopic damage to the skin may begin.

Here, the first interval may indicate a minimum interval necessary for suppressing pigmentation by cooling melanocytes. When the skin is cooled for an interval shorter than the first interval, it is not possible to suppress the pigmentation because the melanocytes are not sufficiently cooled. For example, for the skin whitening effect to substantially occur by cooling the skin, the first interval may be at least 5 seconds. However, the first interval may vary according to circumstances. For example, the first interval may be at least 0.5 seconds, which is the minimum interval necessary for the skin whitening effect to occur by the cooling the skin.

Also, the second interval may indicate an interval during which skin damage begins due to the cooling of the skin. When the skin is cooled for an interval longer than the second interval, damage to the skin may occur. For example, the second interval may be 300 seconds at maximum in order to prevent tissue damage due to ischemia and blood clots in small blood vessels or the like that occur as the skin is cooled for a long period. However, the second interval may vary according to circumstances. For example, the second interval may be, at maximum, 900 seconds, which is an interval during which, not only direct damage to the skin, but also microscopic damage to the skin may begin due to cooling the skin for a long period.

The cooling interval of the first major surface 31 that is controlled by the controller 50 is not necessarily limited by the above description and may be determined in various other ways.

Also, the controller 50 may control the thermoelectric module 30 to cool the first major surface for a longer cooling interval as the cooling temperature of the first major surface 31 is higher. For example, the controller 50 may control the thermoelectric module 30 to cool the first major surface 31 for a longer interval when the cooling temperature of the first major surface 31 is 5° C. as compared with when the cooling temperature of the first major surface 31 is −15° C.

Also, the controller 50 according to an embodiment of the present specification may control the thermoelectric module 30 on the basis of a skin temperature measured by the skin temperature sensor. To this end, the controller 50 may store, in the memory 54, result values according to input in the form of functions or a look-up table and use the results values upon calculation. For example, the memory 54 may store a current/voltage table relating to current and/or voltage for each skin temperature and intensity. The controller may determine the size of current/voltage to be applied by referring to the current/voltage table on the basis of a measured skin temperature.

In order to suppress pigmentation by melanocytes while preventing damage to the skin due to cooling, the controller 50 may control the thermoelectric module 30 to change a cooling condition of the first major surface 31 on the basis of a skin temperature measured by the skin temperature sensor.

The controller 50 may control the thermoelectric module 30 to change a cooling temperature of the first major surface 31 on the basis of a skin temperature measured by the skin temperature sensor. For example, the controller 50 may control the thermoelectric module 30 to lower the cooling temperature of the first major surface 31 when the measured skin temperature is higher than the target temperature and raise the cooling temperature of the first major surface 31 when the measured skin temperature is lower than the target temperature. As another example, when the measured skin temperature has reached the target temperature, the controller 50 may control the thermoelectric module 30 to cool the first major surface 31 at a cooling temperature that allows the measured skin temperature to be maintained at the target temperature.

The controller 50 may control the thermoelectric module 30 to change a cooling interval of the first major surface 31 on the basis of a skin temperature measured by the skin temperature sensor. For example, the controller 50 may control the thermoelectric module 30 to extend the cooling interval of the first major surface 31 when the measured skin temperature is higher than the target temperature and shorten the cooling interval of the first major surface 31 when the measured skin temperature is lower than the target temperature.

Also, the controller 50 may control the thermoelectric module 30 so that an interval during which the measured skin temperature is maintained at the target temperature is longer than an interval necessary for suppressing the pigmentation and shorter than an interval during which damage to the skin begins. For example, the controller 50 may control the thermoelectric module 30 so that the measured temperature is maintained at the target temperature (in the range of 4° C. to 27° C.) for 4 seconds to 120 seconds.

However, the first embodiment is not necessarily limited to the above-described method and may be practiced using various other methods, such as that in which the first embodiment is combined with other elements, according to circumstances.

Second Embodiment

Hereinafter, a second embodiment in which the controller 50 controls the temperature of the first major surface 31 of the thermoelectric module 30 will be described. Descriptions overlapping those of the previous embodiment will be omitted. That is, descriptions of the technical ideas relating to the previous embodiment which may apply identically to the second embodiment will be omitted.

Figure 11:
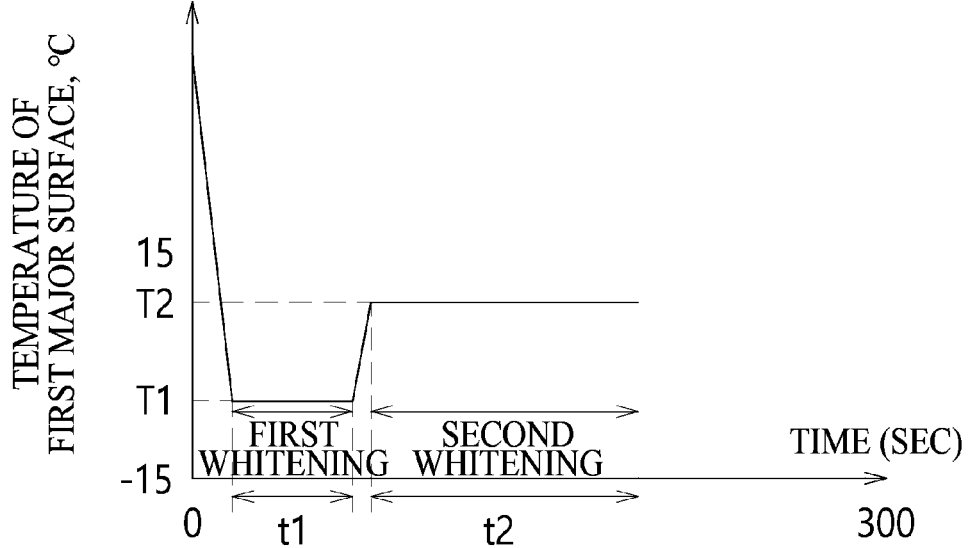
FIG. 11 is a graph showing temperature changes over time of a first major surface of a thermoelectric module according to a second embodiment of the present specification.

FIG. 11 is a graph showing temperature changes over time of a first major surface of a thermoelectric module according to a second embodiment of the present specification.

When the mask 10 cools the skin of a user using only one whitening mode, it is difficult for whitening of the skin to be performed efficiently. This is because the user's skin is prone to damage when the mask 10 cools the user's skin only using a whitening mode having a very low temperature, and the effect of suppressing pigmentation by melanocytes may decrease when the mask 10 cools the user's skin only using a whitening mode having a very high temperature.

Specifically, first, the mask 10 may cool the user's skin at a first whitening temperature, which is lower than a second whitening temperature, to rapidly decrease the temperature of the user's skin and increase the skin whitening effect. However, here, because the skin may be damaged due to low temperature when the mask 10 cools the user's skin at the first whitening temperature for a long period, a first whitening interval during which the first whitening temperature is maintained may be maintained relatively short.

Next, the mask 10 may cool the user's skin at the second whitening temperature which is higher than the first whitening temperature so that the skin whitening effect is increased by reducing damage to the skin due to low temperature and cooling the user's skin for a longer interval. That is, a second whitening interval during which the mask 10 maintains a second whitening mode may be longer than the first whitening interval during which the mask 10 maintains a first whitening mode.

Therefore, for efficient skin whitening, the controller 50 according to an embodiment of the present specification may control the thermoelectric module 30 to sequentially perform the first whitening mode and the second whitening mode which have different cooling conditions. Referring to FIG. 11, it can be seen that the thermoelectric module 30 is controlled by the controller 50 and sequentially performs the first whitening mode, in which the first major surface 31 is cooled for an interval t1 at a cooling temperature T1, and the second whitening mode, in which the first major surface 31 is cooled for an interval t2 longer than the interval t1 for at a cooling temperature T2 higher than the cooling temperature T1.

For efficient skin whitening, the controller 50 may control the thermoelectric module 30 to sequentially perform the first whitening mode and the second whitening mode which have different cooling conditions.

For example, first, the controller 50 may control the thermoelectric module 30 to perform the first whitening mode in which cooling is performed at a first whitening temperature which is lower than a second whitening temperature for a first whitening interval which is shorter than a second whitening interval.

Next, the controller 50 may control the thermoelectric module 30 to perform the second whitening mode in which cooling is performed at the second whitening temperature higher than the first whitening temperature for the second whitening interval longer than the first whitening interval.

Also, the controller 50 may control the thermoelectric module 30 using various other combinations of whitening modes. For example, the controller 50 may control the thermoelectric module 30 using a plurality of whitening modes more than two whitening modes or may sequentially repeat each whitening mode.

However, the second embodiment is not necessarily limited to the above-described method and may be practiced using various other methods, such as that in which the second embodiment is combined with other elements, according to circumstances.

Third Embodiment

Hereinafter, a third embodiment in which the controller 50 controls the temperature of the first major surface 31 of the thermoelectric module 30 will be described. Descriptions overlapping those of the previous embodiments will be omitted. That is, descriptions of the technical ideas relating to the previous embodiments which may apply identically to the third embodiment will be omitted.

Figure 12:
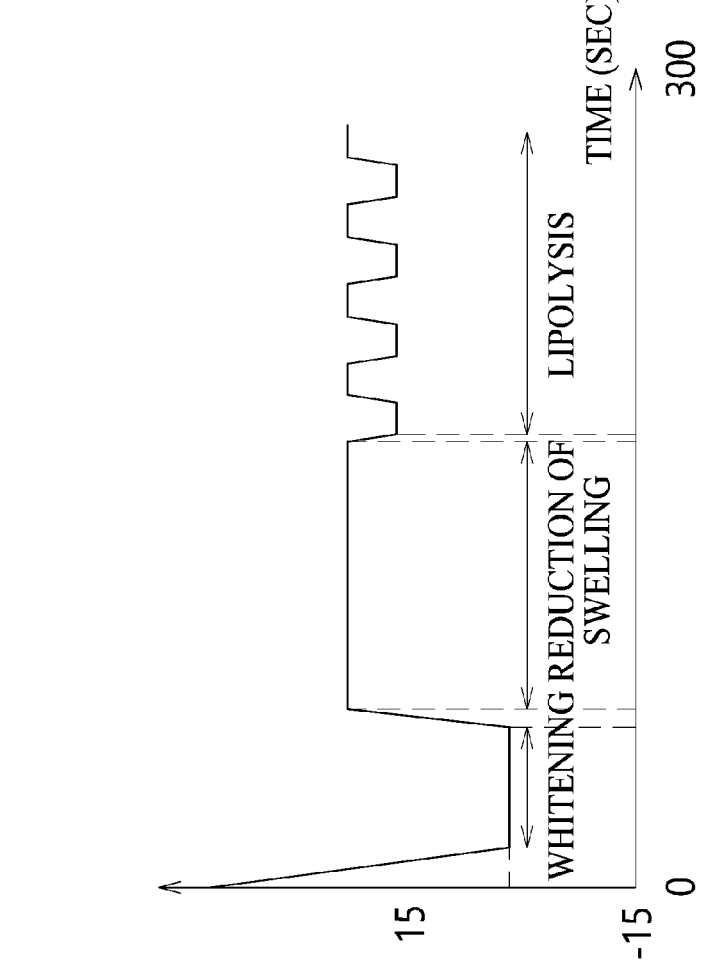
FIG. 12 is a graph showing temperature changes over time of a first major surface of a thermoelectric module according to a third embodiment of the present specification.

FIG. 12 is a graph showing temperature changes over time of a first major surface of a thermoelectric module according to a third embodiment of the present specification.

Generally, when the user's skin is cooled, additional effects such as reduction of swelling and lipolysis may occur in addition to the skin whitening effect. However, an optimum temperature at which the skin whitening effect occurs is slightly different from an optimum temperature at which additional effects such as reduction of welling and lipolysis occur.

Generally, a cooling temperature for causing the swelling reduction effect and lipolytic effect is higher than a cooling temperature for causing the whitening effect, and a cooling interval for causing the swelling reduction effect and lipolytic effect is longer than a cooling interval for causing the whitening effect. Here, when the user's skin is cooled by repeatedly raising and dropping the temperature, the lipolytic effect may be increased.

Therefore, the controller 50 according to an embodiment of the present specification may control the thermoelectric module 30 to cool the first major surface also under conditions that cause other additional effects. For example, the controller 50 may control the thermoelectric module 30 to cool the first major surface 31 under conditions that cause effects such as reduction of swelling and lipolysis.

Referring to FIG. 12, it can be seen that the thermoelectric module 30 is controlled by the controller and, after performing the whitening modes, sequentially performs a swelling reduction mode in which the first major surface 31 is cooled under a cooling condition that causes the swelling reduction effect and a lipolysis mode in which the first major surface 31 is cooled under a cooling condition that causes the lipolytic effect.

The controller 50 may control the thermoelectric module 30 to cool the first major surface 31 under a cooling condition for reducing swelling on the user's skin.

The controller 50 may control the thermoelectric module 30 to perform a swelling reduction mode in which the first major surface 31 is cooled within a temperature range that is higher than a whitening temperature range of the whitening modes. For example, the controller 50 may control the thermoelectric module 30 to cool the first major surface 31 within a temperature range of ° C. to 20° C. that is higher than the whitening temperature range of the whitening modes.

The controller 50 may control the thermoelectric module 30 to perform a swelling reduction mode in which the first major surface 31 is cooled for a longer interval than the whitening intervals of the whitening modes. For example, the controller 50 may control the thermoelectric module 30 to cool the first major surface 31 for an interval in a range of 4 seconds to 20 minutes that is longer than the whitening intervals of the whitening modes.

The controller 50 may control the thermoelectric module 30 to cool the first major surface 31 under a cooling condition for lipolysis of the user's skin.

The controller 50 may control the thermoelectric module 30 to perform a lipolysis mode in which the first major surface 31 is cooled within a temperature range higher than the whitening temperature range of the whitening modes. For example, the controller 50 may control the thermoelectric module 30 to cool the first major surface 31 within a temperature range of 10° C. to 20° C. that is higher than the whitening temperature range of the whitening modes. Also, the controller 50 may control the thermoelectric module 30 to cool the first major surface by repeatedly raising and dropping the temperature within the temperature range of 10° C. to 20° C.

Also, the controller 50 may control the thermoelectric module 30 to perform a lipolysis mode in which the first major surface 31 is cooled for a longer interval than the whitening intervals of the whitening modes. For example, the controller 50 may control the thermoelectric module 30 to cool the first major surface 31 for an interval in a range of 4 seconds to 2 hours that is longer than the whitening intervals of the whitening modes.

Also, the controller 50 may control the thermoelectric module 30 to perform at least one operation mode of the whitening modes, the swelling reduction mode, and the lipolysis mode. For example, the controller 50 may control the thermoelectric module 30 to sequentially perform the swelling reduction mode and the lipolysis mode after performing the whitening modes.

Also, the controller 50 may control the thermoelectric module 30 to perform at least one of the swelling reduction mode and the lipolysis mode simultaneously with the whitening mode during at least a portion of the whitening interval during which the whitening mode is performed. That is, the controller 50 may control the thermoelectric module 30 so that the whitening temperature range overlaps with the temperature range of the swelling reduction mode and/or the lipolysis mode during at least a portion of the whitening interval during which the whitening mode is performed.

Also, the controller 50 may control the thermoelectric module 30 to perform the operation modes in various other combinations. For example, the controller 50 may control the thermoelectric module 30 to sequentially repeat the whitening modes, the swelling reduction mode, and the lipolysis mode.

Also, the controller 50 may control the thermoelectric module 30 to perform various operation modes for improving the skin, such as a skin regeneration mode and a skin elasticity mode, other than the whitening modes, the swelling reduction mode, and the lipolysis mode.

However, the third embodiment is not necessarily limited to the above-described method and may be practiced using various other methods, such as that in which the third embodiment is combined with other elements, according to circumstances.

Fourth Embodiment

Hereinafter, a fourth embodiment in which the controller 50 controls the temperature of the first major surface 31 of the thermoelectric module 30 will be described. Descriptions overlapping those of the previous embodiments will be omitted. That is, descriptions of the technical ideas relating to the previous embodiments which may apply identically to the fourth embodiment will be omitted.

Figure 13:
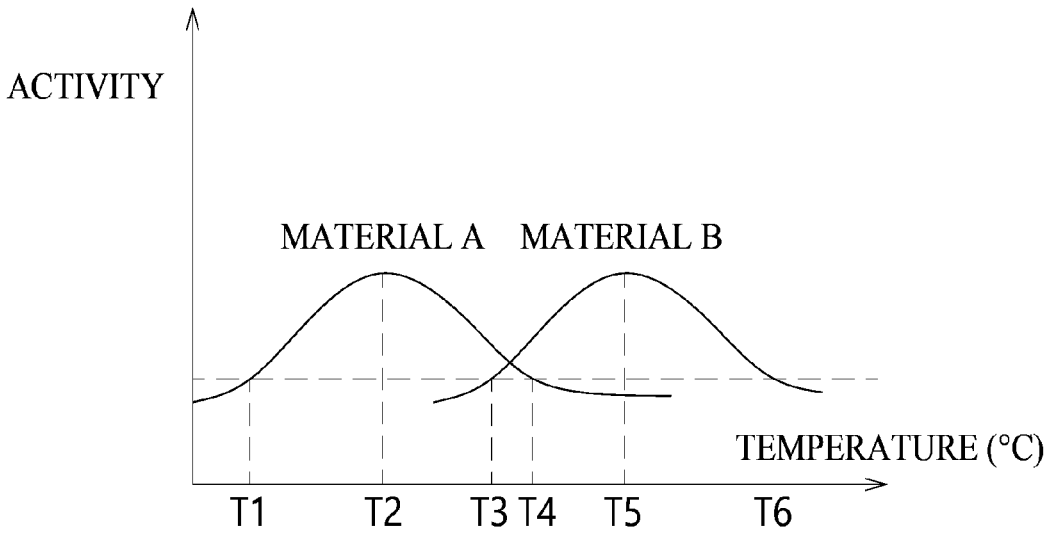
FIG. 13 is an exemplary graph showing activity of a functional material according to temperature.

FIG. 13 is an exemplary graph showing activity of a functional material according to temperature.

Referring to FIG. 13, the activity of a functional material may change according to temperature. A temperature range in which a functional material is active and a temperature at which the activity is maximum may be different for each functional material. That is, an activation temperature range, in which the activity is at a predetermined level or higher (e.g., nine-tenth of the maximum activity or higher), and a maximum activation temperature, at which the activity is maximum, may be different for each functional material. For example, from the graph of FIG. 13, it can be seen that functional material A has an activation temperature range ranging from T1 to T4 and maximum activity at T2, and functional material B has an activation temperature range ranging from T3 to T6 and maximum activity at T5.

A functional material 21 may be a material whose function is further activated at low temperature. For example, the functional material 21 may be a whitening functional material whose whitening effect is further enhanced (whitening function is further activated) at low temperature. As an example, which is not limiting, the functional material 21 may include resorcinol and similar derivatives (hexyl resorcinol, butyl resorcinol, phenylethyl resorcinol, resorcinol acetate, and other similar derivatives) and may be formed of one of the materials or a mixture of two or more thereof.

As another example, the functional material 21 may be a whitening functional material that further reduces irritation (e.g., irritation due to cooling) and whose effective concentration increases at low temperature. As an example, which is not limiting, the functional material 21 may include and be formed of one of, or a mixture of two or more of, resorcinol and similar derivatives (hexyl resorcinol, butyl resorcinol, phenylethyl resorcinol, resorcinol acetate, and other similar derivatives), niacinamide and a composition containing the same, magnesium ascorbylphosphate and a composition containing the same, ascorbyl glucoside and a composition containing the same, ascorbyl tetraisopalmitate/dipalmitate and a composition containing the same, arbutin and a composition containing the same, α-bisabolol and a composition containing the same, ethyl ascorbyl ether and a composition containing the same, polyphenol derivatives and a composition containing the same, L-glutathione and a composition containing the same, tranexamic acid and a composition containing the same, 4-methoxysalicylic acid potassium salt (KCl) derivatives and a composition containing the same, glycyrrhizine and a composition containing the same, azelaic acid, azelaic acid derivatives (e.g., azeloyl diglycine) and a composition containing the same, nicotinamide, nicotinamide derivatives and a composition containing the same, resveratrol, resveratrol derivatives and a composition containing the same, glycyrrhiza flavonoids, ellagic acid and a composition containing the same, papain and a composition containing the same, mandelic acid, mandelic acid derivatives and a composition containing the same, heptapeptide-1 and a composition containing the same, kojic acid, kojic acid derivatives and a composition containing the same, and plant extracts and a composition containing the same that contain all or some of the following ingredients: jasmine extract, mulberry extract, paper mulberry extract, licorice extract, ginseng extract, salvia miltiorrhiza extract, corn extract, chrysanthemum extract, bark root extract, thyme extract, white fresh root extract, polygon extract, magnolia tree extract, angelica root extract, *Phyllanthus emblica* (fruit) extract, and citrus extract.

However, the graph of FIG. 13 is merely a schematic graph illustrated for description, and the fourth embodiment is not limited thereto. The activity of the actual functional material according to temperature may be different from the graph.

Figure 14:
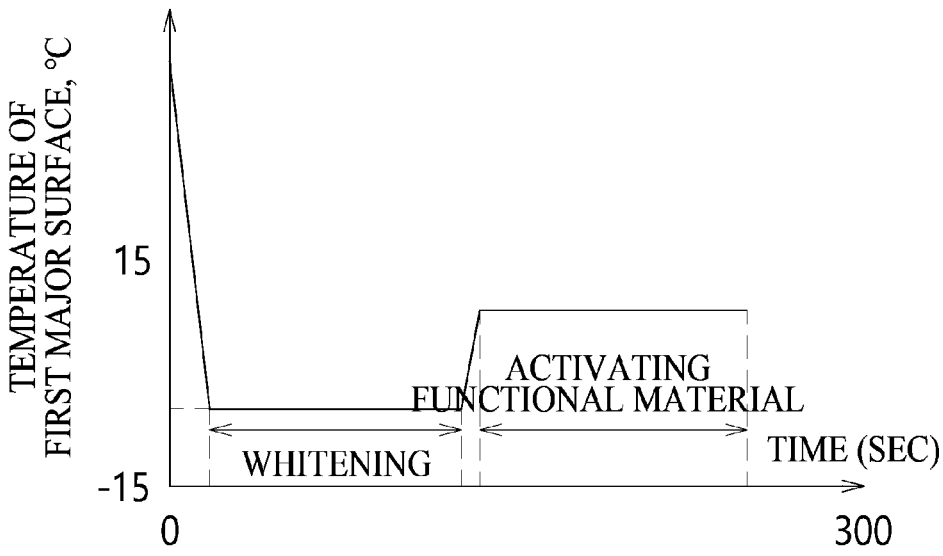
FIG. 14 is a graph showing temperature changes over time of a first major surface of a thermoelectric module according to a fourth embodiment of the present specification.

FIG. 14 is a graph showing temperature changes over time of a first major surface of a thermoelectric module according to the fourth embodiment of the present specification.

Because the activity of the functional material 21 accommodated in the contact layer 20 changes according to temperature, when the temperature of the first major surface 31 is within the activation temperature range of the functional material 21 accommodated in the contact layer 20, and thus the user's skin is cooled within the activation temperature range of the functional material 21, the skin improvement effect by the functional material 21 may increase.

Therefore, the controller 50 according to an embodiment of the present specification may control the thermoelectric module 30 to perform a functional material activation mode in which the first major surface 31 is cooled within the activation temperature range of the functional material 21 accommodated in the contact layer 20.

The controller 50 may control the thermoelectric module 30 to cool the first major surface 31 within the activation temperature range of the functional material 21 accommodated in the contact layer 20. For example, when the activation temperature range of the functional material 21 accommodated in the contact layer 20 ranges from 0° C. to 10° C., the controller 50 may control the thermoelectric module 30 to cool the first major surface 31 within the range of 0° C. to 10° C.

Also, the controller 50 may control the thermoelectric module 30 to cool the first major surface at a temperature at which the activity is maximum within the activation temperature range of the functional material 21 accommodated in the contact layer 20. For example, when the temperature at which the activity is maximum within the activation temperature range of the functional material 21 accommodated in the contact layer 20 is 5° C., the controller 50 may control the thermoelectric module 30 to cool the first major surface 31 at 5° C.

Also, the controller 50 may control the thermoelectric module 30 to cool the first major surface 31 in the functional material activation at a temperature higher than the whitening temperatures of the whitening modes. This is to prevent damage to the user's skin while maximizing the effect of whitening the user's skin.

Also, the controller 50 may control the thermoelectric module 30 to cool the first major surface 31 in the functional material activation mode for a cooling interval longer than the whitening intervals of the whitening modes. This is to prevent damage to the user's skin while maximizing the effect of whitening the user's skin.

Also, the controller 50 may control the thermoelectric module 30 to perform at least one operation mode of the whitening modes and the functional material activation mode. For example, the controller 50 may control the thermoelectric module 30 to sequentially perform the whitening modes and the functional material activation mode in that order.

Also, the controller 50 may control the thermoelectric module 30 to perform the functional material activation mode simultaneously with the whitening mode during at least a portion of the whitening interval during which the whitening mode is performed. That is, the controller 50 may control the thermoelectric module 30 so that the whitening temperature range overlaps with the activation temperature range of the functional material 21 during at least a portion of the whitening interval during which the whitening mode is performed.

Also, the controller 50 may control the thermoelectric module 30 to perform the operation modes in various other combinations. For example, the controller 50 may control the thermoelectric module 30 to sequentially repeat the whitening modes and the functional material activation mode.

However, the fourth embodiment is not necessarily limited to the above-described method and may be practiced using various other methods, such as that in which the fourth embodiment is combined with other elements, according to circumstances.

Fifth Embodiment

Hereinafter, a fifth embodiment in which the controller 50 controls the temperature of the first major surface 31 of the thermoelectric module 30 will be described. Descriptions overlapping those of the previous embodiments will be omitted. That is, descriptions of the technical ideas relating to the previous embodiments which may apply identically to the fifth embodiment will be omitted.

Figure 15:
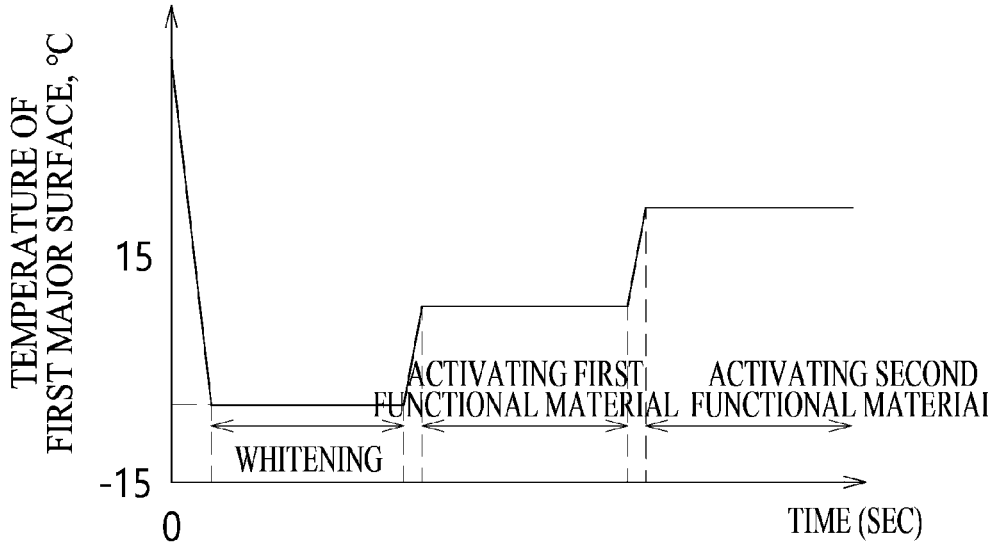
FIG. 15 is a graph showing temperature changes over time of a first major surface of a thermoelectric module according to a fifth embodiment of the present specification.

FIG. 15 is a graph showing temperature changes over time of a first major surface of a thermoelectric module according to a fifth embodiment of the present specification.

In order to obtain a comprehensive skin improvement effect, a plurality of functional materials 21 may be accommodated in the contact layer 20. In the case in which the plurality of functional materials 21 are accommodated in the contact layer 20, when a functional material activation mode is performed within an activation temperature range for activating any one functional material 21, another functional material may not be activated.

Therefore, when a plurality of functional materials are accommodated in the contact layer 20, the controller 50 according to an embodiment of the present specification may control the thermoelectric module 30 to perform a first functional material activation mode, in which the first major surface 31 of the thermoelectric module 30 is cooled within a first activation temperature range of a first functional material 21-1 accommodated in the contact layer 20, and a second functional material activation mode, in which the first major surface 31 is cooled within a second activation temperature range of a second functional material 21-2 accommodated in the contact layer 20.

Referring to FIG. 15, the controller 50 may control the thermoelectric module 30 to perform the first functional material activation mode, in which the first major surface 31 of the thermoelectric module 30 is cooled within the first activation temperature range of the first functional material 21-1 accommodated in the contact layer 20, and the second functional material activation mode, in which the first major surface 31 is cooled within the second activation temperature range of the second functional material 21-2 accommodated in the contact layer 20.

Also, the controller 50 may control the thermoelectric module 30 to perform at least one operation mode of the whitening modes, the first functional material activation mode, and the second functional material activation mode. For example, the controller 50 may control the thermoelectric module 30 to sequentially perform the first functional material activation mode and the second functional material activation mode after performing the whitening modes.

Also, the controller 50 may control the thermoelectric module 30 to perform at least one of the first functional material activation mode and the second functional material activation mode simultaneously with the whitening mode during at least a portion of the whitening interval during which the whitening mode is performed. That is, the controller 50 may control the thermoelectric module 30 so that at least one of the first activation temperature range of the first functional material 21-1 and the second activation temperature range of the second functional material 21-2 overlaps the whitening temperature range during at least a portion of the whitening interval during which the whitening mode is performed.

Also, the controller 50 may control the thermoelectric module 30 to perform the operation modes in various other combinations. For example, the controller 50 may control the thermoelectric module 30 to sequentially repeat the whitening modes, the first functional material activation mode, and the second functional material activation mode.

However, the fifth embodiment is not necessarily limited to the above-described method and may be practiced using various other methods, such as that in which the fifth embodiment is combined with other elements, according to circumstances.

Sixth Embodiment

Hereinafter, a sixth embodiment in which the controller 50 controls the temperature of the first major surface 31 of the thermoelectric module 30 will be described. Descriptions overlapping those of the previous embodiments will be omitted. That is, descriptions of the technical ideas relating to the previous embodiments which may apply identically to the sixth embodiment will be omitted.

Figure 16:
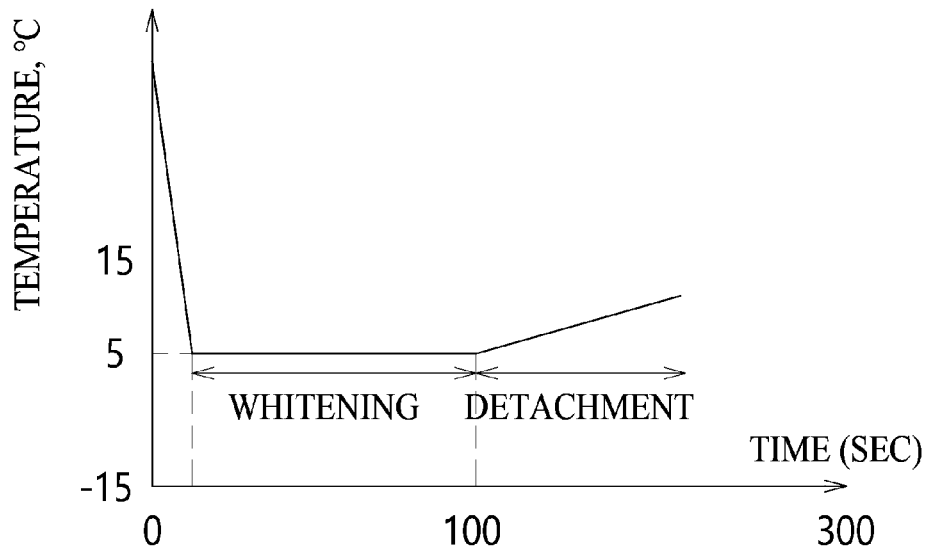
FIG. 16 is a graph showing temperature changes over time of a first major surface of a thermoelectric module according to a sixth embodiment of the present specification.

FIG. 16 is a graph showing temperature changes over time of a first major surface of a thermoelectric module according to a sixth embodiment of the present specification.

In a case in which, after the cooling of the first major surface 31 is completed by power applied to the thermoelectric module 30 by the controller 50, the power to the thermoelectric module 30 is cut off by the controller 50, the temperature of the thermoelectric module 30 rises due to heat generated from the second major surface 32 and rapidly approaches the high temperature of the second major surface 32. In this case, when the thermoelectric module 30 with an increased temperature suddenly applies heat to the user's skin which has been cooled to low temperature, the user may suddenly feel relatively uncomfortable due to hotness, and damage to the skin may occur due to the high temperature.

Therefore, the controller 50 according to an embodiment of the present specification may control the thermoelectric module 30 so that, after the cooling of the first major surface 31 is completed (e.g., the whitening mode, the functional material activation mode, or the like is completed), the temperature of the first major surface 31 does not increase rapidly before the user removes the mask. Referring to FIG. 16, it can be seen that, after the whitening mode in which the first major surface 31 is cooled at a cooling temperature of ° C. for 100 seconds is completed, the thermoelectric module 30 is controlled by the controller 50 and performs a detachment mode in which the temperature of the first major surface 31 gradually increases. Hereinafter, the detachment mode refers to a mode in which, after the cooling of the first major surface 31 is completed (an operation mode is ended), the controller 50 controls the temperature of the first major surface 31.

In order to prevent the temperature of the first major surface 31 from rapidly increasing after the cooling of the first major surface 31 is completed, the controller 50 may control the thermoelectric module 30 to perform the detachment mode in which the temperature of the first major surface 31 gradually increases. For example, the controller 50 may control the thermoelectric module 30 so that, after the cooling of the first major surface 31 is completed, the temperature of the first major surface 31 increases by 0.3° C. per second.

Also, the controller 50 may control the thermoelectric module 30 to perform the detachment mode in which, after the cooling of the first major surface 31 is completed, the temperature of the first major surface is maintained at a predetermined temperature. For example, the controller 50 may control the thermoelectric module 30 so that the temperature of the first major surface 31 gradually increases and reaches a temperature in a range of 5° C. to 30° C. Alternatively, the controller 50 may also control the thermoelectric module 30 so that, after the cooling of the first major surface 31 is completed, the temperature of the first major surface 31 is maintained as it is.

Also, the controller 50 may control the thermoelectric module 30 to maintain the detachment mode for a predetermined amount of time so that a sufficient amount of time is provided for the user to remove the mask 10 while the detachment mode is performed. For example, the controller 50 may control the thermoelectric module 30 to perform the detachment mode for an interval in a range of 10 seconds to 5 minutes.

Also, when the controller 50 obtains a signal indicating that the user has removed the mask 10, the controller 50 may control the thermoelectric module 30 to end the detachment mode. For example, the controller 50 may control the thermoelectric module 30 to end the detachment mode when a power off signal is received from the user or a signal indicating that the user's skin is not detected is obtained via a touch sensing module.

Also, the controller 50 may control an output module to output a notification when the detachment mode starts or ends. For example, the controller 50 may control the output module to output vibration or a voice message that notifies of detachment of the mask upon the start of the detachment mode. Alternatively, the controller 50 may control a vibration generating module to output vibration when the detachment mode starts or ends.

However, the sixth embodiment is not necessarily limited to the above-described method and may be practiced using various other methods, such as that in which the sixth embodiment is combined with other elements, according to circumstances.

Additional Embodiments

Hereinafter, various additional embodiments in which the controller 50 controls the mask 10 will be described. Descriptions overlapping those of the previous embodiments will be omitted. That is, descriptions of the technical ideas relating to the previous embodiments which may apply identically to the additional embodiments will be omitted.

Because cooling conditions for achieving the optimum whitening effect are different for each individual, the mask 10 may cool the user's skin under different cooling conditions for each individual in order to achieve the optimum whitening effect.

Therefore, the controller 50 according to an embodiment of the present specification may control the thermoelectric module 30 to perform an operation mode set by the user other than a preset operation mode. Alternatively, the controller 50 may control the thermoelectric module 30 to perform an operation mode that results from arbitrarily modifying a preset operation mode.

The controller 50 may control the thermoelectric module 30 to cool the first major surface 31 under a cooling condition received from the input module 52. For example, the controller 50 may control the thermoelectric module 30 to cool the first major surface 31 according to data relating to cooling conditions of the first major surface 31 (the cooling interval of the first major surface 31, the cooling temperature of the first major surface 31, cooling order, cooling area, and the like) which are received from the input module 52.

Also, the controller 50 may control the thermoelectric module 30 to cool the first major surface 31 according to a cooling condition obtained from an external device via the communication module 51. For example, the controller 50 may control the thermoelectric module 30 to cool the first major surface 31 according to data relating to cooling conditions of the first major surface 31 (the cooling interval of the first major surface 31, the cooling temperature of the first major surface 31, cooling order, cooling area, and the like) which are received from an external device via the communication module 51.

Exemplary embodiments have been described above with reference to the accompanying drawings, but those of ordinary skill in the art may make various modifications and changes from the description above. For example, appropriate results can be achieved even when the described techniques are performed in a different order from the described methods or when the conditions are different.

Figure 17:
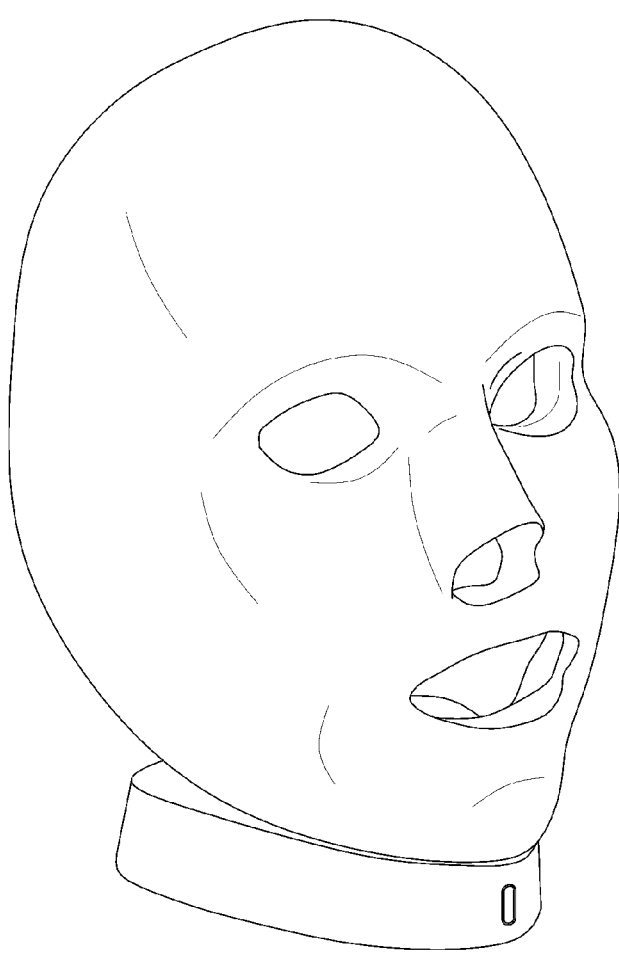
FIG. 17 illustrates a cradle on which a mask is mounted according to an embodiment of the present specification.

FIG. 17 illustrates a cradle on which a mask is mounted according to an embodiment of the present specification.

Referring to FIG. 17, a cradle 60 for keeping the mask 10 while it is not in use may be provided in the shape corresponding to the mask 10. Of course, the cradle 60 is not limited to the present embodiment and may be provided in various other shapes on which the mask 10 may be mounted. For example, as illustrated in FIG. 17, the cradle 60 may be provided in the form in which, when the mask 10 is mounted, the contact layer 20 comes in contact with one surface of the cradle 60. However, the cradle 60 may also be provided in the form in which, when the mask 10 is mounted, the heat dissipation layer 40 comes in contact with one surface of the cradle 60.

Also, the cradle 60 may include a heat dissipation means (not illustrated) such as a separate thermoelectric module, fan, fluid circulator or the like for aiding in heat dissipation by the heat dissipation layer 40 when the mask 10 is mounted on the cradle 60.

According to an embodiment, when the mask 10 is mounted on the cradle 60 which is provided in the form in which, when the mask 10 is mounted, the contact layer 20 comes in contact with one surface of the cradle 60, a direction of current applied to the thermoelectric module 30 of the mask 10 is reversed, and the mask 10 may cool the heat dissipation layer 40 through the second major surface 32, and the cradle 60 may dissipate, via a separate heat dissipation means, heat generated from the first major surface 31 of the thermoelectric module 30. For example, when the mask 10 is mounted on the cradle 60, the mask 10 may, via the second major surface 32, cool the heat dissipation layer 40 below a melting point of a phase-change material included in the heat dissipation layer 40, and the cradle 60 may, via a separate fan or thermoelectric module, dissipate heat generated from the first major surface 31.

According to another embodiment, when the mask 10 is mounted on the cradle 60 which is provided in the form in which, when the mask 10 is mounted, the heat dissipation layer 40 comes in contact with one surface of the cradle 60, the cradle 60 may cool the heat dissipation layer 40 via a separate heat dissipation means. For example, when the mask 10 is mounted on the cradle 60, the cradle 60 may, via a thermoelectric module disposed at one surface of the cradle 60, cool the heat dissipation layer 40 below a melting point of a phase-change material included in the heat dissipation layer 40.

Figure 18:
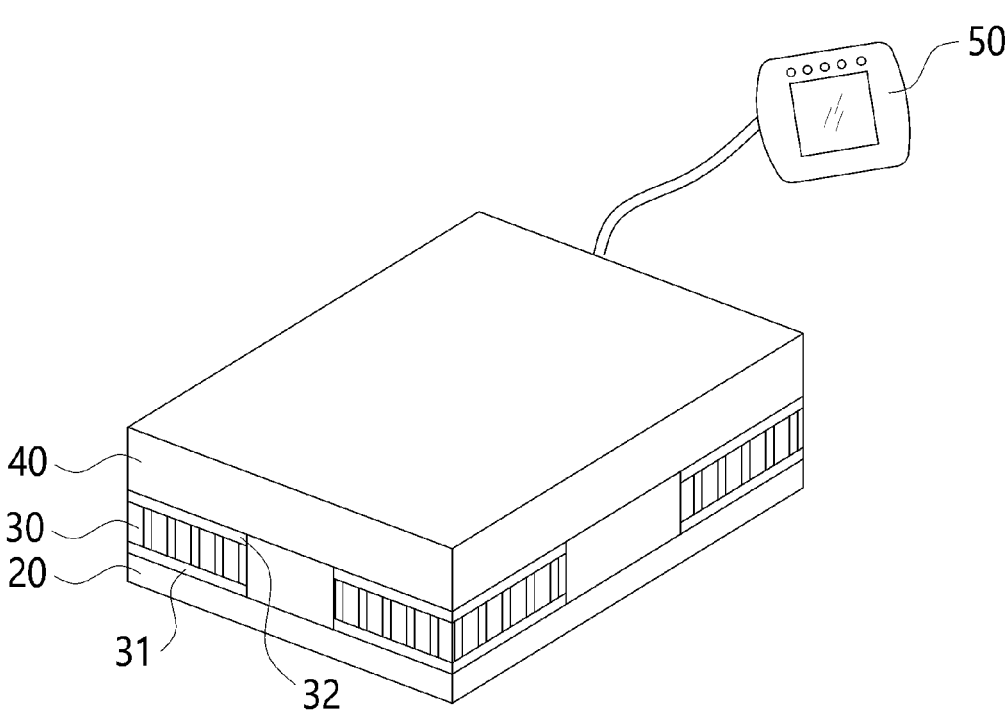
FIG. 18 is a perspective view of a skin whitening device according to an embodiment of the present specification.

FIG. 18 is a perspective view of a device for whitening skin according to an embodiment of the present specification.

Referring to FIG. 18, a device for whitening skin 11 may have a basic form for being adhered to various body parts of a user and be provided in the form of a pad. FIG. 18 only illustrates the device for whitening skin 11 provided in the form of a pad, but the device for whitening skin 11 may be provided in various forms. For example, the device for whitening skin 11 may be provided in forms corresponding to various body parts in order to be adhered to various body parts of the user and evenly cool the user's skin. That is, the device for whitening skin 11 may be provided to be flexible and bendable. Also, the device for whitening skin 11 may include a contact layer 20, at least one thermoelectric module 30, a heat dissipation layer 40, and a controller 50.

Because the contact layer 20, the thermoelectric module 30, the heat dissipation layer 40, and the controller 50 have been described above, detailed descriptions thereof will be omitted.

Meanwhile, although not illustrated in the drawings, the device for whitening skin 11 according to an embodiment of the present specification may further include a strap, a band, or the like that provides tension so that, upon use of the device for whitening skin 11 by the user, a surface of the device for whitening skin 11 that comes in contact with the user's skin is sufficiently adhered thereto.

However, the device for whitening skin 11 is not limited by the above-described configuration. The device for whitening skin 11 may include elements more or less than those described above, and each element is not limited by the above description.

Figure 19:
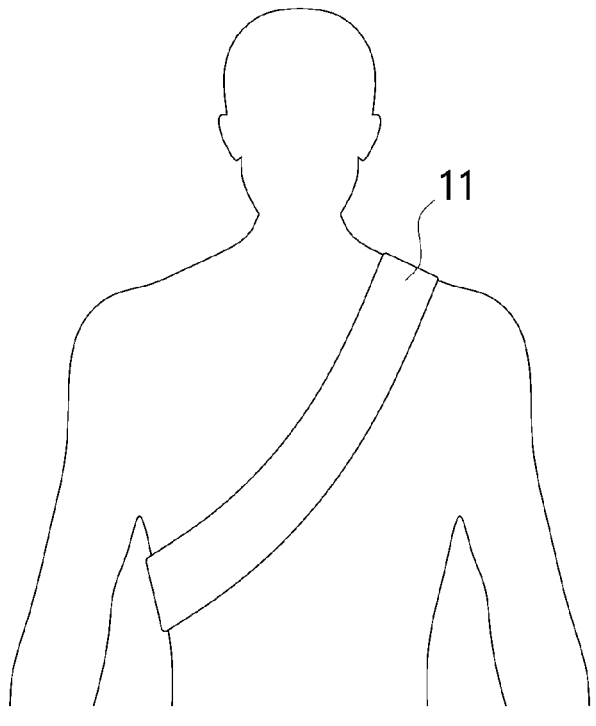
FIG. 19 is a view illustrating a state in which a skin whitening device is used for an upper body part of a user according to an embodiment of the present specification.

FIG. 19 is a view illustrating a state in which a device for whitening skin is used for an upper body part of a user according to an embodiment of the present specification.

Referring to FIG. 19, the device for whitening skin 11 may be provided in the form of a pad and used for the upper body part of the user.

Figure 20:
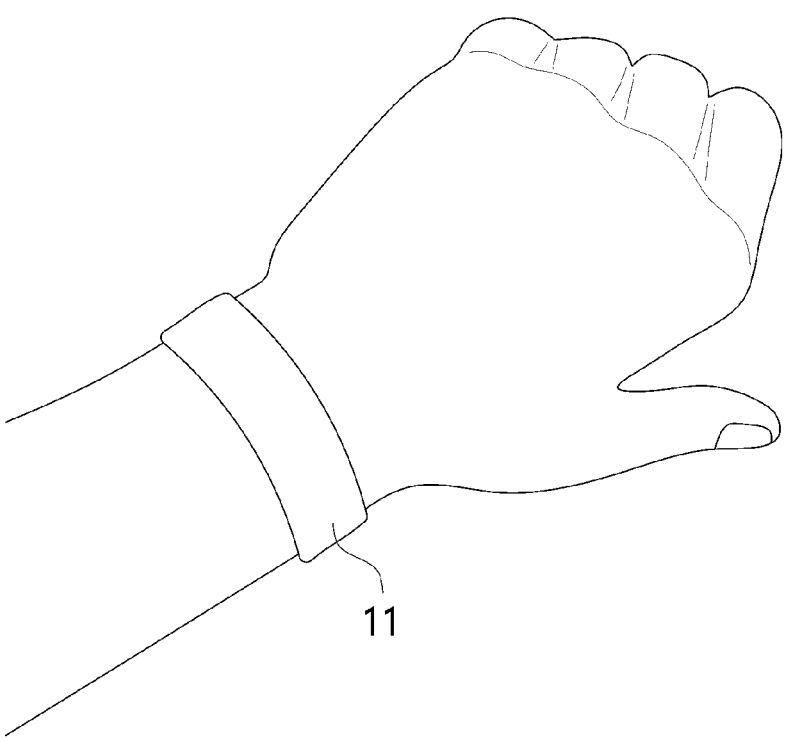
FIG. 20 is a view illustrating a state in which a skin whitening device is used for a wrist area of a user according to an embodiment of the present specification.

FIG. 20 is a view illustrating a state in which a device for whitening skin is used for a wrist area of a user according to an embodiment of the present specification.

Referring to FIG. 20, the device for whitening skin 11 may be provided in the form of a band corresponding to a wrist area and used for the wrist area of the user.

Figure 21:
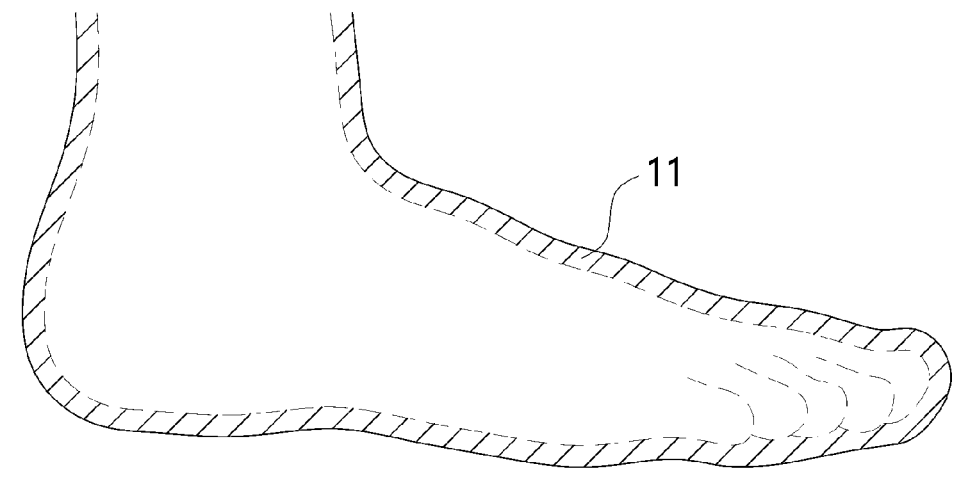
FIG. 21 is a view illustrating a state in which a skin whitening device is used for a foot area of a user according to an embodiment of the present specification.

FIG. 21 is a view illustrating a state in which a device for whitening skin is used for a foot area of a user according to an embodiment of the present specification.

Referring to FIG. 21, the device for whitening skin 11 may be provided in the shape corresponding to a foot area and used for the foot area of the user.

Figure 22:
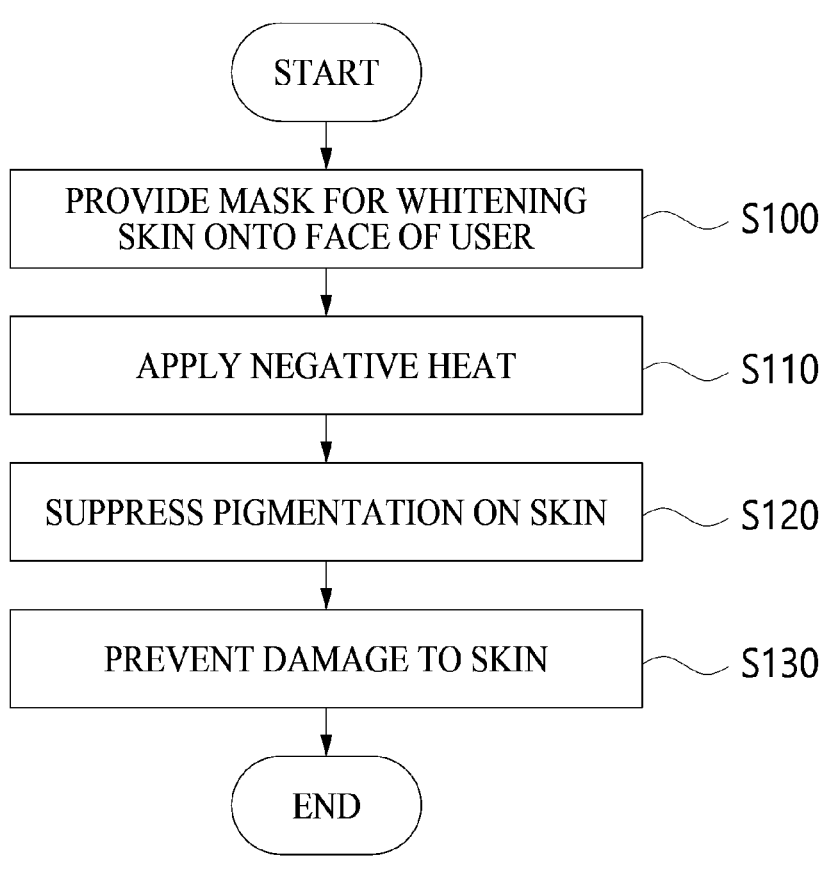
FIG. 22 is a flowchart of a skin whitening method using a skin whitening mask according to an embodiment of the present specification.

FIG. 22 is a flowchart of a method for whitening skin using a mask for whitening skin according to an embodiment of the present specification.

Referring to FIG. 22, a method for whitening skin using the mask for whitening skin 10 may include positioning the mask for whitening skin 10 onto the face of a user (S100), applying negative heat (S110), suppressing pigmentation of the skin (S120), and preventing damage to the facial skin (S130).

The mask for whitening skin 10 may be positioned on the face of the user so that a lower portion of a contact layer 20 adheres to the face (S100).

For example, the mask for whitening skin 10 may be positioned on the face of the user so that the lower portion of the contact layer 20 adheres to the face, wherein the mask for whitening skin 10 includes the contact layer 20 which has the lower portion coming in contact with the face of the user and is provided with a flexible material, at least one thermoelectric module 30 which has two major surfaces 31 and 32 including a first major surface 31 disposed in contact with an upper portion of the contact layer 20 and a second major surface 32 positioned opposite to the first major surface and, as power is applied, cools the first major surface 31, a heat dissipation layer 40 disposed at an upper portion of the thermoelectric module 30 so as to come in contact with the second major surface 32 of the thermoelectric module 30 and configured to receive, via the second major surface 32, heat generated upon cooling of the first major surface 31 and dissipate the received heat, and a controller 50 configured to control the thermoelectric module 30.

Also, the mask for whitening skin 10 may further include a strap, a band, or the like that provides tension so that a surface of the mask for whitening skin that comes in contact with the user's skin is sufficiently adhered thereto.

Also, the mask for whitening skin 10 may apply negative heat to the user's skin via the thermoelectric module 30 (S110).

The mask for whitening skin 10 may perform skin whitening via the thermoelectric module 30 and apply negative heat to the user's skin to prevent damage to the skin. For example, the mask for whitening skin 10 may, as power is applied to the thermoelectric module 30, cool the first major surface 31 and apply negative heat to the user's skin via the contact layer 20.

Also, the mask for whitening skin 10 may suppress pigmentation by melanocytes on the skin (S120).

The mask for whitening skin 10 may, via the thermoelectric module 30, apply negative heat to the user's skin at a temperature at which pigmentation by melanocytes may be suppressed.

For example, the mask for whitening skin 10 may cool the first major surface 31 at a cooling temperature such that the skin of the user reaches a target temperature at which pigmentation by melanocytes is suppressed, wherein the target temperature is in a range of 4° C. to 27° C. and the cooling temperature is in a range of −15° C. to 15° C. and lower than the target temperature.

Also, the mask for whitening skin 10 may prevent damage to the skin (S130).

The mask for whitening skin 10 may, via the thermoelectric module 30, apply negative heat to the user's skin for an interval during which damage to the skin does not occur.

For example, the mask for whitening skin 10 may prevent damage to the skin by maintaining a cooling interval, during which the cooling of the first major surface 31 occurs, in a range of 5 seconds, which is necessary for suppressing the pigmentation, to less than 300 seconds, at which damage to the skin begins.

Because the descriptions given above may apply identically to the method for whitening skin illustrated in FIG. 22, more detailed descriptions will be omitted.

Figure 23:
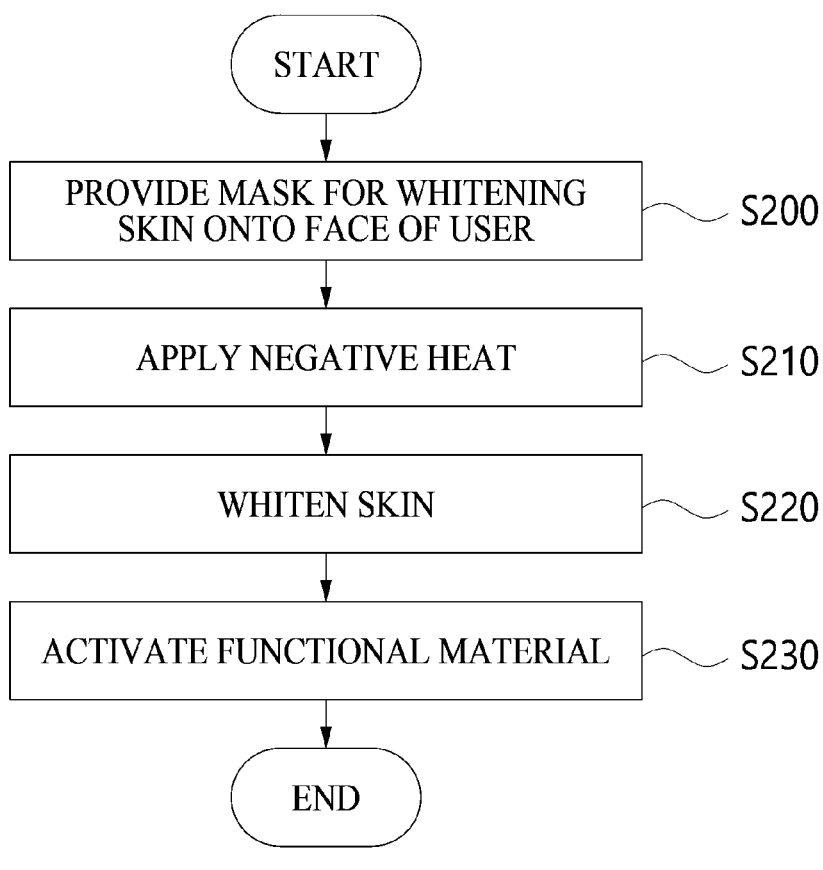
FIG. 23 is a flowchart of a skin whitening method using a skin whitening mask according to an embodiment of the present specification.

FIG. 23 is a flowchart of a method for whitening skin using a mask for whitening skin according to an embodiment of the present specification.

Referring to FIG. 23, a method for whitening skin using a mask for whitening skin 10 may include positioning the mask for whitening skin 10 on the face of a user (S200), applying negative heat (S210), whitening the skin (S220), and activating a functional material (S230).

The mask for whitening skin 10 may be positioned on the face of the user so that a lower portion of a contact layer 20 adheres to the face (S200).

For example, the mask for whitening skin 10 may be positioned on the face of the user so that the lower portion of the contact layer 20 adheres to the face, wherein the mask for whitening skin 10 includes the contact layer 20 which has the lower portion coming in contact with the face of the user and is provided with a flexible material, a functional material 21 which is accommodated in the contact layer 20, is configured to improve the skin of the face of the user, and has an activation temperature range, at least one thermoelectric module 30 which has two major surfaces 31 and 32 including a first major surface 31 disposed in contact with an upper portion of the contact layer 20 and a second major surface 32 positioned opposite to the first major surface 31 and, as power is applied, cools the first major surface 31, a heat dissipation layer 40 disposed at an upper portion of the thermoelectric module 30 so as to come in contact with the second major surface of the thermoelectric module 30 and configured to receive, via the second major surface 32, heat generated upon cooling of the first major surface 31 and dissipate the received heat, and a controller 50 configured to control the thermoelectric module 30.

Also, the mask for whitening skin 10 may apply negative heat to the user's skin via the thermoelectric module 30 (S210).

The mask for whitening skin 10 may perform skin whitening via the thermoelectric module 30 and apply negative heat to the user's skin to activate the functional material 21. For example, the mask for whitening skin 10 may, as power is applied to the thermoelectric module 30, cool the first major surface 31 and apply negative heat to the user's skin via the contact layer 20.

Also, the mask for whitening skin 10 may perform skin whitening by applying negative heat to the user's skin (S220).

The mask for whitening skin 10 may perform skin whitening by, via the controller 50, cooling the first major surface 31 within a whitening temperature range in which pigmentation by melanocytes is suppressed.

For example, the mask for whitening skin 10 may cool the first major surface 31 at a cooling temperature such that the skin of the user reaches a target temperature at which pigmentation by melanocytes is suppressed, wherein the target temperature is in a range of 4° C. to 27° C. and the cooling temperature is in a range (whitening temperature range) of −15° C. to 15° C. and lower than the target temperature, and perform skin whitening by maintaining a cooling interval (whitening interval), during which the cooling of the first major surface 31 occurs, in a range of 5 seconds, which is necessary for suppressing the pigmentation, to less than 300 seconds, at which damage to the skin begins.

Also, the mask for whitening skin 10 may apply negative heat to the user's skin and activate the functional material 21 (S230).

In order to increase the activity of the functional material 21 accommodated in the contact layer 20, the mask for whitening skin 10 may, via the thermoelectric module 30, apply negative heat within the activation temperature range of the functional material 21.

For example, the mask for whitening skin 10 may activate the functional material 21 by, via the controller 50, causing the whitening temperature range and the activation temperature range of the functional material 21 to overlap during at least a portion of the whitening interval, during which the cooling of the first major surface occurs within the whitening temperature range.

Because the descriptions given above may apply identically to the method for whitening skin illustrated in FIG. 23, more detailed descriptions will be omitted.

On the other hand, the above-described method for whitening skin may be performed in the same way using the device for whitening skin 11 instead of the mask for whitening skin 10. For example, the device for whitening skin 11 may not only whiten the user's facial skin but also whiten the skin on other body parts of the user by being positioned on a hand area, a foot area, an upper body part, or the like of the user.

Hereinafter, the heat dissipation layer 40 which receives heat generated from the thermoelectric module 30 and dissipates the received heat using a method of exchanging heat through fluid circulation according to an embodiment of the present specification will be described. For example, the mask 10 may include a fluid circulation unit 80 configured to receive heat generated from the thermoelectric module 30 and dissipate the received heat.

Figure 24:
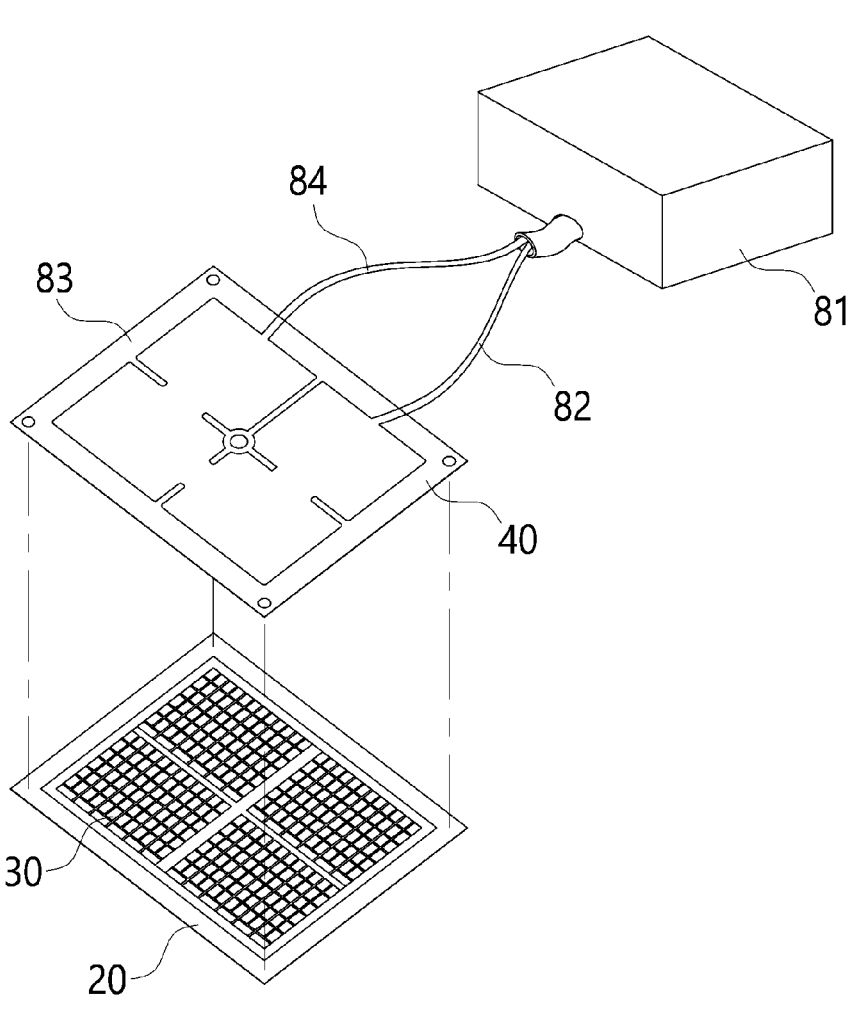
FIG. 24 illustrates a schematic exploded perspective view of a mask including a fluid circulation unit according to an embodiment of the present specification.

FIG. 24 illustrates a schematic exploded perspective view of a mask including a fluid circulation unit according to an embodiment of the present specification. For convenience, the mask 10 including the fluid circulation unit 80 has been illustrated as having a rectangular shape but may also be manufactured in a shape corresponding to a face.

The fluid circulation unit 80 is an element that maintains a predetermined temperature difference between both major surfaces 31 and 32 of the thermoelectric module 30 by removing heat generated from the thermoelectric module 30. The fluid circulation unit 80 may, via a fluid inlet passage 82, supply a circulating fluid to a fluid chamber 83 which has one surface coming in contact with the thermoelectric module 30, exchange heat with the thermoelectric module 30 in the fluid chamber 83, and then retrieve the circulating fluid discharged via a fluid outlet passage 84, thereby circulating the circulating fluid.

To this end, the fluid circulation unit 80 may include a fluid supply part 81, the fluid inlet passage 82, the fluid chamber 83, and the fluid outlet passage 84.

The fluid supply part 81 may supply a circulating fluid, which has a predetermined temperature for receiving heat generated from the thermoelectric module and dissipating the received heat, to the fluid chamber 83. To this end, the fluid supply part 81 may include a fluid tank 85, a pump 86, and a cooler 87.

The fluid tank 85 may store therein a predetermined amount of circulating fluid which will be supplied to the fluid chamber 83. Also, the fluid tank 85 may receive the circulating fluid retrieved via the fluid outlet passage 84 and store the retrieved circulating fluid.

The pump 86 may be connected to the fluid tank 85 and, by pumping, supply the circulating fluid stored in the fluid tank 85 to the fluid chamber 83 via the fluid inlet passage 82. Also, by pumping, the pump 86 may retrieve, via the fluid outlet passage 84, the circulating fluid which finished exchanging heat in the fluid chamber 83 that comes in contact with one surface of the thermoelectric module 30.

The cooler 87 may release heat absorbed by the thermoelectric module 30 to the outside. The cooler 87 may cool the circulating fluid which finished exchanging heat that is retrieved via the fluid outlet passage 84. For example, the cooler 87 may include a radiator, a chiller, and the like for cooling a fluid which will be supplied to the fluid chamber 83.

Also, the cooler 87 may further include a fan.

The fluid inlet passage 82 and the fluid outlet passage 84 may be connected to the fluid supply part 81 and serve as passages that allow the circulating fluid for cooling to pass from the fluid tank 85 to the fluid chamber 83.

Also, the fluid inlet passage 82 and the fluid outlet passage 84 may be connected to the fluid chamber 83. For example, the fluid inlet passage 82 may be connected to a coolant inlet that supplies coolant formed in the fluid chamber 83. Also, the fluid outlet passage 84 may be connected to a coolant outlet that discharges the coolant formed in the fluid chamber 83.

The fluid chamber 83 may be disposed so that at least one surface comes in contact with the thermoelectric module 30. For example, the fluid chamber may be adhered to at least one surface of the thermoelectric module 30 by an adhesive or silicone having high thermal conductivity.

Also, a fluid that absorbs heat generated from the thermoelectric module 30 may pass through the fluid chamber 83, and the fluid chamber 83 may exchange heat with one surface 32 of the thermoelectric module 30 by the fluid passing through the fluid chamber 83. The fluid chamber 83 may allow heat generated from the thermoelectric module 30 to be transferred to the fluid that is supplied via the fluid inlet passage 82 and passes through the fluid chamber 83 and may allow the fluid, to which heat is transferred, to be discharged to the fluid tank 85 via the fluid outlet passage 84.

Also, the fluid chamber 83 may be formed of a material with high thermal conductivity to improve the efficiency of transferring heat generated from the thermoelectric module 30 to the fluid inside the fluid chamber 83. For example, the fluid chamber 83 may be formed of aluminum or the like.

The fluid chamber 83 may also be formed of a material with high flexibility to secure high flexibility of the mask 10. For example, the fluid chamber 83 may be formed of plastic or the like that has high thermal conductivity and flexibility.

According to an embodiment of the present specification, in order to secure high flexibility of the mask 10, the fluid chamber 83 may be provided to be segmented into a plurality of chambers 83 of small sizes. The plurality of fluid chambers 83 may be connected to each other via a connection line (hose). The circulating fluid supplied from the fluid supply part 81 to one fluid chamber 83 may be provided to the plurality of chambers 83 via the connection line (hose). Alternatively, the plurality of fluid chambers 83 may separately receive the circulating fluid from the fluid supply part 81 via the fluid inlet passage 82 and the fluid outlet passage 84 which are separate.

The plurality of fluid chambers 83 may be connected to each other in series and/or in parallel. Each chamber 83 may separately receive the circulating fluid from the fluid supply part 81 via the fluid inlet passage 82 and the fluid outlet passage 84 which are separate. Alternatively, one chamber 83 may receive the circulating fluid from the fluid supply part 81 via one fluid inlet passage 82 and one fluid outlet passage 84, and the received circulating fluid may be provided to other chambers 83 via the connection line (hose).

One of the plurality of fluid chambers 83 may be disposed to come in contact with the at least one thermoelectric module 30. One fluid chamber 83 may be disposed to come in contact with at least one surface of the at least one thermoelectric module 30, and thus a separate module formed of one fluid chamber 83 and at least one thermoelectric module 30 may be provided. For example, one fluid chamber 83 may be disposed to come in contact with at least one surface of one thermoelectric module 30, and a separate module formed of one fluid chamber 83 and one thermoelectric module 30 may be provided.

The controller 50 may control the overall operation of the fluid circulation unit 80. For example, when a measured temperature of the second major surface 32 of the thermoelectric module 30 is higher than a predetermined temperature, the controller 50 may increase the amount of fluid circulating inside the fluid chamber 83 or lower a temperature at which the fluid is supplied. As another example, the controller 50 may determine whether to operate the fluid circulation unit 80 corresponding to the on/off of power of the thermoelectric module 30.

The fluid circulation unit 80 is not necessarily controlled only by the controller 50 and may also be controlled by a separate controller (not illustrated).

Also, the fluid circulation unit 80 may receive power via a separate power supply part (not illustrated) or receive power from a battery (not illustrated) separately accommodated in the fluid supply part 81.

Also, the fluid circulation unit 80 may be implemented as an element included in the cradle 60. For example, the cradle 60 may include the fluid supply part 81, dissipate heat generated from the thermoelectric module 30 of the mask 10, and serve as a place where the mask 10 is mounted.

The circulating fluid may be a material with high thermal efficiency, e.g., high specific heat, for exchanging heat or may be a material which is non-conductive and has low reactivity with the thermoelectric module 30. Specifically, the circulating fluid may be an oil-based fluid, and examples thereof may include natural oil, mineral oil, synthetic oil (e.g., silicone oil), non-conductive liquids (single-phase cooling fluids: 3M's FC-770, FC-3283, FC-40, FC-43, FC-70, FC-72, FC-84, FC-87, etc./two-phase cooling fluids: 3M's Novec Engineered fluids), and the like. Of course, other kinds of fluids such as water may also be used as the circulating fluid, and the circulating fluid may be various kinds of fluids used for exchanging heat.

However, the fluid circulation unit 80 is not limited to the above. The fluid circulation unit 80 may be provided as more or less fluid circulation units 80, and each fluid circulation unit 80 is not limited by the above description.

Figure 25:
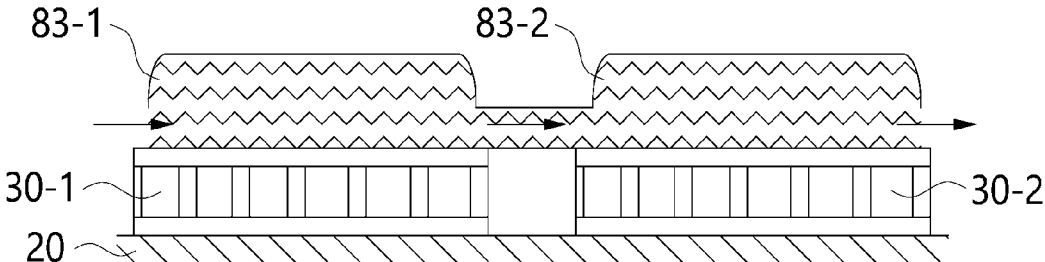
FIG. 25 illustrates a cross-sectional view of the mask including the fluid circulation unit according to an embodiment of the present specification.

FIG. 25 illustrates a cross-sectional view of the mask including the fluid circulation unit according to an embodiment of the present specification.

Referring to FIG. 25, a plurality of fluid chambers 83-1 and 83-2 may be disposed to come in contact with at least one surface of a thermoelectric module 30-1 and at least one surface of a thermoelectric module 30-2, respectively.

When a user operates an operation switch (not illustrated) via the controller 50 while the contact layer 20 is attached to the face of the user, from the operation of the operation switch, the controller 50 may drive the pump 86 while supplying power to the thermoelectric module 30 via a power line, and the pump 86 may control the fluid circulation unit 80 to supply the fluid stored in the fluid tank 85 to the fluid chamber 83 via the fluid inlet passage 82.

The circulating fluid may circulate inside the plurality of fluid chambers 83-1 and 83-2 and be retrieved into the fluid tank 85 via the fluid outlet passage 84. Accordingly, the mask 10 may dissipate heat generated from the thermoelectric module 30 by the fluid circulating inside the fluid chamber 83.

Although FIG. 25 illustrates the plurality of fluid chambers 83-1 and 83-2 as being connected, one fluid chamber 83-1 may form a separate module with one thermoelectric module 30-1 and separately receive a fluid from the fluid supply part 81.

Also, in the method for whitening skin according to the embodiments of the present specification described above, steps in which a subject performing the step is not particularly specified may be performed by the controller 50.

Figure 26:
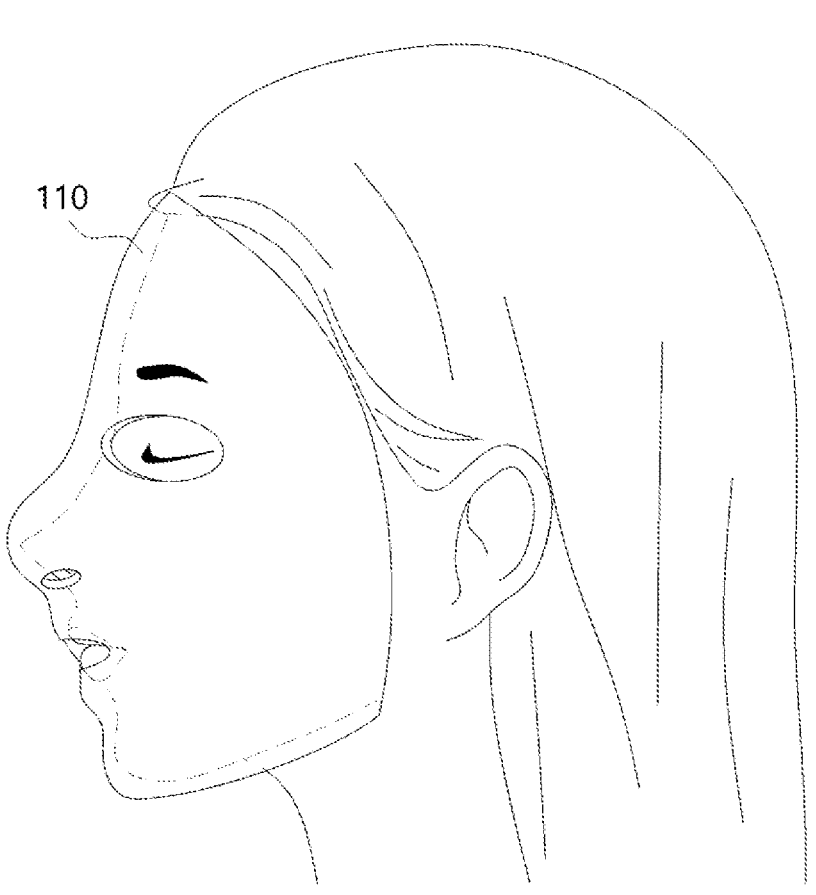
FIG. 26 is a diagram illustrating a state in which a user uses a skin whitening mask according to an embodiment of the present specification.

FIG. 26 is a diagram illustrating a state in which a user uses a skin whitening mask according to an embodiment of the present specification.

The skin whitening mask 110 may be used to apply cold heat to cool the user's skin but cool the skin to a temperature at which pigmentation by melanocytes is suppressed. Specifically, the skin whitening mask 110 cools the melanocytes distributed in the user's skin by maintaining the user's skin at a low temperature for a certain period of time, thereby suppressing pigmentation by reducing the amount of melanin generated from the melanocytes and melanin delivered to the upper part of the skin.

Referring to FIG. 26, the user may use the skin whitening mask 110 to maintain the skin at a low temperature for a certain period of time for skin whitening by using the phase change material of the skin whitening mask 110.

The skin whitening mask 110 may be used after precooling below the melting point of the phase change material included in the mask 110. The skin whitening mask 110 is preferably cooled to the temperature of the melting point of the phase change material contained therein. For example, if the melting point of the phase change material included in the skin whitening mask 110 is −15° C., the user pre-cools the skin whitening mask 110 to −15° C., and then the skin whitening mask 110 can be used.

In addition, in order to prevent skin damage caused by excessive cooling but suppress pigmentation caused by melanocytes, the user may use the skin whitening mask 110 for a duration time in which at least the melting point of the phase change material included in the cooled skin whitening mask 110 is maintained. For example, when the phase change material of the skin whitening mask 110 has a mass for which the melting point is maintained for 120 seconds, the user may use the skin whitening mask 110 for 120 seconds.

Hereinafter, a skin whitening mask 110 according to an embodiment of the present specification will be described with reference to FIGS. 27 to 29.

Figure 27:
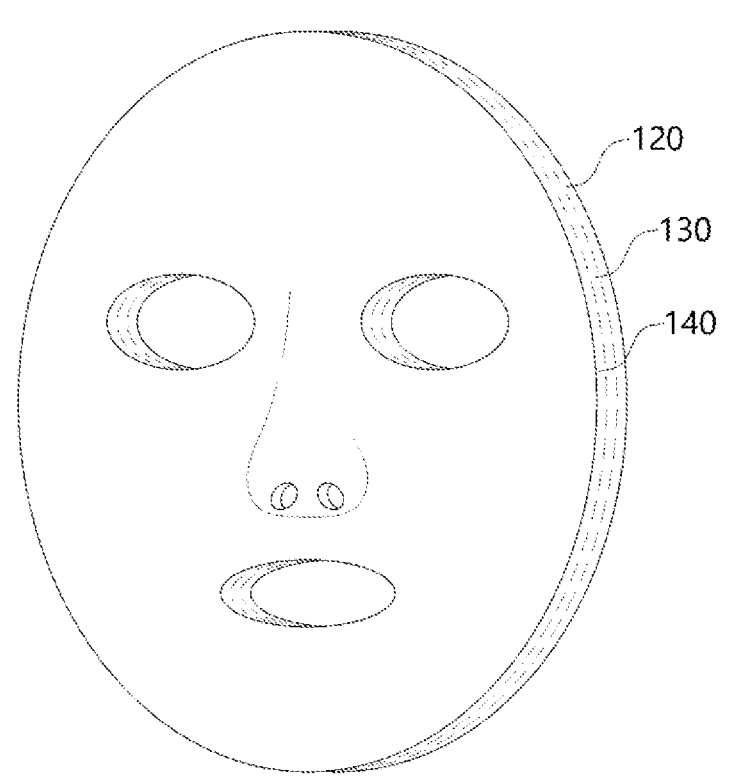
FIG. 27 is a perspective view of a skin whitening mask according to an embodiment of the present specification.

FIG. 27 is a perspective view of a skin whitening mask according to an embodiment of the present specification.

Referring to FIG. 27, the skin whitening mask 110 may have a shape corresponding to the face part to be in close contact with the face part to evenly cool the user's skin, and the user's eye part and mouth part are vulnerable to low temperature, so that the skin whitening mask may be provided in the form of a hole around the eyes and around the mouth. The skin whitening mask 110 may be provided in the form of a hole at the nose part for convenience, such as to improve adhesion.

In addition, the skin whitening mask 110 may include a contact layer 120, a cooling layer 130, and an outer cover 140.

The contact layer 120 may be provided with a flexible material so that the lower portion of the contact layer is in contact with the user's face and is in close contact with the face. In addition, the contact layer 120 may be provided with a material having high thermal conductivity in order to increase the user's skin cooling efficiency through the cooling layer 130. For example, the contact layer 120 may be made of a material such as cotton, bio-cellulose, or hydrogel.

In addition, the contact layer 120 may be provided with a thin thickness to apply negative heat of the cooling layer 130 to the user's skin well. For example, the contact layer 120 may be provided with a thickness of 1 cm or less.

In addition, the contact layer 120 may be provided in a shape corresponding to the user's face. Since the user's eyes and mouth are vulnerable to low temperatures, the contact layer 120 may be provided in the form of a hole around the eyes and around the mouth. The contact layer 120 may be provided in the form of a hole at the nose part for convenience, such as improving adhesion.

In addition, the contact layer 120 may be provided with a viscous liquid to improve adhesion to the skin. For example, the contact layer 120 may be provided in a wetted state with a viscous emulsion.

In addition, various functional materials may be accommodated in the contact layer 120 to obtain an incidental skin improvement effect. For example, the contact layer 120 may be coated with a coating solution, including a functional material.

The functional material is a material that has a skin improvement effect. The functional material may contain, for example, ingredients that help block UV rays, antioxidant ingredients, skin conditioning ingredients, antibacterial ingredients, whitening ingredients (arbutin, niacinamide, ascorbyl glucoside, etc.), pore reduction improvement ingredients, wrinkle improvement ingredients (retinol, adenosine, etc.), vitality filling ingredients, burning sensation prevention ingredients, pain reducing ingredients, and the like. In addition, the functional material may be composed of at least one or two or more ingredients mixture among an ingredient that helps block UV rays, an antioxidant ingredient, a skin conditioning ingredient, an antibacterial ingredient, a whitening ingredient, a pore reduction improvement ingredient, a wrinkle improvement ingredient, a vitality filling ingredient, a burning sensation prevention ingredient, and a pain-reducing ingredient.

In addition, the contact layer 120 may be provided in various forms. The contact layer 120 may be provided by being fixedly disposed on the skin whitening mask 110 but may be provided to be temporarily disposed between the cooling layer 130 and the user's skin when the skin whitening mask 110 is worn. That is, the contact layer 120 is independently configured in a structure detachable from the skin whitening mask 110 and may be separated from the mask 110. For example, the contact layer 120 may be provided as an independent sheet disposed between the cooling layer 130 and the user's skin when worn with the skin whitening mask 110. For another example, the contact layer 120 may be provided in the form of an independent gel that is coated and disposed between the cooling layer 130 and the user's skin when the skin whitening mask 110 is worn.

The functional material may be a material whose function is more activated at a low temperature. For example, the functional material is a whitening functional material and may be a material that has a higher whitening effect at a low temperature (a whitening function is more activated). By way of example and not limitation, the functional material may be formed of one or a mixture of two or more resorcinol and similar derivatives (hexyl resorcinol, Butyl resorcinol, Phenylethyl resorcinol, resorcinol acetate, and other similar derivatives).

For another example, the functional material is a whitening functional material, and may be a material that can be used with an increased effective concentration by further reducing irritation (e.g., irritation caused by cooling) at a low temperature. By way of example and not limitation, the functional material may be formed of one or a mixture of two or more resorcinol and similar derivatives (hexyl resorcinol, Butyl resorcinol, Phenylethyl resorcinol, resorcinol acetate, and other similar derivatives), niacinamide and its containing composition therewith, magnesium ascorbyl phosphate and its containing composition, ascorbyl glucoside and its containing composition, ascorbyl tetraisopalmitate/dipalmitate and its containing composition, arbutin and its containing composition, α-Bisabolol and its containing composition, ethyl ascorbyl ether and its containing composition, polyphenols derivatives and its containing composition, L-glutathione and its containing composition, tranexamic acid and its containing composition, 4-methoxy salicylic acid KCl derivatives and its containing composition, glycyrrhizin and its containing composition, azelaic acid, azelaic acid derivatives (for example, azeloyl diglycine) and its containing composition, nicotinamide, nicotinamide derivatives and its containing composition, resveratrol, resveratrol derivatives and its containing composition, glycyrrhiza flavonoids, ellagic acid and its containing composition, papain and its containing composition, mandelic acid, mandelic acid derivatives and its containing composition, heptapeptide-1 and its containing composition, kojic acid, kojic acid derivatives and its containing composition, plant extracts and a composition containing all or part of the following ingredients: jasmine extract, mulberry extract, paper mulberry extract, licorice extract, ginseng extract, salvia miltiorrhiza extract, corn extract, chrysanthemum extract, bark root extract, thyme extract, white fresh root extract, polygonal extract, magnolia tree extract, angelica root extract, *Phyllanthus emblica* (fruit) extract, citrus and citrus extract, etc.

The cooling layer 130 is disposed on an upper part of the contact layer 120 and may include a phase change material prepared in a state of cooling below the melting point and applying negative heat to the user's skin using latent heat at a melting point for at least a duration in which the melting point is maintained through the contact layer 120.

A phase change material has a large latent heat and can store and release a large amount of energy during phase change. A phase change material stores or releases heat through the process of changing from one state to another, such as from a solid to a liquid state, from a liquid to a solid state, etc. When the external temperature falls below the melting point of the phase change material, the phase change material releases a large amount of latent heat as the phase change material changes a phase, and when the external temperature rises above the intrinsic melting point of the phase change material, the phase change material absorbs a large amount of latent heat as the phase change material changes a phase. Therefore, since the phase change material absorbs or releases a large amount of heat as the phase of the material changes, the temperature corresponding to the melting point can be maintained constant for a longer period of time compared to other materials. That is, the cooling layer 130 may apply cold heat to the user's skin by setting the melting point of the phase change material to a cooling temperature until the phase change of the phase change material is completed.

In addition, the phase change material included in the cooling layer 130 may have a melting point below a target temperature at which pigmentation by melanocytes is suppressed. The target temperature is a skin temperature to be reached through cooling of the skin and may mean the temperature of the user's skin after a duration time for which the melting point of the phase change material is maintained.

The cooling layer 130 may cool the user's skin to a target temperature by applying cold heat to the skin through a phase change material with a melting point below the target temperature. For example, the target temperature may be a temperature in the range of 4° C. to 27° C.

The target temperature may be a temperature of 27° C. or lower. Because the skin whitening effect due to cooling of the skin increases as the temperature of the skin is maintained at a lower temperature, the target temperature may be a temperature of 27° C. or less for the skin whitening effect due to cooling of the skin to occur substantially.

Also, the target temperature may be a temperature of 4° C. or higher. The actual freezing of human skin tissue does not occur before the skin temperature is −4° C. to −110° C., but when the skin temperature falls below 4° C., tissue damage may occur due to ischemia and thrombus in small blood vessels. Therefore, the target temperature may be a temperature of 4° C. or higher to prevent skin damage due to cooling of the skin.

In addition, the cooling layer 130 may include a phase change material having a melting point of −15° C. to 15° C. to provide a cooling temperature that inhibits the activity of melanocytes but prevents skin damage. For example, the cooling layer 130 may include a phase change material such as n-dodecane, $C_{14}H_{30}$, $C_{12}H_{26}$.

In addition, the cooling layer 130 may include a phase change material having a melting point that provides a cooling temperature to a temperature at which the functional material accommodated in the contact layer 110 is activated. For example, the cooling layer 130 may include a phase change material having a melting point at a temperature at which the activity of the functional material accommodated in the contact layer 110 becomes a specific value or more.

However, the cooling temperature of the cooling layer 130 does not need to be limited to the above description, and the cooling temperature may vary depending on circumstances, such as a temperature within a temperature range of −30° C. to 35° C. In addition, the target temperature is not necessarily limited to the above description, and the target temperature may vary depending on circumstances, such as being a temperature of −110° C. to 35° C.

Hereinafter, the mass of the phase change material included in the cooling layer 130 will be described.

If the user's skin is not sufficiently cooled through the skin whitening mask 110, pigmentation caused by melanocytes may not be suppressed, and if the user's skin is excessively cooled, tissue damage due to skin freezing may occur.

Accordingly, in order to prevent skin damage due to cooling during the duration when the melting point of the phase change material is maintained and to suppress pigmentation due to melanocytes, the phase change material included in the cooling layer 130 may have a mass that maintains a melting point longer than a first time required for suppressing pigmentation and shorter than a second time during which skin damage occurs. For example, the phase change material included in the cooling layer 130 may have a mass such that the melting point is maintained for 5 seconds to 300 seconds. For another example, the phase change material included in the cooling layer 130 may have a mass such that the duration time for which the melting point is maintained is a time required for the user's skin to maintain the target temperature for 4 seconds to 120 seconds. For another example, the phase change material included in the cooling layer 130 may have a mass such that the duration time for which the melting point is maintained is from 5 seconds required for suppression of pigmentation to 900 seconds with the possibility of microscopic damage to the skin.

The first time may mean the minimum time required for suppression of pigmentation due to cooling of melanocytes, and when the skin is cooled for a shorter time than the first time period, sufficient cooling of melanocytes is not achieved, so that pigmentation cannot be suppressed. For example, the first time period may be at least 30 seconds to substantially generate a skin whitening effect due to cooling of the skin.

In addition, the first time period may be longer as the melting point of the phase change material included in the cooling layer 130 increases. For example, the first time period may be longer when the melting point of the phase change material included in the cooling layer 130 is 5° C. than when the melting point is −15° C.

In addition, the first time may be obtained as a time during which the user's skin maintains the target temperature. For example, the first time period may be a time required for the user's skin to maintain the target temperature for at least 29 seconds in order to substantially generate a skin whitening effect due to cooling of the skin.

The second time may mean a time at which skin damage starts to occur due to cooling of the skin, and when the skin is cooled for a longer time than the second time period, damage to the skin may occur. For example, the second time period may be up to 300 seconds to prevent tissue damage due to ischemia and thrombus in small blood vessels caused by cooling the skin for a long time. However, the second time period may vary depending on circumstances, such as up to 900 seconds, which is a time period in which direct damage to the skin occurs as well as a possibility of microscopic damage to the skin by cooling the skin for a long time.

In addition, the second time period may be longer as the melting point of the phase change material included in the cooling layer 130 increases. For example, the second time period may be longer when the melting point of the phase change material included in the cooling layer 130 is 5° C. than when the melting point is −15° C.

In addition, the second time may be obtained as a time during which the user's skin maintains the target temperature. For example, the second time period may be a time required for the user's skin to maintain the target temperature for up to 120 seconds in order to prevent tissue damage due to ischemia and thrombus in small blood vessels caused by cooling the skin for a long time.

The cooling duration time of the cooling layer 130 does not need to be limited to the above description and may be variously determined.

According to an embodiment of the present specification, the mass of the phase change material included in the cooling layer 130 may be determined based on the target temperature, the melting point of the phase change material, latent heat at the melting point of the phase change material, and the area of the mask 110.

A method of determining the mass of the phase change material will be described in detail below with reference to FIG. 28. Specifically, the mass (G) of the phase change material can be obtained by the following calculation formulae.

$$\text{[Formula 2]}$$

$$(상변화물질의 질량, G) = \frac{(피부로부터 방출되는 열량, QHC) \cdot (마스크 면적, A)}{(상변화물질의 녹는점에서의 잠열, \Delta H)}$$

$$(피부로부터 방출되는 열량, QCH) = \int_{t=0}^{\tau=max} qHC \partial \tau \qquad \text{[Formula 3]}$$

Figure 28:
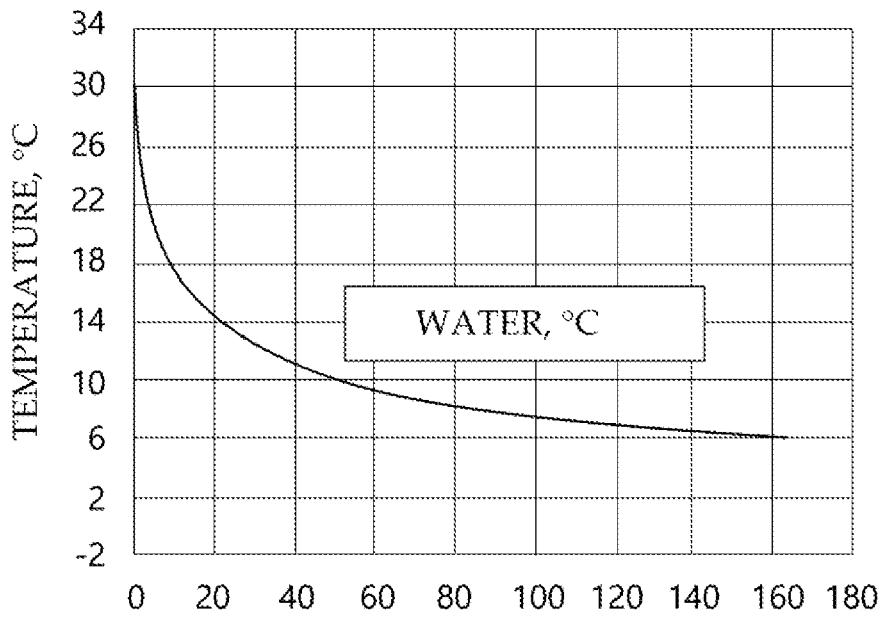
FIG. 28 is a graph showing changes in skin temperature with time when skin cooling is performed through a cooling layer containing water having a melting point of 0° C.

(Where A is the area of the mask 110, ΔH is the latent heat at the melting point of the phase change material, τ is the duration, qHC is the heat flux on the skin surface, QHC is the amount of heat released from the skin) FIG. 28 is a graph showing changes in skin temperature with time when skin cooling is performed through a cooling layer containing water having a melting point of 0° C.

Referring to FIG. 28, the duration time at which the melting point is maintained is 177 seconds, and when the target temperature is 5.5° C., the heat flux of the skin at the initial temperature is 11.3 kW/m², the heat flux of the skin at the target temperature is 0.95 kW/m². Based on this, the mean value of the heat flux of the skin for the duration that the melting point is maintained can be obtained, and the amount of heat emitted from the skin can be calculated through Formula 3 for the duration that the melting point is maintained. As a result of the calculation, the calculated value of the amount of heat emitted from the skin is about 410 KJ/m².

When the skin whitening mask 110 is used for men, the mass G of water is determined to be 0.515 kg when 410 KJ/m² is calculated as the amount of heat emitted from the skin and is substituted into $Q_{HC}$, 419 cm² of the average face area of Korean men is used as the area of the skin whitening mask 110 and is substituted for A, and 333.6 KJ/kg, which is the latent heat at the melting point of water, is substituted for ΔH in Formula 2.

When the skin whitening mask 110 is used for women, the mass G of water is determined to be 0.456 kg when 410 KJ/m² is calculated as the amount of heat emitted from the skin and is substituted into $Q_{HC}$, 371 cm² of the average face area of Korean women is used as the area of the skin whitening mask 110 and is substituted for A, and 333.6 KJ/kg, which is the latent heat at the melting point of water, is substituted for ΔH in Formula 2.

In addition, the mass of the phase change material included in the cooling layer 130 may be determined by another method. For example, the mass (G) of the phase change material included in the cooling layer 130 may be determined based on the average cooling rate (Q, KJ/m²·sec), the latent heat at the melting point of the phase change material (ΔH, KJ/g), and the area of the mask 110 (A, m)². Specifically, G may be determined according to Formula 4 below.

$$G = \frac{Q \cdot A \cdot \tau}{\Delta H} \qquad \text{[Formula 4]}$$

(τ: duration time of maintaining melting point, Q: average cooling rate, A: area of mask 110, ΔH: latent heat at the melting point of a phase change material)

It should be noted that the method of determining the mass of the phase change material included in the cooling layer 130 is not limited to the above-described method and may be performed in various ways.

The outer cover 140 is disposed on an upper portion of the cooling layer 130 and may be provided as a heat insulating material so that the negative heat of the cooling layer 130 does not leak to the outside. In addition, the outer cover 140 may be made of a flexible material to be bent well in response to the user's face. For example, the outer cover 140 may be made of a material such as plastic, expanded polystyrene (EPS), expanded polypropylene (EPP), polyurethane (PU), aerogel, and the like.

In addition, the outer cover 140 may be provided to completely cover the remaining surfaces of the cooling layer 130 except for the surface in which the cooling layer 130 contacts the contact layer 120 to block heat exchange with the outside completely.

In addition, the outer cover 140 may be provided in a shape corresponding to the user's face. For example, the outer cover 140 has a shape corresponding to the face, and since the user's eyes and mouth are vulnerable to low temperatures, the outer cover 140 may be provided in the form of a hole around the eyes and around the mouth. The outer cover 140 may be provided in a form in which a hole is punctured for convenience, such as improving adhesion to the nose part.

Through the outer cover 140, heat transfer from the external environment to the inside of the skin whitening mask 110 may prevent the cooling layer 130 from completing the phase change earlier than the calculated duration time.

On the other hand, although not shown in the drawings, the skin whitening mask 110 according to an embodiment of the present specification may be additionally provided with a strap or a band that provides tension so that the skin whitening mask 110 is sufficiently closely adhered to the skin contacting surface when the user wears the skin whitening mask 110.

However, it is not limited to the above-described configuration, and the skin whitening mask 110 may be a skin whitening mask 110 having more or less configuration than the above configuration, and each configuration is not limited to the above-described description.

Figure 29:
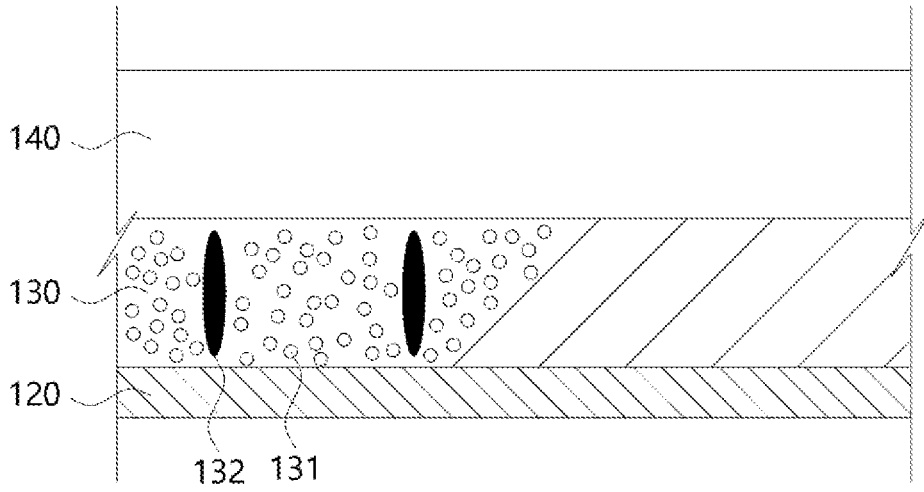
FIG. 29 is a cross-sectional view of a skin whitening mask according to an embodiment of the present specification.

FIG. 29 is a cross-sectional view of a skin whitening mask according to an embodiment of the present specification.

Referring to FIG. 29, the cooling layer 130 may be disposed on the lower portion of the outer cover 140 and disposed on the upper portion of the contact layer 120. When the user wears the skin whitening mask 110, the contact layer 120 may be in direct contact with the user's skin, and the outer cover 140 may be exposed to the external environment.

In addition, the cooling layer 130 may include a phase change material microcapsule 31. The phase change material included in the cooling layer 130 may be prepared in a state cooled to below the melting point so that the cooling layer 130 maintains flexibility even when the phase change material becomes a solid state.

In addition, the cooling layer 130 may include a heat transfer member 132 made of a material having high thermal conductivity in order to efficiently apply negative heat. For example, the cooling layer 130 may include a heat transfer member 132 made of a metal having high thermal conductivity, such as aluminum.

The cooling layer 130 may include a heat transfer member 132 having various shapes. For example, the cooling layer 130 may include a heat transfer member 132 having a shape penetrating the cooling layer 130 up and down, a shape of a thin and long wire, a shape of a small bead, and the like.

Hereinafter, the skin whitening mask 110 having the cooling layers 30a and 30b having a two-layer structure will be described in detail.

When the skin is cooled only through a phase change material having a low melting point, the skin temperature can be rapidly lowered, but if the skin is cooled for a long time, the user may feel pain, and skin damage may occur. When the skin is cooled only through a phase change material having a high melting point, the mass of the phase change material increases so that the miniaturization is difficult, and the skin cooling is not performed quickly. The skin whitening mask 110, according to an embodiment of the present specification, may include cooling layers 30a and 30b having a two-layer structure including different phase change materials to efficiently whiten the skin by cooling the user's skin under two cooling conditions.

Figure 30:
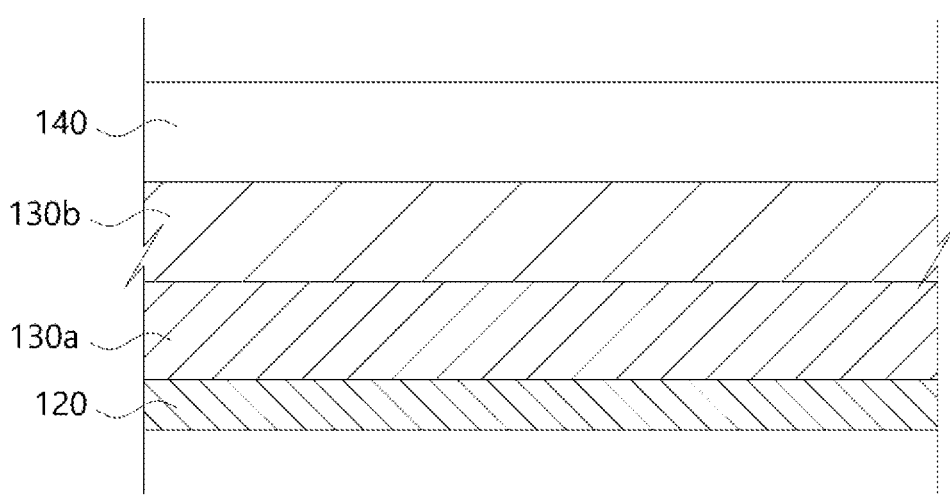
FIG. 30 is a cross-sectional view of a mask having a cooling layer having a two-layer structure according to an embodiment of the present specification.

FIG. 30 is a cross-sectional view of a mask having a cooling layer with a two-layer structure according to an embodiment of the present specification.

Referring to FIG. 30, the skin whitening mask 110 may include a first cooling layer 130a and a second cooling layer 130b.

The cooling layer 130 may include a first cooling layer 130a that is disposed on an upper portion of the contact layer

120 and includes a first phase change material having a first melting point and a second cooling layer 130*b* that is disposed on an upper portion of the first cooling layer 130*a* and includes a second phase change material having a second melting point different from the first melting point. For example, the cooling layer 130 may include a first cooling layer 130*a*, including a first phase change material having a first melting point of 0° C., and a second cooling layer 130*b*, including a second phase change material having a second melting point of minus 15° C.

In addition, the duration time for which the first melting point of the first cooling layer 130*a* is maintained may be different from the duration time for which the second melting point of the second cooling layer 130*b* is maintained. That is, the first phase change material and the second phase change material may have different masses so that the duration time for which the first melting point is maintained and a duration time for which the second melting point is maintained is different. For example, the duration time for which the first melting point of the first cooling layer 130*a* is maintained may be 50 seconds, and the duration time for which the second melting point of the second cooling layer 130*b* is maintained may be 30 seconds.

According to an embodiment of the present specification, in the initial stage of skin cooling, the first cooling layer 130*a* cools the skin to the first melting point to rapidly lower the skin temperature. The first melting point of the first phase change material may be lower than the second melting point of the second phase change material of the second cooling layer 130*b* in order to cool the skin to a temperature higher than the first melting point to prevent skin damage. For example, the first cooling layer 130*a* may include a first phase change material with a first melting point of minus 15° C., and the second cooling layer 130*b* may include a second phase change material with a second melting point of 5° C.

According to an embodiment of the present specification, the duration time for which the first melting point of the first cooling layer 130*a* is maintained may be shorter than the duration time for which the second melting point of the second cooling layer 130*b* is maintained. That is, the first phase change material and the second phase change material may have different masses so that the duration time for which the first melting point is maintained is shorter than the duration time for which the second melting point is maintained. For example, the duration time for which the first melting point of the first cooling layer 130*a* is maintained may be 30 seconds, and the duration time for which the second melting point of the second cooling layer 130*b* is maintained may be 60 seconds.

In addition, the cooling layer 130 may be provided as a cooling layer 130 having a multi-layer structure as well as a two-layer structure.

Figure 31:
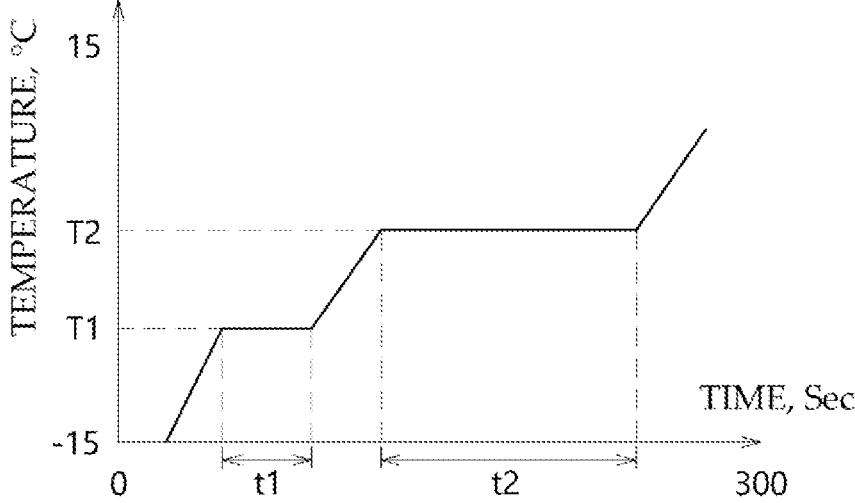
FIG. 31 is a graph showing the temperature over time of the skin whitening mask having a cooling layer having a two-layer structure according to an embodiment of the present specification.

FIG. 31 is a graph showing the temperature over time of the skin whitening mask having a cooling layer of a two-layer structure according to an embodiment of the present specification.

Referring to FIG. 31, the first melting point of the first phase change material of the first cooling layer 130*a* is a temperature lower than the second melting point of the second phase change material of the second cooling layer 130*b*. The duration of maintaining the first melting point of the first cooling layer 130*a* is shorter than the duration of maintaining the second melting point of the second cooling layer 130*b*, thereby indicating a temperature change over time of the skin whitening mask 110.

The mask 110 prepared by cooling to a temperature below the first melting point in advance receives heat from the outside or the user's skin and may reach to T1 (e.g., −10° C.), which is the first melting point of the first phase change material.

When worn by the user, the mask 110 may cool the skin from T1, which is the first melting point of the first phase change material, to t1 (e.g., 15 seconds), which is the duration time for which the first melting point is maintained. Due to the first melting point, which is a low temperature, the temperature of the user's skin may rapidly decrease during t1 hours.

After t1 time elapses and the phase change of the first phase change material is completed, the temperature of the mask 110 rises due to heat emitted from the user's skin and may reach T2 (e.g., 10° C.), which is the second melting point of the second phase change material.

After reaching the temperature T2, mask 110 may cool the skin for a duration of t2 (e.g., 80 seconds), which is a duration time at which the second melting point is maintained at the second melting point T2. Due to the second melting point, which is a temperature higher than the first melting point, the temperature of the user's skin is not lower than the second melting point for time t2, thereby preventing skin damage and cooling the skin for a longer period of time.

After the phase change of the second phase change aterial of the mask 110 is completed, the user may stop wearing the mask 110, and the temperature of the mask 110 is continuously increased by the external environment.

As described above, the skin whitening mask 110 may rapidly lower the skin temperature by cooling the skin to the first melting point at the initial stage of skin cooling. After the duration time in which the first melting point is maintained, the skin whitening mask 110 may cool the skin with a second melting point higher than the first melting point to suppress pigmentation but prevents the skin from cooling to a temperature that damages the skin.

Hereinafter, the skin whitening mask 110, including the cooling layer 130 composed of a plurality of cooling regions, will be described.

Since the plurality of parts constituting the face of a person has different skin characteristics, performing cooling for each part differently is required. For example, the conditions under which skin damage or pigmentation suppression occurs may be different for each part of the body.

Accordingly, a skin whitening mask 110 that cools each part constituting the face of a person differently according to the characteristics of the skin may be provided.

According to an embodiment of the present specification, the skin whitening mask 110 may perform skin cooling differently for each part constituting the face of a person through the cooling layer 130 composed of a plurality of cooling regions.

Figure 32:
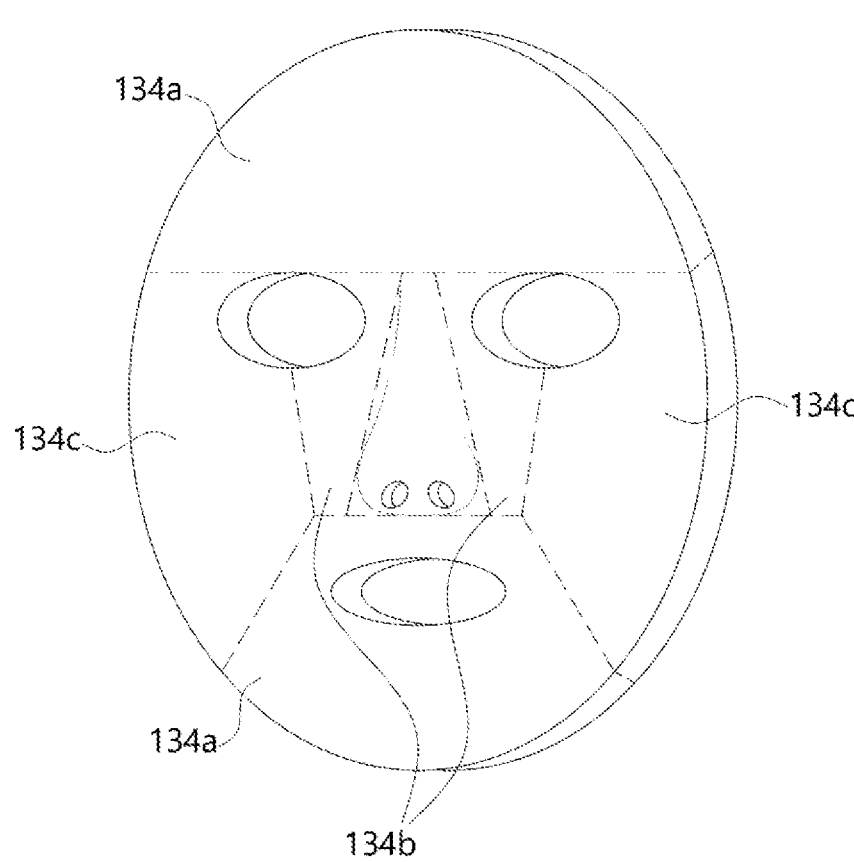
FIG. 32 is a diagram illustrating a cooling layer divided into a plurality of cooling regions according to an embodiment of the present specification.

FIG. 32 is a view showing a cooling layer composed of a plurality of cooling regions according to an embodiment of the present specification.

Referring to FIG. 32, the cooling layer 130 may include a plurality of cooling regions 34*a*, 34*b*, 34*c*, and 34*d* to cool the user's skin under different cooling conditions according to the characteristics of the skin. Each of the cooling regions 34*a*, 34*b*, 34*c*, and 34*d* may include a phase change material having a different melting point, respectively. For example, the first cooling region 134*a* of the cooling layer 130 may include a first phase change material, and the second cooling region 134*b* of the cooling layer 130 may include a second phase change material. Melting points of the first phase change material and the second phase change material may be different from each other.

In addition, each phase change material included in the plurality of cooling regions 34a, 34b, 34c, and 34d may have a mass so that a duration time for maintaining a melting point of the phase change materials included in each cooling region is different.

In addition, in order to prevent the temperature of each cooling zone from becoming the same due to the heat exchange between each cooling region, each of a plurality of cooling regions 34a, 34b, 34c, and 34d may be sealed or isolated from a material having low thermal conductivity.

According to an embodiment of the present specification, a plurality of cooling regions 34a, 34b, 34c, and 34d may be disposed to respectively corresponding to parts having a similar temperature among a plurality of parts constituting the face part to perform skin cooling under different cooling conditions for each part having a similar skin temperature among a plurality of parts constituting the facial part based on the temperature distribution of the facial part.

Referring to FIG. 32, the cooling layer 130 of the skin whitening mask 110 may include a first cooling region 134a corresponding to the forehead and chin, a second cooling region 134b corresponding to both sides of the nose, a third cooling region 134c corresponding to both sides of cheek and a fourth cooling region 34d corresponding to the nose part.

Unlike the internal temperature of a person, the temperature of human skin about 32 to 34° C. is distributed instead of 36 to 37° C., and the temperature distribution of each part of a person's face varies from person to person, but in general, the temperature distribution of the face part is symmetrical in the shape of blood vessels and can be divided into several parts with similar temperatures depending on the temperature. The forehead part has lots of blood vessels, and the heat cannot escape because of the hair, so the temperature is high, and the chin part has a high temperature because there are a lot of blood vessels around it. Both sides of the nose have lots of blood vessels, so the temperature is high, and the temperature of the cheeks are relatively low because there are not many blood vessels. The nose part has a lower temperature than other parts of the face due to the breathing of outside air. That is, in general, the skin temperature is measured high in the order of the forehead, chin, sides of the nose, cheeks, and nose. The skin temperature may be divided into the forehead, chin, sides of the nose, cheeks, and nose, depending on the temperature.

For example, the cooling layer 130 of the skin whitening mask 110 may include a first cooling region 134a corresponding to the forehead and chin having the highest skin temperature, second cooling region 134 corresponding to both sides of the noseband having a second highest skin temperature, a third cooling region 134c corresponding to both cheek parts having the next highest skin temperature, and a fourth cooling region 34d corresponding to a nose part having the lowest skin temperature.

A plurality of cooling regions 34a, 34b, 34c, and 34d may include a phase change material having a lower melting point. The cooling region 34 corresponds to a part having a higher temperature among a plurality of parts constituting the face part. For example, the first cooling region 134a corresponding to the forehead and chin having a high temperature may include a first phase change material having a melting point of −15° C., and the fourth cooling region 34d corresponding to the nose part having a low temperature may include a fourth phase change material having a melting point of 0° C.

In addition, in the plurality of cooling regions 34a, 34b, 34c, and 34d, the duration time for which the melting point is maintained may be longer as the cooling region 34 corresponds to a part having a higher temperature among the plurality of parts constituting the face part. That is, the plurality of cooling regions 34a, 34b, 34c, and 34d may include each phase change material having a mass that increases the duration for maintaining the melting point as the cooling region 34 corresponding to a part having a higher temperature among the plurality of parts constituting the face part. For example, the first cooling region 134a corresponding to the chin and forehead portions having a high temperature may include a mass of the first phase change material such that the melting point is maintained for a duration of 120 seconds, and the second cooling region 134b corresponding to both sides of the nose having a low temperature may include the second phase change material having a mass such that the melting point is maintained for a duration of 60 seconds.

However, the cooling layer 130 having a plurality of cooling regions described above is not limited thereto, and the cooling layer 130 may be a cooling layer 130 having more or fewer cooling regions than the plurality of cooling regions described above. Each cooling region is not limited to the above description.

Hereinafter, the skin whitening mask 110 through which the user can know the using temperature of the skin whitening mask 110 will be described.

The cooling layer 130 may be prepared in a cooled state by being cooled in advance to a temperature excessively lower than the melting point of the included phase change material. When negative heat is applied to the skin through the cooling layer 130 cooled to a temperature excessively lower than the melting point of the phase change material, skin damage due to freezing of the skin or the like may occur. Therefore, according to an embodiment of the present specification, the skin whitening mask 110 indicating whether the temperature of the cooling layer 130 has reached the melting point of the included phase change material may be provided.

Figure 33:
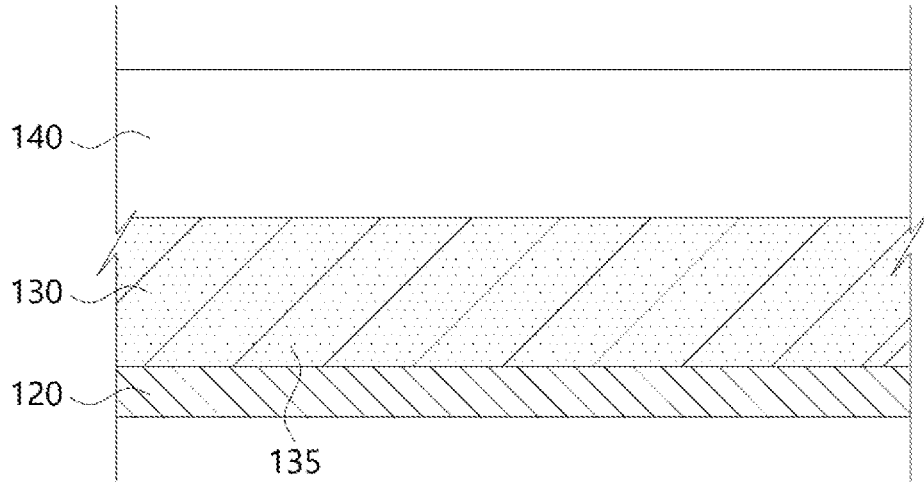
FIG. 33 is a cross-sectional view of a skin whitening mask including a reversible thermochromic pigment according to an embodiment of the present specification.

FIG. 33 is a cross-sectional view of a skin whitening mask including a reversible thermochromic pigment according to an embodiment of the present specification.

Referring to FIG. 33, the cooling layer 130 may include a thermochromic pigment to generate a specific color when the temperature is lower than the melting point of the included phase change material while being transparent at room temperature.

Thermochromic pigments are temperature-changing pigments or heat-sensitive pigments that change color according to temperature and are pigments that have an intrinsic color below a reference temperature and become transparent above the reference temperature.

Thermochromic pigments are largely divided into reversible thermochromic pigments and non-reversible thermochromic pigments. Reversible thermochromic pigments begin to disappear as they reach the reference temperature, completely disappear when they reach the reference temperature, and return to their original color when the temperature drops again. Non-reversible thermochromic pigments cannot return to their original color when the temperature drops again. In one embodiment of the present specification, a reversible thermochromic pigment may be used for repeated use. Various types of thermochromic pigments have been developed and sold at a reference temperature between −15° C. and 70° C., and the temperature at which the color of the pigment changes is usually in the range of 2 to 10° C. before and after the reference temperature.

The cooling layer 130 may include a reversible thermochromic pigment 135 that generates a specific color when the melting point of the phase change material reaches a temperature lower than the reference temperature and disappears and becomes transparent when the melting point reaches a temperature higher than the melting point. For example, the cooling layer 130 may include a reversible thermochromic pigment 135 whose color changes based on −15° C. when the melting point of the included phase change material is −15° C.

In addition, the cooling layer 130 and the phase change material may be transparent so that the color change of the reversible thermochromic pigment 135 can be easily confirmed with the naked eye.

In addition, the cooling layer 130 may not include a reversible thermochromic pigment 135 but may be provided in a form in which one surface is coated with a reversible thermochromic pigment 135.

In addition, the reversible thermochromic pigment 135 may be included in the contact layer 120, the cooling layer 130, and/or the outer cover 140, rather than being included only in the cooling layer 130.

Figure 34:
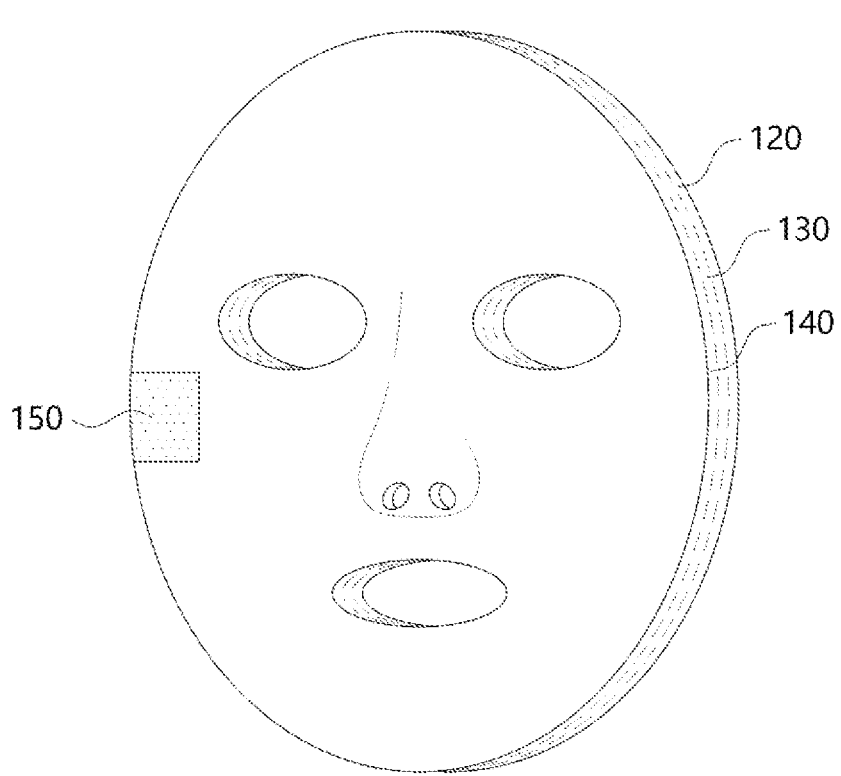
FIG. 34 is a diagram illustrating a skin whitening mask including a device for measuring a temperature and notifying a user according to an embodiment of the present specification.
Figure 35:
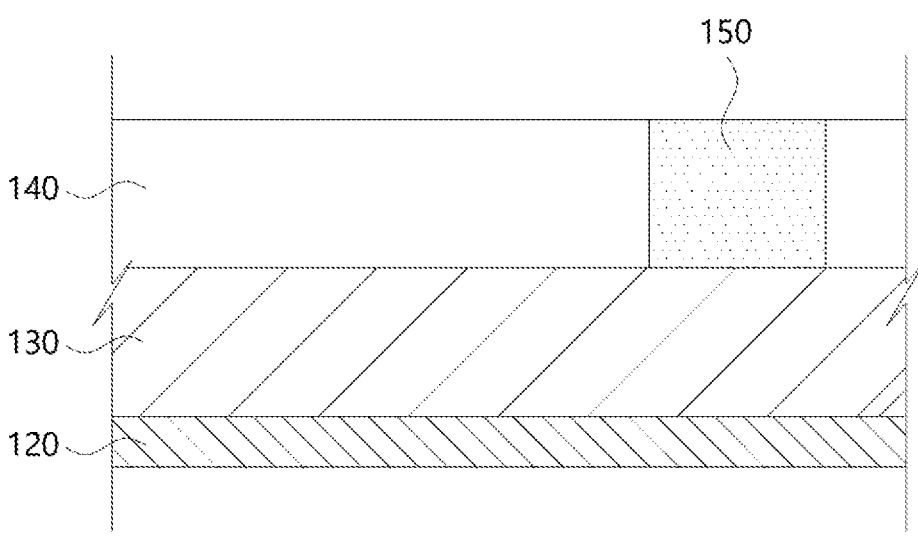
FIG. 35 is a cross-sectional view of a skin whitening mask including a temperature indicating device according to an embodiment of the present specification.

FIG. 34 is a diagram illustrating a skin whitening mask including a temperature indicating device according to an embodiment of the present specification. FIG. 35 is a cross-sectional view of a skin whitening mask including a temperature indicating device according to an embodiment of the present specification.

Referring FIGS. 34 and 35, the skin whitening mask 110 may include a device (hereinafter, referred to as a temperature indicator 50) that measures the temperature of the cooling layer 130 and notifies the user based on the measured temperature.

Referring to FIG. 34, the temperature indicator 150 may be disposed to be exposed on the skin whitening mask 110, but may also be disposed inside the mask 110. For example, the temperature indicator 150 may be disposed in the space formed in the outer cover 140 but may be disposed between the outer cover 140 and the cooling layer 130.

In addition, the temperature indicator 150 may be disposed of at any position of the skin whitening mask 110. For example, the temperature indicating device 150 may be disposed of in various positions, such as a chin part, a forehead part, as well as a cheek part.

In addition, the temperature indicator 150 may be disposed of such that the temperature sensor 151 is in contact with the cooling layer 130. For example, the temperature indicator 150 may be disposed to contact the upper and/or side surfaces of the cooling layer 130, and the temperature sensor 151 may be disposed on a surface of the temperature indicator 150 to contact the cooling layer 130.

In addition, the temperature indicator 150 may be provided while being fixedly disposed on the mask 110 but may be provided to be detachably attached. For example, the temperature indicator 150 may be detached during a pre-cooling process of the mask 110 and may be disposed inside a housing (not shown) formed in the outer cover 140 to be mounted after cooling of the mask 110 is completed.

Figure 36:
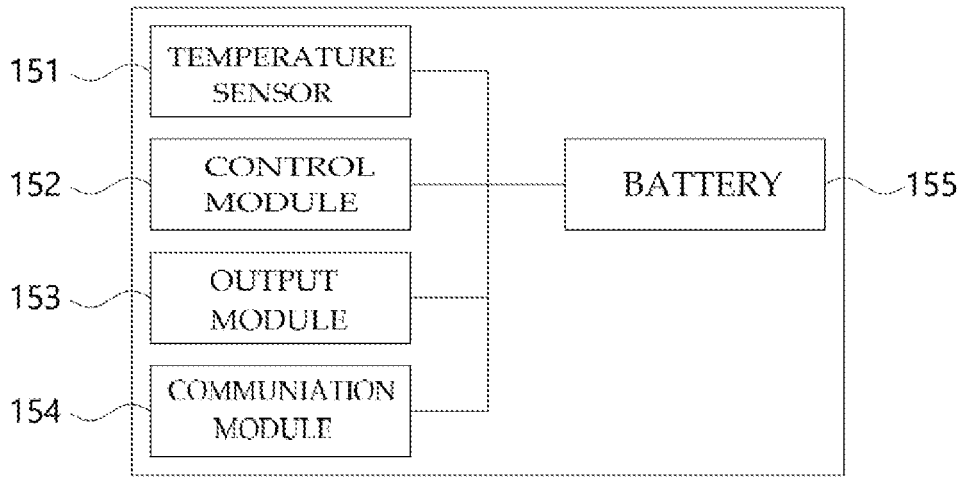
FIG. 36 is a diagram illustrating a configuration diagram of a temperature indicating device according to an embodiment of the present specification.

FIG. 36 is a diagram illustrating a configuration diagram of a temperature indicator according to an embodiment of the present specification.

Referring to FIG. 36, the temperature indicator 150 may include a temperature sensor 151, a control unit 152, an output unit 153, a communication unit 154, and a battery 155.

The temperature sensor 151 may be disposed to contact the cooling layer 130 to measure the temperature of the cooling layer 130. For example, temperature sensor 151 may be a temperature measuring sensors such as a liquid expansion temperature sensor, a state change temperature sensor, a thermocouple, or an RTD.

The control unit 152 may control the overall temperature indicating device 150 or process and calculate various types of information.

In addition, the control unit 152 may control to give a notification to the user about the attachment and detachment of the mask 110 based on the temperature measured by the temperature sensor 151.

The control unit 152 may provide a notification when the temperature measured by the temperature sensor 151 reaches the melting point of the phase change material from a temperature lower than the melting point of the phase change material. That is, when the temperature measured by the temperature sensor 151 reaches the melting point of the phase change material, the control unit 152 may determine that mask 110 is in use. For example, when the temperature measured by the temperature sensor 151 reaches the melting point of the phase change material, the control unit 152 may control to output a voice through the output unit 153. As another example, when the temperature measured by the temperature sensor 151 reaches the melting point of the phase change material, the control unit 152 may transmit a notification message to the user's terminal through the communication unit 154.

In addition, the control unit 152 may give a notification when the temperature measured by the temperature sensor 151 after the user wears the mask 110 is higher than the melting point of the phase change material. That is, when the temperature measured by the temperature sensor is higher than the melting point of the phase change material, the control unit 152 may determine to end the use of the mask 110. For example, when the temperature measured by the temperature sensor 151 is higher than the melting point of the phase change material, the control unit 152 may control to output a voice through the output unit 153. As another example, when the temperature measured by the temperature sensor 151 is higher than the melting point of the phase change material, the control unit 152 may transmit a notification message to the user's terminal through the communication unit 154.

In addition, the control unit 152 may be implemented as software, hardware, or a combination thereof. For example, in terms of hardware, the control unit 152 may be implemented as a field-programmable gate array (FPGA), an application-specific integrated circuit (ASIC), a semiconductor chip, or other various types of electronic circuits. Also, for example, in terms of software, the control unit 152 may be implemented in a logic program executed according to the above-described hardware or in various computer languages.

The output unit 153 may output various notifications to the user. The notification may be delivered visually to the user or may be delivered aurally, for example, by a sound, etc. There is no limitation in the expression method. For example, when receiving a predetermined signal from controller 152, the output unit 153 may output the fact as audio-visual information and/or vibration. The output unit 153 that outputs visual information may be an LCD, OLED, or AMOLED display and may be a speaker or a buzzer that outputs auditory information.

In addition, the output unit 153 may generate vibration to be applied to the user's skin. For example, the output unit 153 may apply vibration to the user's skin by generating vibration to reduce pain caused by cooling. In addition, the output unit 153 may apply the vibration to the user's skin by generating vibration for massage of the user's skin. The output unit 153 may be provided as a vibrator outputting vibration, a vibration motor, or the like.

Communication unit 154 may communicate with the user's terminal and transmit various notifications to the user's terminal. For example, the communication unit 154 may transmit a notification message to the user's terminal through the communication unit 154 when the temperature measured by the temperature sensor 151 reaches the melting point of the phase change material and may transmit a notification message to the user's terminal when the measured temperature measured by the temperature sensor 151 is higher than the melting point of the phase change material.

Communication unit 154 may include an infrared module, near field communication (NFC) module, Bluetooth low energy (BLE), Bluetooth-module, Wi-Fi (Wi-Fi) module, mobile communication including 3G, 4G, or 5G, and other various communication standards.

The battery 155 may supply power to the temperature indicator 150. The battery 155 may be installed to be accommodated in the temperature indicator 150.

In addition, although not shown in the drawings, the temperature indicator 150 may be connected to an external power source through a power supply unit instead of the battery 155 to receive power from the outside.

However, it is not limited to the above-described configuration, and the temperature indicator 150 may be a temperature indicator 150 having more or fewer configurations than the configuration, and each configuration is not limited to the above description.

Hereinafter, a skin whitening device 111 used for various body parts will be described.

This specification describes only the application of the skin whitening mask 110 according to an embodiment of the present specification to the face for convenience, but the skin whitening mask 110 can be provided as the skin whitening device 111 not only applied to the face but also various body parts, such as the hands, thighs, ankles, buttocks, neck, clavicle, arms, and chest. The shape of the skin whitening device 111 may be variously provided in a shape corresponding to each body part.

Figure 37:
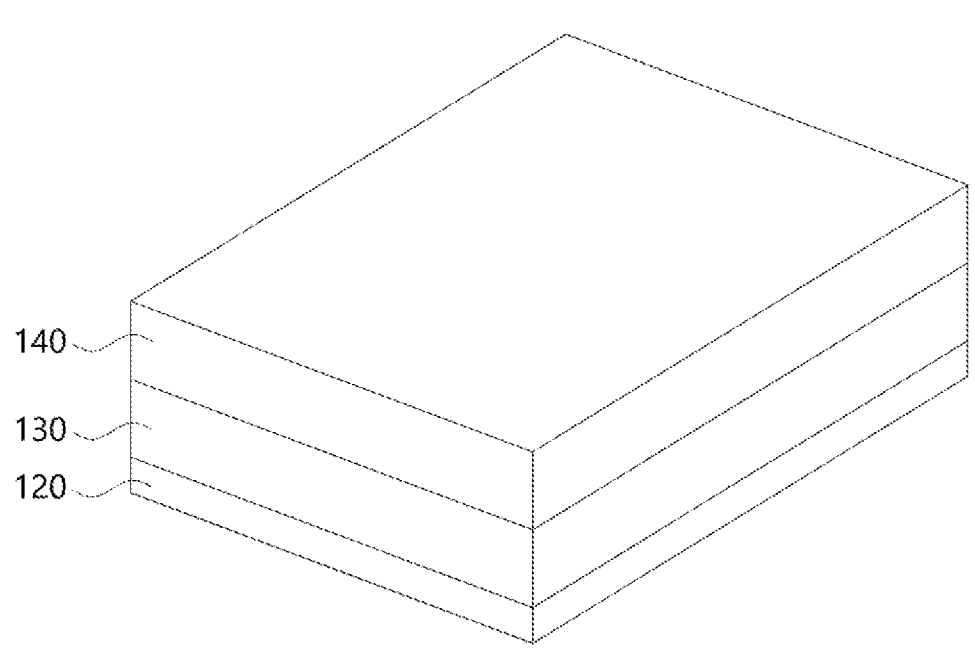
FIG. 37 is a front view of a skin whitening device according to an embodiment of the present specification.

FIG. 37 is a front view of a skin whitening device according to an embodiment of the present specification.

Referring to FIG. 37, the skin whitening device 111 may be provided in the form of a pad as a basic form for adhering to various body parts of the user. Although only the skin whitening device 111 provided in the form of a pad is illustrated in FIG. 37, the skin whitening device 111 may be provided in various forms. For example, the skin whitening device 111 may be provided in a shape corresponding to the various body parts to be in close contact with the user's various body parts to evenly cool the user's skin.

In addition, the skin whitening device 111 may include a contact layer 120, a cooling layer 130, and an outer cover 140.

The contact layer 120 may be made of a flexible material so that the lower part thereof contacts the user's body part and is in close contact with the body part. Since the contact layer 120 has been described above, a detailed description thereof will be omitted.

The cooling layer 130 is disposed on an upper part of the contact layer 120 and may include a phase change material prepared in a state of cooling below the melting point and applying negative heat to the user's skin using latent heat at a melting point for at least a duration in which the melting point is maintained through the contact layer 120. The phase change material may have a mass that has a melting point below the target temperature at which pigmentation by melanocytes is suppressed and maintains the duration time longer than the first time required for suppressing pigmentation and shorter than the second time when skin damage occurs. Since the cooling layer 130 has been described above, a detailed description thereof will be omitted.

The outer cover 140 is disposed on an upper portion of the cooling layer 130 and may be provided as a heat insulating material so that the negative heat of the cooling layer 130 does not leak to the outside. In addition, the outer cover 140 may be provided in a shape corresponding to the body part of the user. Since the outer cover 140 has been described above, a detailed description thereof will be omitted.

On the other hand, although not shown in the drawings, the skin whitening device 111, according to an embodiment of the present specification, may further provide a strap or band that provides tension so as to sufficiently adhere to the surface in contact with the skin when using the user's skin whitening device 111.

However, it is not limited to the above-described configuration, and the skin whitening device 111 may be a skin whitening device 111 having more or fewer configurations than the above configuration, and each configuration is not limited to the above-described description.

Figure 38:
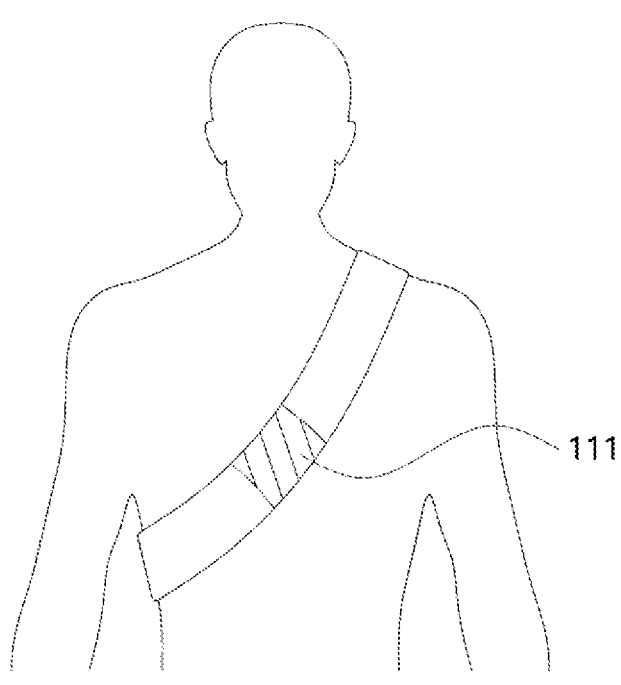
FIG. 38 is a diagram illustrating a state in which a skin whitening device according to an embodiment of the present specification is used on a user's upper body.

FIG. 38 is a diagram illustrating a state in which the skin whitening device, according to an embodiment of the present specification, is used on a user's upper body.

Referring to FIG. 38, the skin whitening device 111 is provided in the form of a pad and can be used on the user's upper body.

Figure 39:
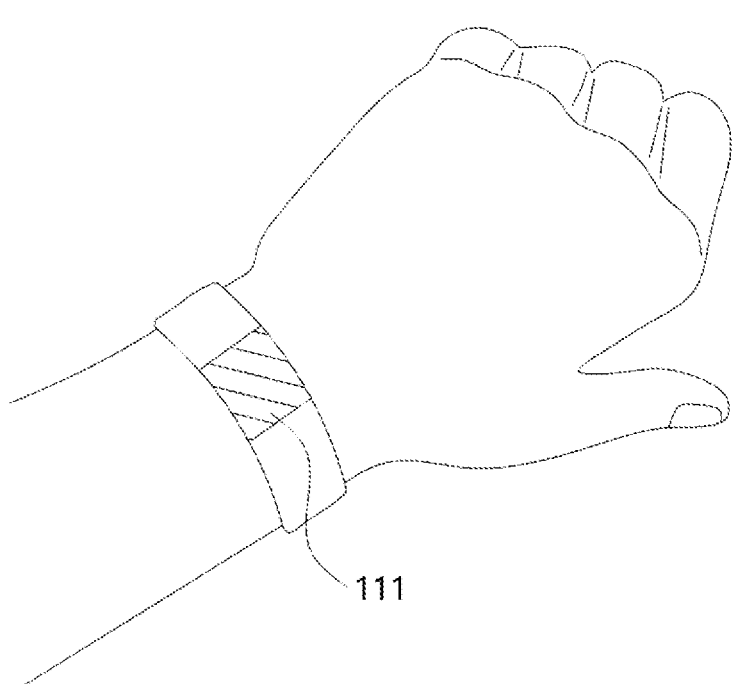
FIG. 39 is a diagram illustrating a state in which a skin whitening device according to an embodiment of the present specification is used on a user's wrist.

FIG. 39 is a diagram illustrating a state in which the skin whitening device, according to an embodiment of the present specification, is used on a user's wrist.

Referring to FIG. 39, the skin whitening device 111 is provided in the form of a band corresponding to the wrist and can be used on the user's wrist.

Figure 40:
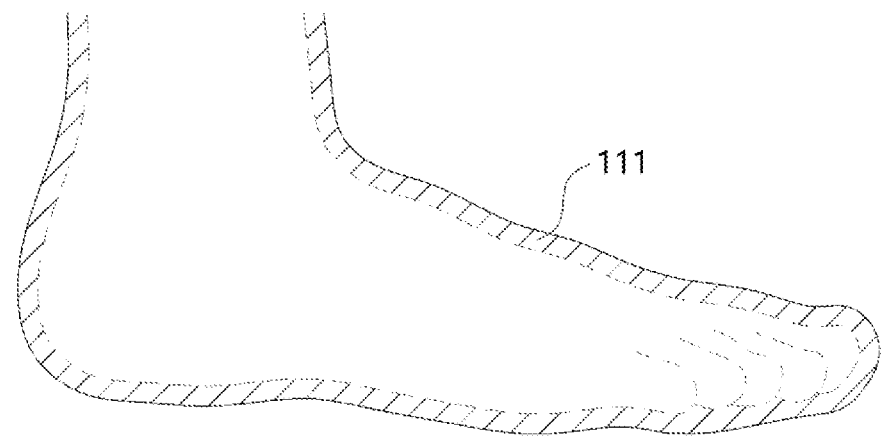
FIG. 40 is a diagram illustrating a state in which a skin whitening device according to an embodiment of the present specification is used on a user's foot.

FIG. 40 is a diagram illustrating a state in which the skin whitening device, according to an embodiment of the present specification, is used on a user's foot.

Referring to FIG. 40, the skin whitening device 111 may be provided in a shape corresponding to the foot and used on the user's foot.

Figure 41:
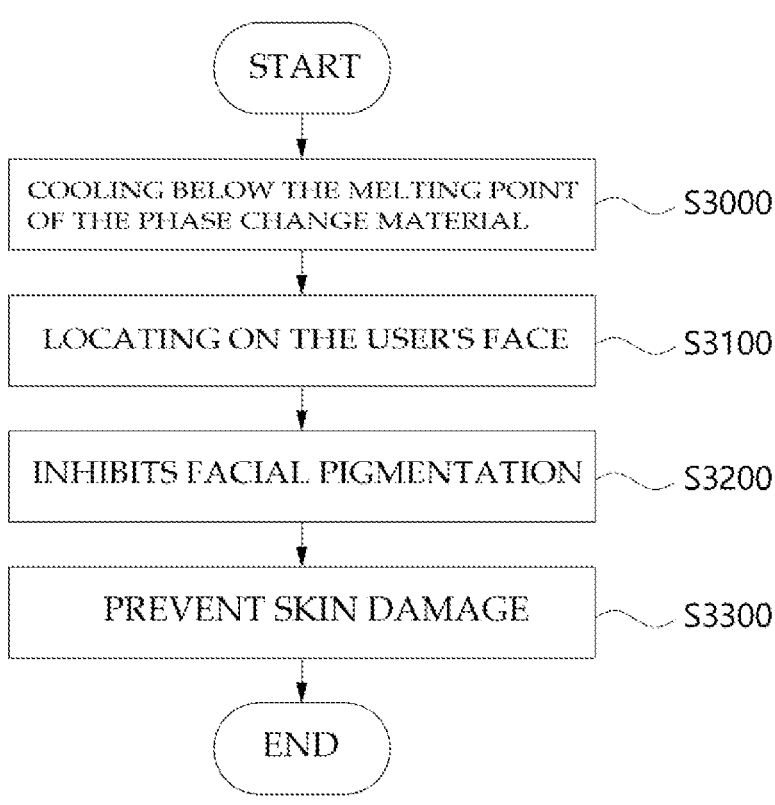
FIG. 41 is a flowchart of a skin whitening method using a skin whitening mask according to an embodiment of the present specification.

FIG. 41 is a flowchart of a skin whitening method using a skin whitening mask according to an embodiment of the present specification.

Referring to FIG. 41, the skin whitening method includes steps of: cooling below the melting point of the phase change material (S3000); positioning on the user's face (S3100); suppressing pigmentation of the face (S3200); and preventing damage (S3300).

A step of cooling the skin whitening mask 110 below the melting point of the phase change material may be performed (S3000).

The skin whitening mask 110 may include a contact layer having a lower portion in contact with a face surface of a user, and provided as a flexible material, a cooling layer 130 includes a phase change material disposed on the contact layer 120 and having a melting point lower than a target temperature at which pigment deposition by melanocytes is suppressed, and an outer cover 140 disposed on the cooling layer 130, provided in a shape corresponding to the user's face, and provided as an insulating material that insulates the cooling layer 130 from the outside. The cooling layer 130 of the skin whitening mask 110 may be cooled below the melting point of the phase change material.

In this case, the mass of the phase change material included in the cooling layer 130 may be determined based on the target temperature, the melting point of the phase change material, the latent heat at the melting point of the phase change material, and the area of the mask 110. Specifically, the mass G of the phase change material included in the cooling layer 130 may be determined by Formulae 2 and 3 below.

$$G = \frac{(QHC) \cdot (A)}{(\Delta H)} \qquad \text{(Formula 2)}$$

$$QHC = \int_{\tau=0}^{\tau=max} qHC \partial \tau \qquad \text{(Formula 2)}$$

(Where A is the area of the mask 110, $\Delta H$ is the latent heat at the melting point of the phase change material, $\tau$ is the duration, qHC is the heat flux on the skin surface, $Q_{HC}$ is the amount of heat released from the skin)

In addition, the phase change material included in the cooling layer 130 may have a melting point in the range of $-15°$ C. to $15°$ C.

In addition, the target temperature may be in the range of $4°$ C. to $27°$ C.

In addition, the phase change material included in the cooling layer 130 may be composed of a phase change material microcapsule (PCM microcapsule).

In addition, the cooling layer 130 may include a thermochromic pigment that has a specific color at a temperature lower than the melting point of the phase change material and becomes transparent when the temperature reaches the melting point.

In addition, the cooling layer 130 may include the first cooling layer 130*a* being disposed on an upper part of the contact layer 120, including the first phase change material having a first melting point and a second cooling layer 130*b* being disposed on an upper part of the first cooling layer 130*a*, including a second phase change material having a second melting point different from the first melting point. In this case, the first melting point may be a temperature lower than the second melting point. In addition, the duration time for which the first melting point is maintained may be different from the duration time for which the second melting point is maintained. In addition, the duration time for which the first melting point is maintained may be shorter than the duration time for which the second melting point is maintained.

In addition, the cooling layer 130 is composed of a plurality of cooling regions, including a phase change material having a different melting point, and the plurality of cooling regions may be arranged to correspond to parts having a similar temperature among a plurality of parts constituting the face part, respectively. In this case, the plurality of cooling regions may include a phase change material having a lower melting point as the cooling region corresponding to a part having a higher temperature among the plurality of parts constituting the face part. In addition, the plurality of cooling regions may have a longer duration time for which melting points are maintained as the cooling regions corresponding to the parts having a higher temperature among the plurality of parts constituting the face part.

In addition, the skin whitening mask 110 may further include a temperature indicator 150 disposed to contact the cooling layer 130 to measure the temperature of the cooling layer 130. At this time, the temperature indicator 150 may include a temperature sensor 151 that measures the temperature of the cooling layer 130, a communication unit 154 that communicates with the user's terminal, and a control unit 152 that controls to give a notification about the detachment of the mask 110 to the user's terminal based on the measured temperature through a communication unit 154.

A step of placing the skin whitening mask 110 on the user's face may be performed (S3100).

The skin whitening mask 110 may be positioned on the user's face so that the lower part of the contact layer 120 is in close contact with the face.

In addition, a lower part of the contact layer 120 to which a coating solution including a functional material for an incidental skin improvement effect is applied may be positioned on the user's face.

In addition, a strap or a band for providing tension to the skin whitening mask 110 is additionally provided so that the skin whitening mask can sufficiently adhere to the skin in contact with the user's skin. A step of suppressing pigmentation of the facial skin by the skin whitening mask 110 may be performed (S3200).

The skin whitening mask 110 may apply cold heat to the user's skin using latent heat at the melting point of the phase change material for a duration of at least a melting point through the contact layer 120 to be maintained longer than a first time required to suppress the pigmentation, thereby suppressing the pigmentation of the face skin attached to the lower part of the contact layer 120 closely.

At this time, the first time period may be at least 30 seconds. In addition, the first time may be the time required for the skin to maintain the target temperature for at least 29 seconds.

A step of preventing the skin whitening mask 110 from damaging the facial skin may be performed (S3300).

The skin whitening mask 110 may prevent damage to the facial skin as the phase change of the phase change material ends before the second time elapses when the damage to the skin occurs.

At this time, the second time may be up to 300 seconds. In addition, the second time may be a time required for the skin to maintain the target temperature for up to 120 seconds.

On the other hand, the above-described skin whitening method may be similarly performed using the skin whitening device 111 as well as the skin whitening mask 110. For example, the skin whitening device 111 may not only whiten the user's facial skin but may whiten the skin located on other parts of the user, such as hands, feet, and upper body, and the like.

Since the above-described description may be applied to the skin whitening method shown in FIG. 41, more details will be omitted.

Since each of the steps described in the skin whitening method according to the embodiment of the present specification described above is not essential, the skin whitening method may be performed including all of the steps as well as only some of the steps. In addition, since the order in which each step is described is only for the convenience of explanation, each step in the skin whitening method does not necessarily have to be performed in the described order.

The above description is merely illustrative of the technical spirit of the present invention, and various modifications and variations will be possible without departing from the essential characteristics of the present invention by those skilled in the art to which the present invention pertains.

Accordingly, the embodiments of the present invention described above may be implemented separately or in combination with each other.

FORM FOR IMPLEMENTATION OF THE INVENTION

As described above, in the best mode for carrying out the invention, related matters have been described.

What is claimed is:

1. A whitening device, comprising:
a first mask layer;
a second mask layer provided with a material having a higher flexibility than the first mask layer, wherein the second mask layer is configured to contact a face of a user when the whitening device is worn over the face of the user;
a flexible thermoelectric module configured to be interposed between the first mask layer and the second mask layer and to be in contact with the second mask layer, wherein the flexible thermoelectric module includes a plurality of thermoelectric elements, wherein the flexible thermoelectric module comprises a first main surface in contact with the second mask layer and a second main surface located on the opposite side of the first main surface; and
a fluid layer positioned on a side of the second main surface of the flexible thermoelectric module to absorb heat generated from the second main surface when the first main surface is cooled, wherein the fluid layer comprises at least one fluid chamber, wherein the at least one fluid chamber is configured to cover at least a portion of the second main surface of the flexible thermoelectric module, wherein the at least one fluid chamber is configured to be supplied with fluid from a fluid tank through at least one fluid line;
wherein the flexible thermoelectric module and the fluid layer are structurally configured to satisfy all of the following conditions so as to allow the fluid layer to change a shape of a fluid area occupied by the fluid layer between the flexible thermoelectric module and the first mask layer when an external force is applied to the second mask layer:
a) the flexible thermoelectric module is provided with a flexible material in an interior of the flexible thermoelectric module, and the first main surface and the second main surface each comprise a thin polyimide film,
b) the flexible thermoelectric module is configured to have a higher flexibility than the first mask layer,
c) the fluid layer is configured to be interposed between the first mask layer and the flexible thermoelectric module, allowing the fluid layer to occupy at least a portion of an area between the flexible thermoelectric module and the first mask layer,
d) the at least one fluid chamber is configured to have a higher flexibility than the first mask layer, and
e) wherein a thickness of the at least one fluid chamber is greater than a thickness of the at least one fluid line.

2. The whitening device of the claim 1, wherein a shape of the first mask layer is not changed by the external force applied to the second mask layer.

3. The whitening device of the claim 1,
wherein the flexible thermoelectric module is provided in the form of an array in which the plurality of thermoelectric elements are electrically connected.

4. The whitening device of the claim 1, wherein the flexible thermoelectric module includes a first flexible thermoelectric module and a second flexible thermoelectric module,
wherein the first flexible thermoelectric module and the second flexible thermoelectric module are independently controlled.

5. The whitening device of the claim 4, wherein a distance between the first flexible thermoelectric module and the second flexible thermoelectric module is greater than a distance between two adjacent thermoelectric elements included in the first flexible thermoelectric module.

6. The whitening device of the claim 5,
wherein the distance between the first flexible thermoelectric module and the second flexible thermoelectric module is less than or equal to a first distance.

7. The whitening device of the claim 6,
wherein the first distance is 1 cm to reduce partial whitening of the face of the user.

8. The whitening device of the claim 1,
wherein the flexible thermoelectric module includes a first flexible thermoelectric module and a second flexible thermoelectric module,
wherein the at least one fluid chamber includes a first fluid chamber and a second fluid chamber,
wherein the first fluid chamber is in contact with a second main surface of the first flexible thermoelectric module,
wherein the second fluid chamber is in contact with a second main surface of the second flexible thermoelectric module,
wherein the first fluid chamber and the second fluid chamber are fluidly connected to each other,
wherein a volume of the first fluid chamber and a volume of the second fluid chamber are greater than a volume of the at least one fluid line.

9. The whitening device of the claim 1,
wherein the whitening device further includes a controller for controlling an operation of the flexible thermoelectric module,
wherein the controller is configured to control the first main surface of the flexible thermoelectric module to be cooled to a target temperature in a range of −15° C. and 15° C.

10. The whitening device of the claim 9,
wherein the controller is configured to control the first main surface of the flexible thermoelectric module to maintain the target temperature in a range of 5 seconds to 300 seconds.

11. The whitening device of the claim 1,
wherein the first mask layer is provided in a predetermined shape,
wherein when the whitening device is worn over the face of the user, as the shape of the fluid area occupied by the fluid layer between the flexible thermoelectric module and the first mask layer is changed, a shape of the second mask layer is changed to a shape that is more closely contoured to the face of the user than the predetermined shape.

* * * * *